(12) United States Patent
Loeb

(10) Patent No.: US 7,994,123 B2
(45) Date of Patent: Aug. 9, 2011

(54) HYBRID PROTEINS WITH ERBB4 EXTRACELLULAR DOMAIN AND NEUREGULIN HEPARIN-BINDING DOMAIN FOR TARGETING

(75) Inventor: Jeffrey A. Loeb, Beverly Hills, MI (US)

(73) Assignee: Wayne State University, Detroit, MI (US)

( * ) Notice: Subject to any disclaimer, the term of this patent is extended or adjusted under 35 U.S.C. 154(b) by 799 days.

(21) Appl. No.: 11/631,977

(22) PCT Filed: Jul. 8, 2005

(86) PCT No.: PCT/US2005/024279
§ 371 (c)(1),
(2), (4) Date: Jan. 3, 2008

(87) PCT Pub. No.: WO2006/017184
PCT Pub. Date: Feb. 16, 2006

(65) Prior Publication Data
US 2008/0207484 A1 Aug. 28, 2008

Related U.S. Application Data

(60) Provisional application No. 60/586,283, filed on Jul. 9, 2004, provisional application No. 60/608,096, filed on Sep. 9, 2004, provisional application No. 60/616,834, filed on Oct. 8, 2004.

(51) Int. Cl.
*A61K 38/18* (2006.01)
*A61K 38/00* (2006.01)
*C12N 15/00* (2006.01)
*C12N 5/00* (2006.01)

(52) U.S. Cl. ........ 514/7.6; 514/9.6; 514/18.1; 514/19.3; 514/19.4; 514/21.2; 435/69.7; 435/375

(58) Field of Classification Search ................. None
See application file for complete search history.

(56) References Cited

FOREIGN PATENT DOCUMENTS
WO WO 03/012045 A2 * 2/2003

OTHER PUBLICATIONS
Plowman et al., Proc. Natl. Acad. Sci., 1993, vol. 90(5):1746-50.*
Heath et al., Biochemistry, 1991, vol. 30:5608-5614.*

\* cited by examiner

*Primary Examiner* — Elizabeth C Kemmerer
*Assistant Examiner* — Xiaozhen Xie
(74) *Attorney, Agent, or Firm* — Browdy and Neimark, PLLC

(57) ABSTRACT

Polypeptides of the neuregulin (NRG) heparin binding domain (N-HBD) and nucleic acids coding therefor are disclosed. In particular, fusion polypeptides are produced that comprise, as a targeting structure, a N-HBD polypeptide, fragment, homologue or functional derivative and a protein to be targeted. This is fused to a polypeptide or peptide being targeted ($P_{trg}$) to cell surfaces rich in heparan sulfate proteoglycans to either activate or inhibit interactions at tyrosine kinase receptors. A preferred fusion polypeptide comprises an N-HBD, a spacer and the extracellular domain of erbB4, one of several receptors signaled by NRG, which is potent NRG antagonist. Such products are used to treat diseases or conditions where either agonism or antagonism at tyrosine kinase receptors has beneficial effects, including cancer and a multitude of diseases of the nervous system.

12 Claims, 22 Drawing Sheets

Fig. 2A
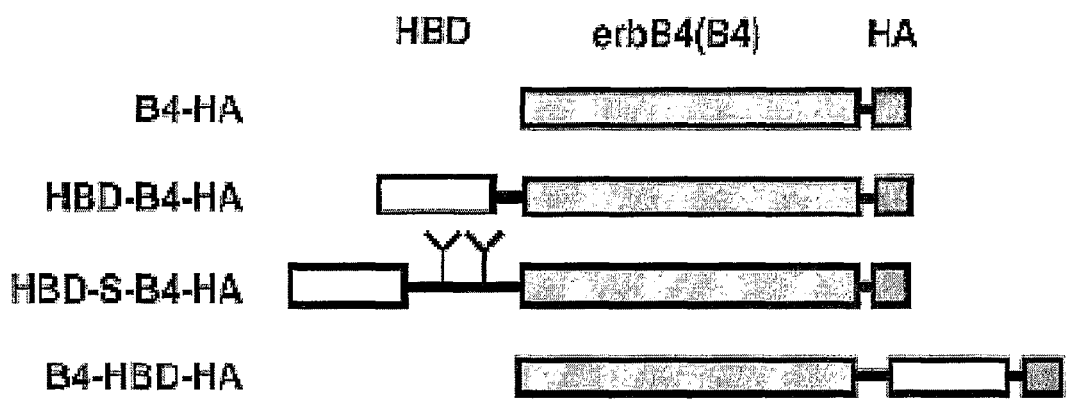
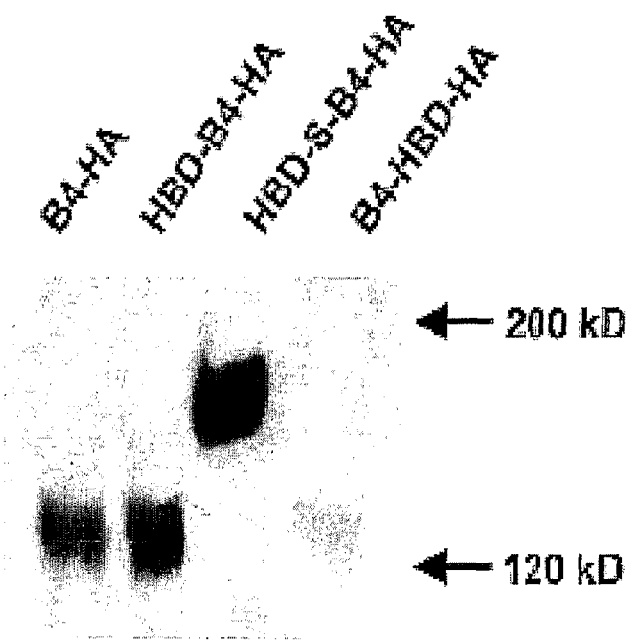
Fig. 2B

Fig. 5C
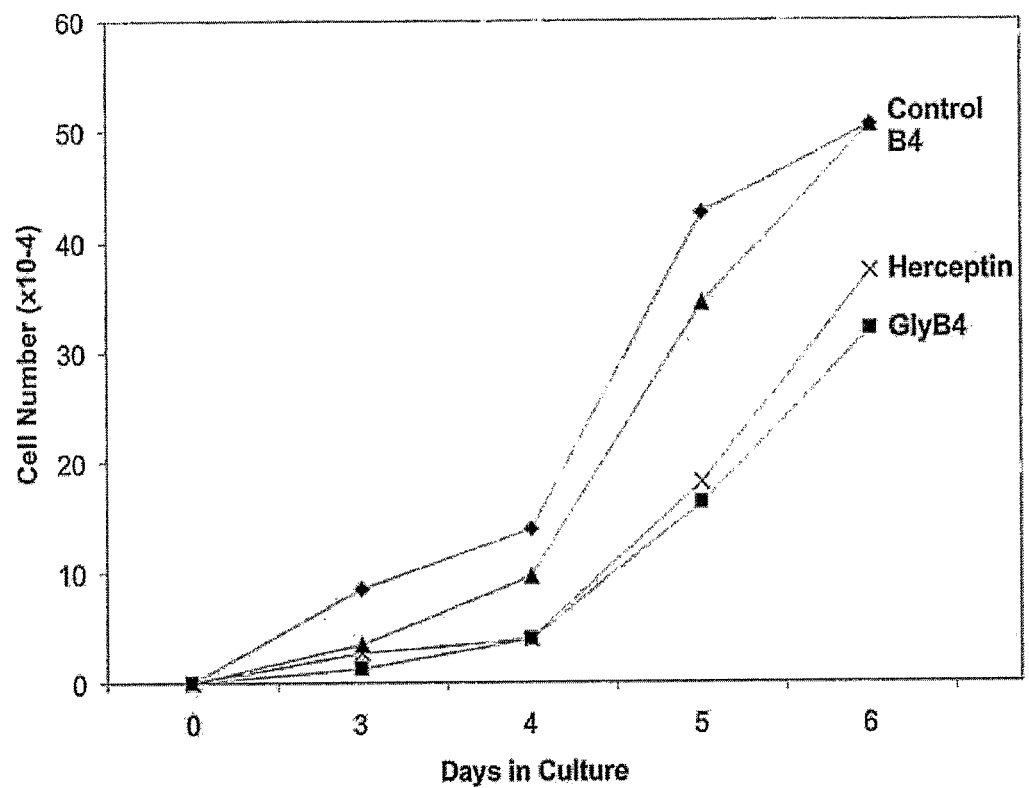
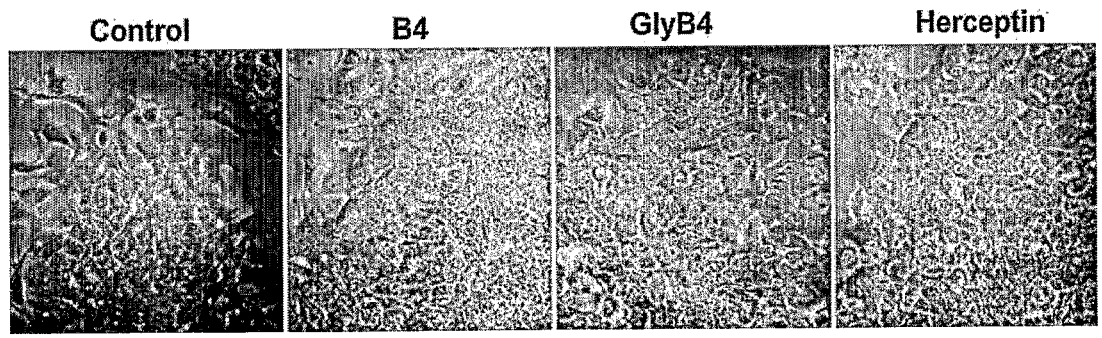
Fig. 5D

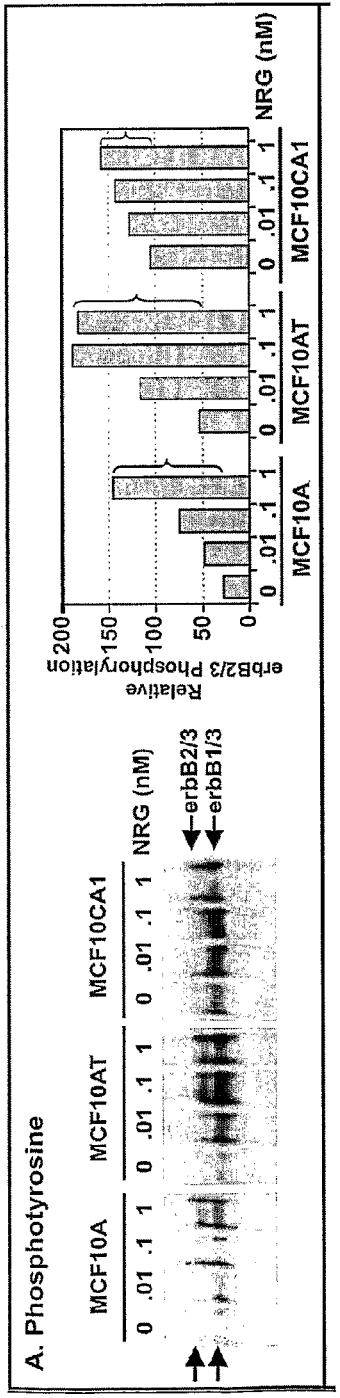
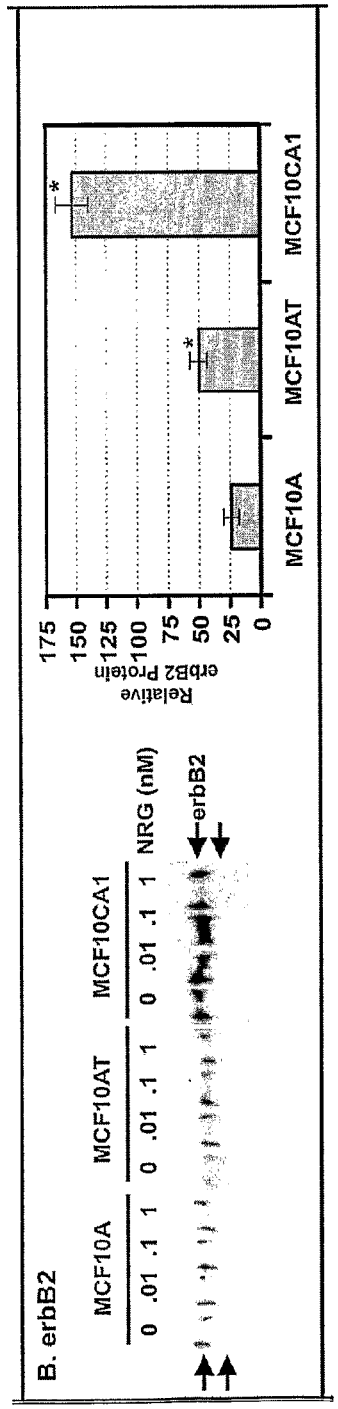
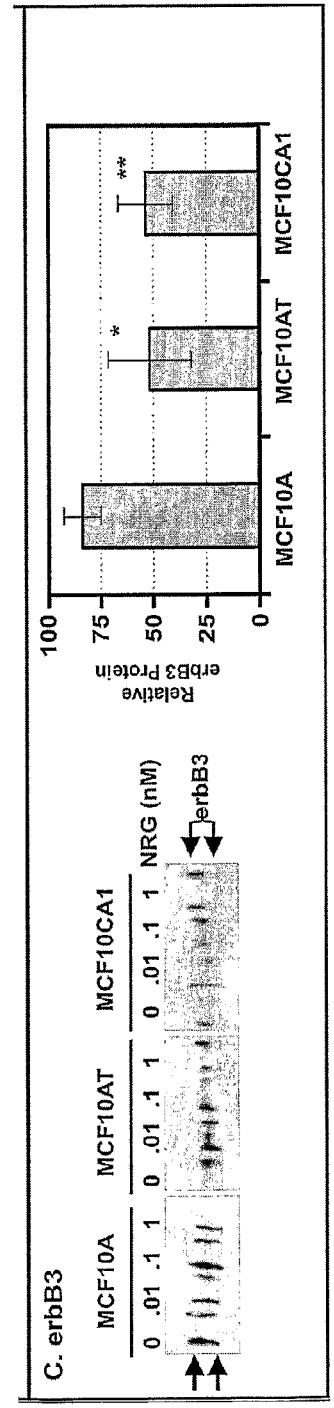

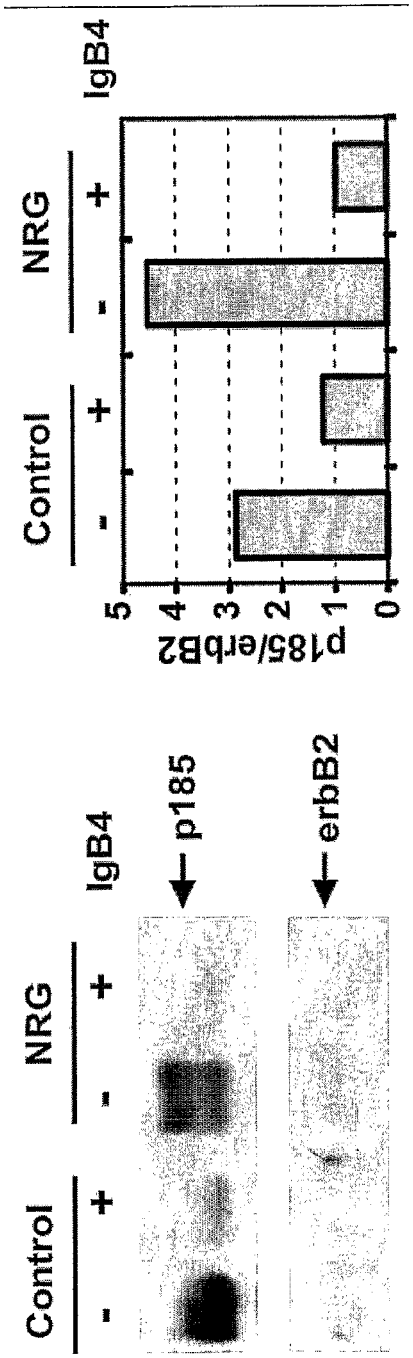
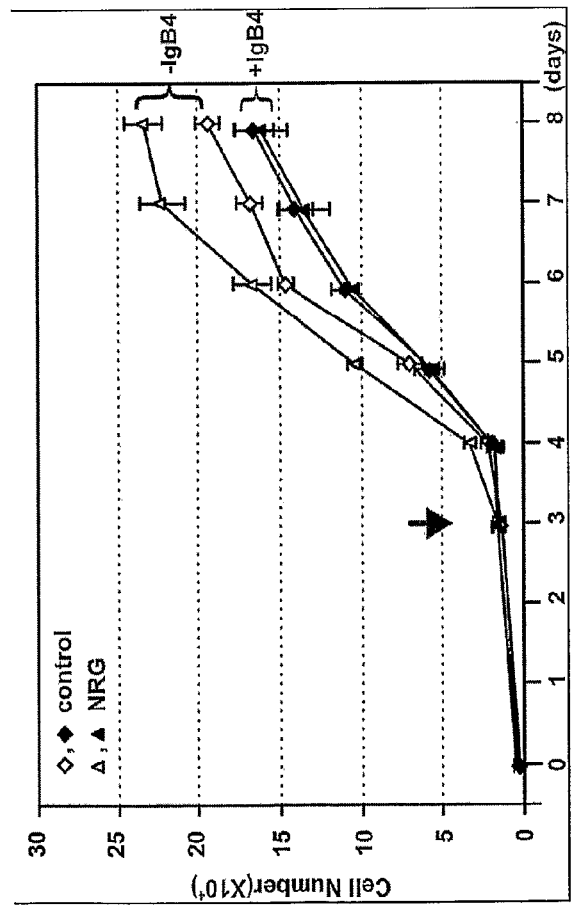
Fig. 10A
Fig. 10B
Fig. 10C

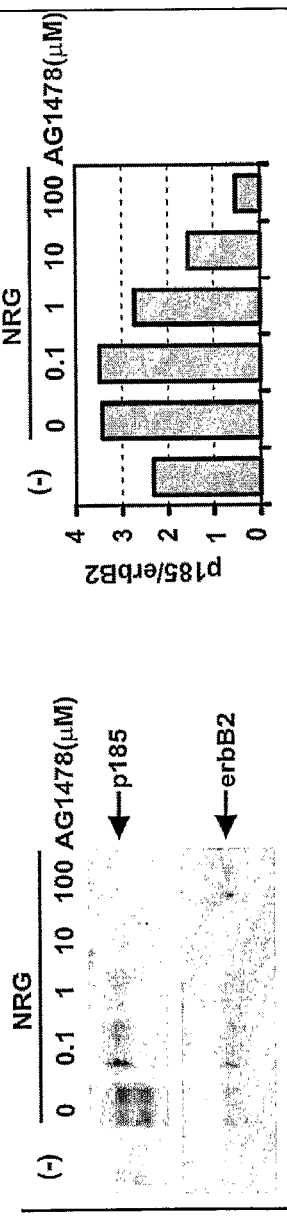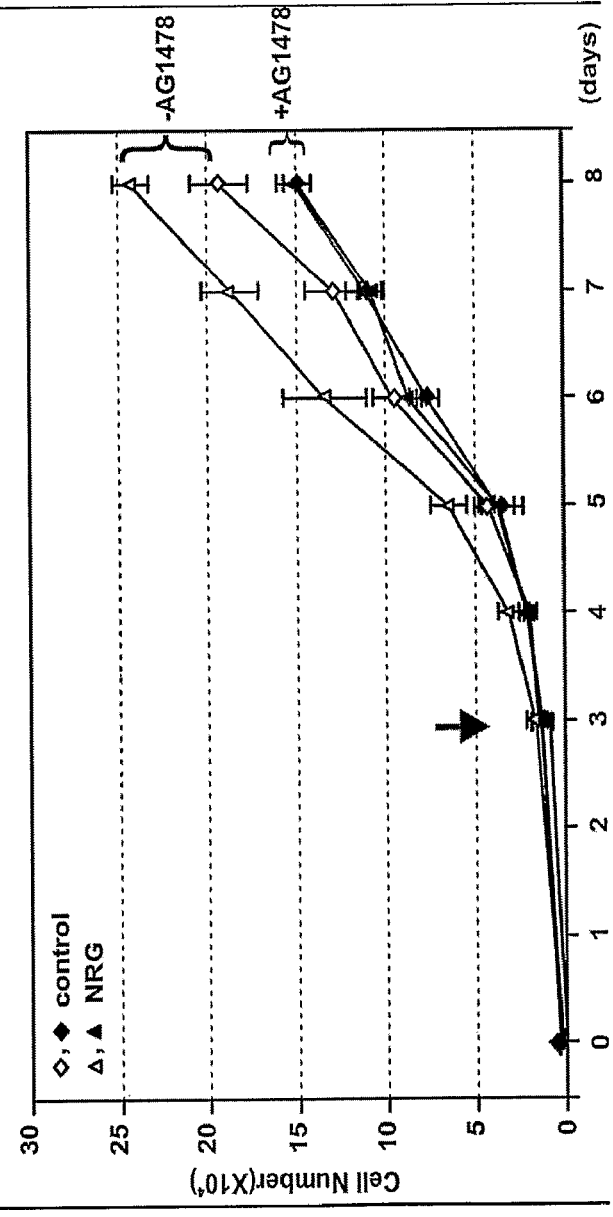

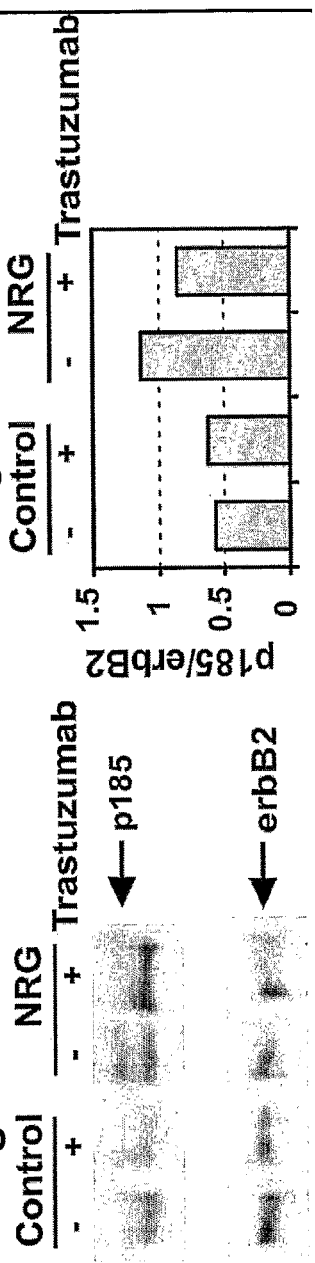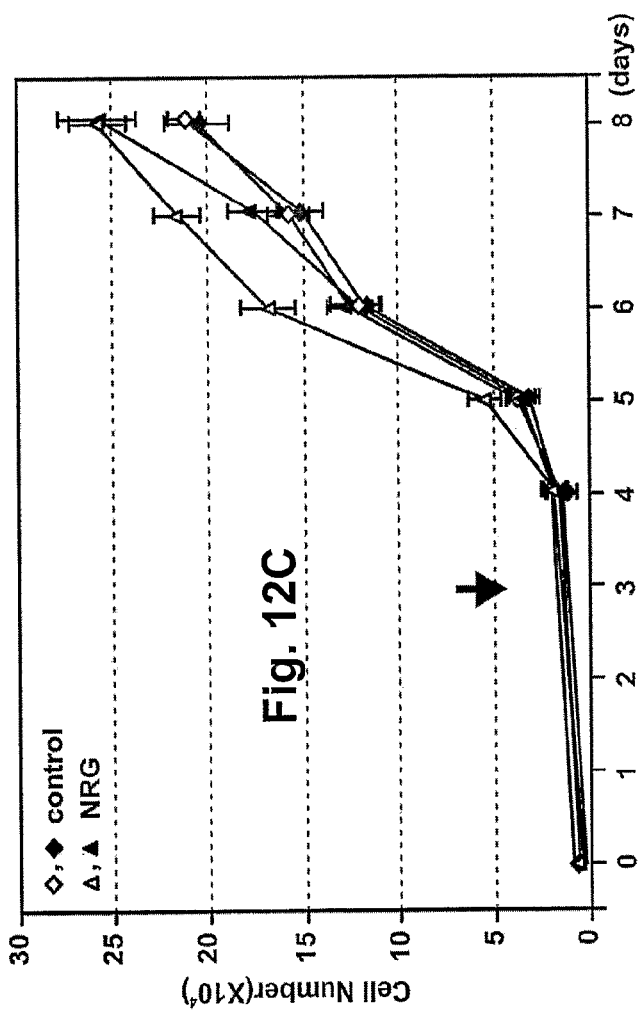

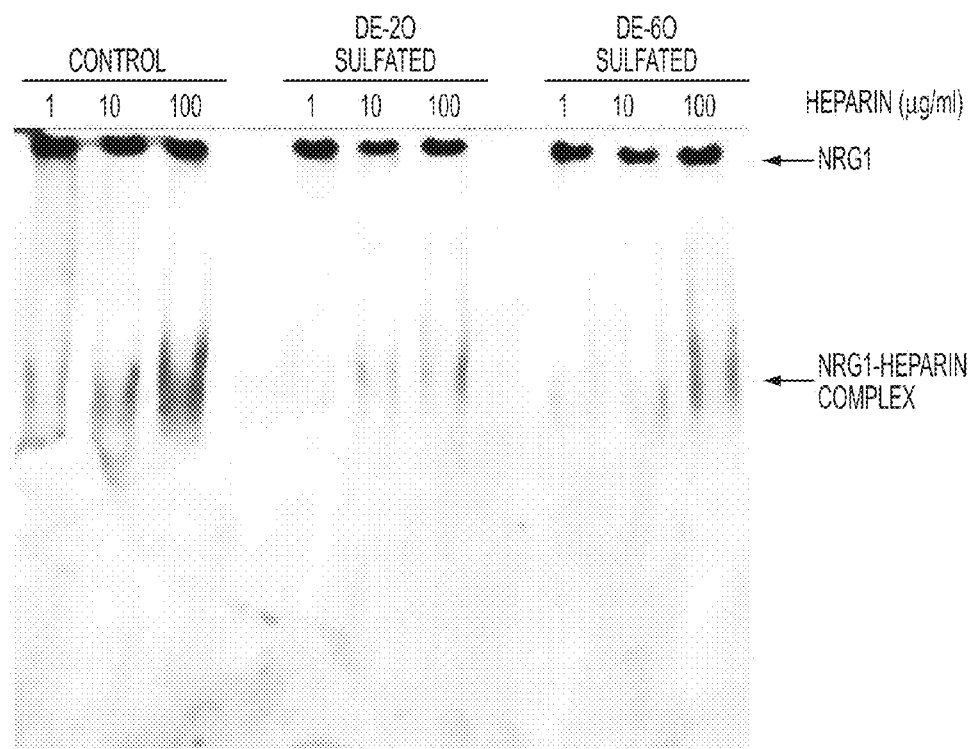
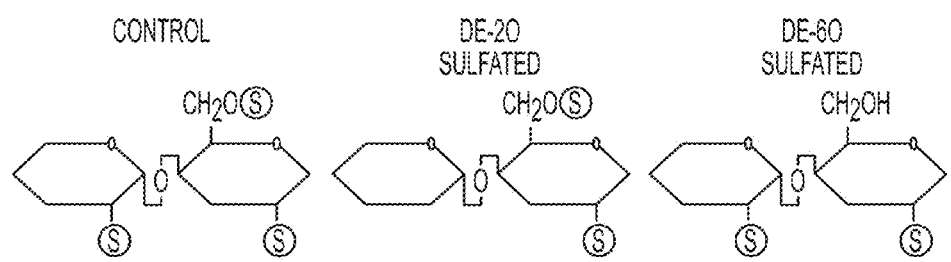
FIG. 15B

SEQUENCE LISTING

<160> NUMBER OF SEQ ID NOS: 38

<210> SEQ ID NO 1
<211> LENGTH: 70
<212> TYPE: PRT
<213> ORGANISM: Homo sapiens

<400> SEQUENCE: 1

Gly Ser Lys Leu Val Leu Arg Cys Glu Thr Ser Ser Glu Tyr Ser Ser
1               5                   10                  15

Leu Arg Phe Lys Trp Phe Lys Asn Gly Asn Glu Leu Asn Arg Lys Asn
                20                  25                  30

Lys Pro Gln Asn Ile Lys Ile Gln Lys Lys Pro Gly Lys Ser Glu Leu
            35                  40                  45

Arg Ile Asn Lys Ala Ser Leu Ala Asp Ser Gly Glu Tyr Met Cys Lys
    50                  55                  60

Val Ile Ser Lys Leu Gly
65                  70

<210> SEQ ID NO 2
<211> LENGTH: 70
<212> TYPE: PRT
<213> ORGANISM: Rattus sp.

<400> SEQUENCE: 2

```
Gly Ser Lys Leu Val Leu Arg Cys Glu Thr Ser Ser Glu Tyr Ser Ser
1               5                   10                  15

Leu Arg Phe Lys Trp Phe Lys Asn Gly Asn Glu Leu Asn Arg Lys Asn
            20                  25                  30

Lys Pro Glu Asn Ile Lys Ile Gln Lys Lys Pro Gly Lys Ser Glu Leu
                35                  40                  45

Arg Ile Asn Lys Ala Ser Leu Ala Asp Ser Gly Glu Tyr Met Cys Lys
        50                  55                  60

Val Ile Ser Lys Leu Gly
65                  70

<210> SEQ ID NO 3
<211> LENGTH: 70
<212> TYPE: PRT
<213> ORGANISM: Avian sp.

<400> SEQUENCE: 3

Gly Gln Lys Leu Val Leu Arg Cys Glu Thr Thr Ser Glu Tyr Pro Ala
1               5                   10                  15

Leu Arg Lys Trp Leu Lys Asn Gly Lys Glu Ile Thr Lys Lys Asn Arg
            20                  25                  30

Pro Glu Asn Val Lys Ile Pro Lys Gln Lys Lys Tyr Ser Glu Leu
                35                  40                  45

His Ile Tyr Arg Ala Thr Leu Ala Asp Ala Gly Glu Tyr Ala Cys Arg
        50                  55                  60

Val Ser Ser Lys Leu Gly
65                  70

<210> SEQ ID NO 4
<211> LENGTH: 210
<212> TYPE: DNA
<213> ORGANISM: Homo sapiens

<400> SEQUENCE: 4
ggttccaaac tagtccttcg gtgtgaaacc agttctgaat actcctctct cagattcaag      60
tggttcaaga atgggaatga attgaatcga aaaaacaaac cacaaaatat caagatacaa     120
aaaaagccag ggaagtcaga acttcgcatt aacaaagcat cactggctga ttctggagag     180
tatatgtgca aagtgatcag caaattagga                                      210

<210> SEQ ID NO 5
<211> LENGTH: 210
<212> TYPE: DNA
<213> ORGANISM: Rattus sp.

<400> SEQUENCE: 5
ggctccaagc tagtgctccg gtgcgaaacc agctccgagt actcctcact cagattcaaa      60
tggttcaaga atgggaacga gctgaaccgc aaaaataaac cagaaaacat caagatacag     120
aacaagccag ggaagtcaga gcttcgaatt aacaaagcat ccctggctga ctctggagag     180
tatatgtgca aagtgatcag caagttagga                                      210

<210> SEQ ID NO 6
<211> LENGTH: 213
<212> TYPE: DNA
<213> ORGANISM: Avian sp.

<400> SEQUENCE: 6
ggtcagaagc tagtgctaag gtgtgaaacc acttcagagt accctgcgct cagattcaaa      60
```

-continued

```
tggttaaaga acgggaagga aataacgaaa aaaaacagac ccgaaaatgt caagatcccc      120
aaaaagcaaa agaaatactc tgagcttcat atttatagag ccacgttggc tgacgctggg      180
gaatacgcat gcagagtgag cagcaaacta ggg                                  213
```

```
<210> SEQ ID NO 7
<211> LENGTH: 26
<212> TYPE: PRT
<213> ORGANISM: Homo sapiens

<400> SEQUENCE: 7

Lys Trp Phe Lys Asn Gly Asn Glu Leu Asn Arg Lys Asn Lys Pro Gln
1               5                   10                  15

Asn Ile Lys Ile Gln Lys Lys Pro Gly Lys
            20                  25

<210> SEQ ID NO 8
<211> LENGTH: 26
<212> TYPE: PRT
<213> ORGANISM: Rattus sp.

<400> SEQUENCE: 8

Lys Trp Phe Lys Asn Gly Asn Glu Leu Asn Arg Lys Asn Lys Pro Glu
1               5                   10                  15

Asn Ile Lys Ile Gln Lys Lys Pro Gly Lys
            20                  25

<210> SEQ ID NO 9
<211> LENGTH: 26
<212> TYPE: PRT
<213> ORGANISM: Avian sp.

<400> SEQUENCE: 9

Lys Trp Leu Lys Asn Gly Lys Glu Ile Thr Lys Lys Asn Arg Pro Glu
1               5                   10                  15

Asn Val Lys Ile Pro Lys Lys Gln Lys Lys
            20                  25

<210> SEQ ID NO 10
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(10)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid
<220> FEATURE:
<221> NAME/KEY: MISC_FEATURE
<222> LOCATION: (15)..(17)
<223> OTHER INFORMATION: Xaa can be any amino acid
<220> FEATURE:
<221> NAME/KEY: MISC_FEATURE
<222> LOCATION: (19)..(20)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: Xaa can be any amino acid
```

```
<400> SEQUENCE: 10

Lys Xaa Xaa Lys Xaa Xaa Xaa Xaa Xaa Arg Lys Xaa Lys Xaa Xaa
1               5                   10                  15

Xaa Lys Xaa Xaa Lys Lys Xaa Xaa Lys
            20                  25

<210> SEQ ID NO 11
<211> LENGTH: 6
<212> TYPE: PRT
<213> ORGANISM: Artificial sequence
<220> FEATURE:
<223> OTHER INFORMATION: Linker for fusion peptide

<400> SEQUENCE: 11

Val Pro Arg Gly Ser Asp
1               5

<210> SEQ ID NO 12
<211> LENGTH: 6
<212> TYPE: PRT
<213> ORGANISM: Artificial sequence
<220> FEATURE:
<223> OTHER INFORMATION: Linker for fusion peptide

<400> SEQUENCE: 12

Asp Asp Lys Asp Trp His
1               5

<210> SEQ ID NO 13
<211> LENGTH: 2463
<212> TYPE: DNA
<213> ORGANISM: Artificial sequence
<220> FEATURE:
<223> OTHER INFORMATION: Synthetic sequence

<400> SEQUENCE: 13
atgaagccgg cgacaggact ttgggtctgg gtgagccttc tcgtggcggc ggggaccgtc      60
cagcccagcg attctcagtc aggtaccaag aagaaggagc gaggctccgg caagaagccg     120
gagtccgcgg cgggcagcca gagcccagcc ttgcctcccc gattgaaaga gatgaaaagc     180
caggaatcgg ctgcaggttc caaactagtc cttcggtgtg aaaccagttc tgaatactcc     240
tctctcagat tcaagtggtt caagaatggg aatgaattga atcgaaaaaa caaaccacaa     300
aatatcaaga tacaaaaaaa gccagggaag tcagaacttc gcattaacaa agcatcactg     360
gctgattctg gagagtatat gtgcaaagtg atcagcaaat taggaaatga cagtgcctct     420
gccaatatca ccatcgtgga atcaaacgag atcatcactg gtatgccagc ctcaactgaa     480
ggagcatatg tgtcttcaga gtctcccatt agaatatcag tatccacaga aggagcaaat     540
acttcttcat ctacatctac atccaccact gggacaagcg gtacccagtc agtgtgtgca     600
ggaacggaga ataaactgag ctctctctct gacctggaac agcagtaccg agccttgcgc     660
aagtactatg aaaactgtga ggttgtcatg ggcaacctgg agataaccag cattgagcac     720
aaccgggacc tctccttcct gcggtctgtt cgagaagtca caggctacgt gttagtggct     780
cttaatcagt ttcgttacct gcctctggag aatttacgca ttattcgtgg gacaaaactt     840
tatgaggatc gatatgcctt ggcaatattt ttaaactaca aaaagatgg aaactttgga     900 cttcaagaac ttggattaaa gaacttgaca gaaatcctaa atggtggagt ctatgtagac     960
cagaacaaat tcctttgtta tgcagacacc attcattggc aagatattgt tcggaaccca    1020
tggccttcca acttgactct tgtgtcaaca atggtagtt caggatgtgg acgttgccat    1080
```

```
aagtcctgta ctggccgttg ctggggaccc acagaaaatc attgccgagac tttgacaagg   1140 acggtgtgtg cagaacaatg tgacggcaga tgctacggac cttacgtcag tgactgctgc   1200
catcgagaat gtgctggagg ctgctcagga cctaaggaca cagactgctt tgcctgcatg   1260
aatttcaatg acagtggagc atgtgttact cagtgtcccc aaacctttgt ctacaatcca   1320
accacctttc aactggagca caatttcaat gcaaagtaca catatggagc attctgtgtc   1380
aagaaatgtc cacataactt tgtggtagat tccagttctt gtgtgcgtgc ctgccctagt   1440
tccaagatgg aagtagaaga aaatgggatt aaaatgtgta aaccttgcac tgacatttgc   1500
ccaaaagctt gtgatggcat tggcacagga tcattgatgt cagctcagac tgtggattcc   1560
agtaacattg acaaattcat aaactgtacc aagatcaatg ggaatttgat ctttctagtc   1620
actggtattc atggggaccc ttacaatgca attgaagcca tagacccaga gaaactgaac   1680
gtctttcgga cagtcagaga gataacaggt ttcctgaaca tacagtcatg gccaccaaac   1740
atgactgact tcagtgtttt ttctaacctg gtgaccattg gtggaagagt actctatagt   1800
ggcctgtcct tgcttatcct caagcaacag ggcatcacct ctctacagtt ccagtccctg   1860
aaggaaatca gcgcaggaaa catctatatt actgacaaca gcaacctgtg ttattatcat   1920
accattaact ggacaacact cttcagcaca atcaaccaga gaatagtaat ccgggacaac   1980
agaaaagctg aaaattgtac tgctgaagga atggtgtgca accatctgtg ttccagtgat   2040
ggctgbttgg ggacctgggc cagaccaatg tctgtcgtgt cgccgcttca gtagaggaag   2100
gatctgcata gagtcttgta acctctatga tggtgaattt cgggagtttg agaatggctc   2160
catctgtgtg gagtgtgacc cccagtgtga aagatggaa gatggcctcc tcacatgcca   2220
tggaccgggt cctgacaact gtacaaagtg ctctcatttt aaagatggcc caaactgtgt   2280
ggaaaaatgt ccagatggct tacagggggc aaacagtttc attttcaagt atgctgatcc   2340
agatcgggag tgccacccat gccatccaaa ctgcacccaa gggtgtaacg gtcccactag   2400
tcatgactgc atttactacc catggacggg ccattccact ttaccacaac atgctaagaa   2460
ttc                                                                 2463
```

<210> SEQ ID NO 14
<211> LENGTH: 822
<212> TYPE: PRT
<213> ORGANISM: Artificial sequence
<220> FEATURE:
<223> OTHER INFORMATION: Synthetic sequence

<400> SEQUENCE: 14

```
Gln Lys Met Lys Pro Ala Thr Gly Leu Trp Val Trp Val Ser Leu Leu
1               5                   10                  15

Val Ala Ala Gly Thr Val Gln Pro Ser Asp Ser Gln Ser Gly Tyr Lys
            20                  25                  30

Lys Lys Glu Arg Gly Ser Gly Lys Lys Pro Glu Ser Ala Ala Gly Ser
        35                  40                  45

Gln Ser Pro Ala Leu Pro Pro Arg Leu Lys Glu Met Lys Ser Gln Glu
    50                  55                  60

Ser Ala Ala Gly Ser Lys Leu Val Leu Arg Cys Glu Thr Ser Ser Glu
65                  70                  75                  80

Tyr Ser Ser Leu Arg Phe Lys Trp Phe Lys Asn Gly Asn Glu Leu Asn
                85                  90                  95

Arg Lys Asn Lys Pro Gln Asn Ile Lys Ile Gln Lys Lys Pro Gly Lys
            100                 105                 110
```

```
Ser Glu Leu Arg Ile Asn Lys Ala Ser Leu Ala Asp Ser Gly Glu Tyr
        115                 120                 125

Met Cys Lys Val Ile Ser Lys Leu Gly Asn Asp Ser Ala Ser Ala Asn
130                 135                 140

Ile Thr Ile Val Glu Ser Asn Glu Ile Ile Thr Gly Met Pro Ala Ser
145                 150                 155                 160

Thr Glu Gly Ala Tyr Val Ser Ser Glu Ser Pro Ile Arg Ile Ser Val
                165                 170                 175

Ser Thr Glu Gly Ala Asn Thr Ser Ser Ser Thr Ser Thr Thr
            180                 185                 190

Gly Thr Ser Gly Thr Gln Ser Val Cys Ala Gly Thr Glu Asn Lys Leu
        195                 200                 205

Ser Ser Leu Ser Asp Leu Glu Gln Gln Tyr Arg Ala Leu Arg Lys Tyr
210                 215                 220

Tyr Glu Asn Cys Glu Val Val Met Gly Asn Leu Glu Ile Thr Ser Ile
225                 230                 235                 240

Glu His Asn Arg Asp Leu Ser Phe Leu Arg Ser Val Arg Glu Val Thr
                245                 250                 255

Gly Tyr Val Leu Val Ala Leu Asn Gln Phe Arg Tyr Leu Pro Leu Glu
        260                 265                 270

Asn Leu Arg Ile Ile Arg Gly Thr Lys Leu Tyr Glu Asp Arg Tyr Ala
        275                 280                 285

Leu Ala Ile Phe Leu Asn Tyr Arg Lys Asp Gly Asn Phe Gly Leu Gln
        290                 295                 300

Glu Leu Gly Leu Lys Asn Leu Thr Glu Ile Leu Asn Gly Gly Val Tyr
305                 310                 315                 320

Val Asp Gln Asn Lys Phe Leu Cys Tyr Ala Asp Thr Ile His Trp Gln
                325                 330                 335

Asp Ile Val Arg Asn Pro Trp Pro Ser Asn Leu Thr Leu Val Ser Thr
            340                 345                 350

Asn Gly Ser Ser Gly Cys Gly Arg Cys His Lys Ser Cys Thr Gly Arg
        355                 360                 365

Cys Trp Gly Pro Thr Glu Asn His Cys Gln Thr Leu Thr Arg Thr Val
370                 375                 380

Cys Ala Glu Gln Cys Asp Gly Arg Cys Tyr Gly Pro Tyr Val Ser Asp
385                 390                 395                 400

Cys Cys His Arg Glu Cys Ala Gly Gly Cys Ser Gly Pro Lys Asp Thr
                405                 410                 415

Asp Cys Phe Ala Cys Met Asn Phe Asn Asp Ser Gly Ala Cys Val Thr
        420                 425                 430

Gln Cys Pro Gln Thr Phe Val Tyr Asn Pro Thr Thr Phe Gln Leu Glu
        435                 440                 445

His Asn Phe Asn Ala Lys Tyr Thr Tyr Gly Ala Phe Cys Val Lys Lys
        450                 455                 460

Cys Pro His Asn Phe Val Val Asp Ser Ser Ser Cys Val Arg Ala Cys
465                 470                 475                 480

Pro Ser Ser Lys Met Glu Val Glu Glu Asn Gly Ile Lys Met Cys Lys
                485                 490                 495

Pro Cys Thr Asp Ile Cys Pro Lys Ala Cys Asp Gly Ile Gly Thr Gly
            500                 505                 510

Ser Leu Met Ser Ala Gln Thr Val Asp Ser Ser Asn Ile Asp Lys Phe
        515                 520                 525

Ile Asn Cys Thr Lys Ile Asn Gly Asn Leu Ile Phe Leu Val Thr Gly
        530                 535                 540
```

-continued

Ile His Gly Asp Pro Tyr Asn Ala Ile Glu Ala Ile Asp Pro Glu Lys
545                 550                 555                 560

Leu Asn Val Phe Arg Thr Val Arg Glu Ile Thr Gly Phe Leu Asn Ile
            565                 570                 575

Gln Ser Trp Pro Pro Asn Met Thr Asp Phe Ser Val Phe Ser Asn Leu
        580                 585                 590

Val Thr Ile Gly Gly Arg Val Leu Tyr Ser Gly Leu Ser Leu Leu Ile
            595                 600                 605

Leu Lys Gln Gln Gly Ile Thr Ser Leu Gln Phe Gln Ser Leu Lys Glu
        610                 615                 620

Ile Ser Ala Gly Asn Ile Tyr Ile Thr Asp Asn Ser Asn Leu Cys Tyr
625                 630                 635                 640

Tyr His Thr Ile Asn Trp Thr Thr Leu Phe Ser Thr Ile Asn Gln Arg
            645                 650                 655

Ile Val Ile Arg Asp Asn Arg Lys Ala Glu Asn Cys Thr Ala Glu Gly
            660                 665                 670

Met Val Cys Asn His Leu Cys Ser Ser Asp Gly Cys Trp Gly Pro Gly
            675                 680                 685

Pro Asp Gln Cys Leu Ser Cys Arg Arg Phe Ser Arg Gly Arg Ile Cys
690                 695                 700

Ile Glu Ser Cys Asn Leu Tyr Asp Gly Glu Phe Arg Glu Phe Glu Asn
705                 710                 715                 720

Gly Ser Ile Cys Val Glu Cys Asp Pro Gln Cys Glu Lys Met Glu Asp
            725                 730                 735

Gly Leu Leu Thr Cys His Gly Pro Gly Pro Asp Asn Cys Thr Lys Cys
            740                 745                 750

Ser His Phe Lys Asp Gly Pro Asn Cys Val Glu Lys Cys Pro Asp Gly
            755                 760                 765

Leu Gln Gly Ala Asn Ser Phe Ile Phe Lys Tyr Ala Asp Pro Asp Arg
        770                 775                 780

Glu Cys His Pro Cys His Pro Asn Cys Thr Gln Gly Cys Asn Gly Pro
785                 790                 795                 800

Thr Ser His Asp Cys Ile Tyr Tyr Pro Trp Thr Gly His Ser Thr Leu
            805                 810                 815

Pro Gln His Ala Lys Asn
            820

<210> SEQ ID NO 15
<211> LENGTH: 32
<212> TYPE: DNA
<213> ORGANISM: Unknown
<220> FEATURE:
<223> OTHER INFORMATION: primer

<400> SEQUENCE: 15
cttgggtacc caaaaaatga agccggcgac ag                                    32

<210> SEQ ID NO 16
<211> LENGTH: 31
<212> TYPE: DNA
<213> ORGANISM: Unknown
<220> FEATURE:
<223> OTHER INFORMATION: primer

<400> SEQUENCE: 16
cgcgaattct tagcatgttg tggtaaagtg g                                     31

```
<210> SEQ ID NO 17
<211> LENGTH: 32
<212> TYPE: DNA
<213> ORGANISM: Unknown
<220> FEATURE:
<223> OTHER INFORMATION: primer

<400> SEQUENCE: 17
cttgggtacc caaaaaatga agccggcgac ag                              32

<210> SEQ ID NO 18
<211> LENGTH: 32
<212> TYPE: DNA
<213> ORGANISM: Unknown
<220> FEATURE:
<223> OTHER INFORMATION: primer

<400> SEQUENCE: 18
ccgcgaattc actcatttac ccggagacag gg                              32

<210> SEQ ID NO 19
<211> LENGTH: 31
<212> TYPE: DNA
<213> ORGANISM: Unknown
<220> FEATURE:
<223> OTHER INFORMATION: primer

<400> SEQUENCE: 19
caggatccca agaagaagga gcgaggcctc c                               31

<210> SEQ ID NO 20
<211> LENGTH: 30
<212> TYPE: DNA
<213> ORGANISM: Unknown
<220> FEATURE:
<223> OTHER INFORMATION: primer

<400> SEQUENCE: 20
gcgaattccc taatttgctg atcactttgc                                 30

<210> SEQ ID NO 21
<211> LENGTH: 32
<212> TYPE: DNA
<213> ORGANISM: Unknown
<220> FEATURE:
<223> OTHER INFORMATION: primer

<400> SEQUENCE: 21
gccaagcttg caaaaaatga agccggcgac ag                              32

<210> SEQ ID NO 22
<211> LENGTH: 30
<212> TYPE: DNA
<213> ORGANISM: Unknown
<220> FEATURE:
<223> OTHER INFORMATION: primer

<400> SEQUENCE: 22
gaggtaccct gagaatcgct gggctggacg                                 30

<210> SEQ ID NO 23
<211> LENGTH: 30
<212> TYPE: DNA
<213> ORGANISM: Unknown
<220> FEATURE:
<223> OTHER INFORMATION: primer

<400> SEQUENCE: 23
```
ttgggtaccc agtcagtgtg tgcaggaacg                                30

<210> SEQ ID NO 24
<211> LENGTH: 31
<212> TYPE: DNA
<213> ORGANISM: Unknown
<220> FEATURE:
<223> OTHER INFORMATION: primer

<400> SEQUENCE: 24
cgcgaattct tagcatgttg tggtaaagtg g                              31

<210> SEQ ID NO 25
<211> LENGTH: 30
<212> TYPE: DNA
<213> ORGANISM: Unknown
<220> FEATURE:
<223> OTHER INFORMATION: primer

<400> SEQUENCE: 25
tgggtaccaa gaagaaggag cgaggctccg                                30

<210> SEQ ID NO 26
<211> LENGTH: 31
<212> TYPE: DNA
<213> ORGANISM: Unknown
<220> FEATURE:
<223> OTHER INFORMATION: primer

<400> SEQUENCE: 26
gaggtacctc ctaatttgct tatcactttg c                              31

<210> SEQ ID NO 27
<211> LENGTH: 30
<212> TYPE: DNA
<213> ORGANISM: Unknown
<220> FEATURE:
<223> OTHER INFORMATION: primer

<400> SEQUENCE: 27
tgggtaccaa gaagaaggag cgaggctccg                                30

<210> SEQ ID NO 28
<211> LENGTH: 31
<212> TYPE: DNA
<213> ORGANISM: Unknown
<220> FEATURE:
<223> OTHER INFORMATION: primer

<400> SEQUENCE: 28
gaggtaccgc ttgtcccagt ggtggatgta g                              31

<210> SEQ ID NO 29
<211> LENGTH: 27
<212> TYPE: DNA
<213> ORGANISM: Unknown
<220> FEATURE:
<223> OTHER INFORMATION: primer

<400> SEQUENCE: 29
caggatccca agaaggagcg aggctcc                                   27

<210> SEQ ID NO 30
<211> LENGTH: 29
<212> TYPE: DNA
<213> ORGANISM: Unknown

```
<220> FEATURE:
<223> OTHER INFORMATION: primer

<400> SEQUENCE: 30
cgggatccct aatttgctga tcactttgc                                          29

<210> SEQ ID NO 31
<211> LENGTH: 21
<212> TYPE: DNA
<213> ORGANISM: Unknown
<220> FEATURE:
<223> OTHER INFORMATION: primer

<400> SEQUENCE: 31
gaggacaaac gccacaaaga c                                                  21

<210> SEQ ID NO 32
<211> LENGTH: 19
<212> TYPE: DNA
<213> ORGANISM: Unknown
<220> FEATURE:
<223> OTHER INFORMATION: primer

<400> SEQUENCE: 32
gggctgtggt gcctgtttt                                                     19

<210> SEQ ID NO 33
<211> LENGTH: 20
<212> TYPE: DNA
<213> ORGANISM: Unknown
<220> FEATURE:
<223> OTHER INFORMATION: primer

<400> SEQUENCE: 33
ccagctccga gacctttgag                                                    20

<210> SEQ ID NO 34
<211> LENGTH: 22
<212> TYPE: DNA
<213> ORGANISM: Unknown
<220> FEATURE:
<223> OTHER INFORMATION: primer

<400> SEQUENCE: 34
gtgttggagg gaatagggaa ga                                                 22

<210> SEQ ID NO 35
<211> LENGTH: 23
<212> TYPE: DNA
<213> ORGANISM: Unknown
<220> FEATURE:
<223> OTHER INFORMATION: primer

<400> SEQUENCE: 35
aaagtgatgg acacagtgca gaa                                                23

<210> SEQ ID NO 36
<211> LENGTH: 20
<212> TYPE: DNA
<213> ORGANISM: Unknown
<220> FEATURE:
<223> OTHER INFORMATION: primer

<400> SEQUENCE: 36
gctggcacca aaatcctttc                                                    20
```

-continued

```
<210> SEQ ID NO 37
<211> LENGTH: 24
<212> TYPE: DNA
<213> ORGANISM: Unknown
<220> FEATURE:
<223> OTHER INFORMATION: primer

<400> SEQUENCE: 37
agtatgactc tacccacggc aagt                                            24

<210> SEQ ID NO 38
<211> LENGTH: 20
<212> TYPE: DNA
<213> ORGANISM: Unknown
<220> FEATURE:
<223> OTHER INFORMATION: primer

<400> SEQUENCE: 38
tctcgctcct ggaagatggt                                                 20
```

HYBRID PROTEINS WITH ERBB4 EXTRACELLULAR DOMAIN AND NEUREGULIN HEPARIN-BINDING DOMAIN FOR TARGETING

BACKGROUND OF THE INVENTION

1. Field of the Invention

The invention in the fields of biochemistry, neuroscience and medicine, relates to compositions and methods based on hybrid polypeptides including the neuregulin heparin binding domain (N-BBD) and erbB4 extracellular domain to target polypeptides to cell surfaces and to extracellular matrix rich in heparan sulfate proteoglycans (HSPGs) for the treatment of various diseases, particularly cancer.

2. Description of the Background Art

To carry out their diverse physiological functions, cells must adhere in a specific manner to cellular and extracellular components of their environment. Cells' ability to recognize multiple environmental cues and undergo specific adhesive reactions is critical to complex cellular functions. Recognition and adhesion are mediated by cell adhesion molecules ("CAMs") which bind to macromolecules expressed on neighboring cells or in the extracellular matrix ("ECM").

Three motifs present in adhesion molecules for which 3D structure is known are immunoglobulin (Ig) superfamily domains, fibronectin type III (Fn-III) domains and cadherin the domains. In the nervous system, Ig superfamily members mediate Ca-independent homophilic and heterophilic binding. The extracellular regions of these molecules include one or more domains ("extracellular domains" or "ECDs") with sequence similarity to variable (V) or constant (C) domains of Ig's (Williams, A F et al., *Annu. Rev. Immunol.* 6:381-405 (1988). Yoshihara, Y et al., *Neurosci. Res.* 10:83-105 (1991). Many Ig superfamily molecules consist of tandem Ig-like domains linked in series with multiple copies of a second building block domain (e.g., an Fn-III repeat). Because two molecules that share detectable sequence similarity adopt the same folding topology, investigators have used structures of molecules discovered in studies of the immune system as "first order" models for the structures of Ig domains in neural CAMs. Ig-like domains, and their topology are reviewed in Vaughn D E et al., *Neuron* 16:261-273 (1998). Ig V domains, the prototype of the V-like domains of CAMs, are folded similarly; they are found in antibody $V_H$ and $V_L$ domains and the N-terminal domains of the T cell receptor (TCR) α and β chains, the T cell surface molecule CD4 (first and third domains) and CD8, the N-terminal domains of the "immune system CAM" CD2, vascular cell adhesion molecule-1 (VCAM-1) and telokin, and the C-terminal domain of the myosin light chain kinase. Ig C1 domains consist of seven β strands arranged into two antiparallel sheets. The two sheets are connected by a disulfide bond between strands "B" and "F." In an antibody, constant domains are found in the Fc regions and the C-terminal domains of the Fab Ig fragment. Constant-like or C1 set domains, are also found in the membrane proximal domains of MHC molecules and TCRs. The C2 and C1 folding topologies are similar. C2 domains are present in three Ig superfamily members: CD2, the second domain of VCAM-1 and the second and fourth domains of CD4. The heparin binding domain (HBD) of neuregulin, a focus of the present invention, is an Ig-C2 domain.

Important means of intercellular communication are growth and differentiation factors that are released from one cell and bind to and activate membrane receptors on a nearby cell, which ultimately changes its properties through changes in gene expression. Many released polypeptide factors have additional binding interactions with heparan-sulfate proteoglycans (HSPGs) situated in the ECM between cells. This dual-binding interaction may serve to concentrate these factors at sites where they are needed, to protect them from proteolysis, and to modulate their interactions with their receptors (Schlessinger, J et al. (1995) *Cell* 83:357-360). The understanding of how these extracellular interactions modulate the intracellular events that ultimately change a cell's properties are still evolving.

The neuregulins (NRGs) are a family of heparin-binding growth and differentiation factors with multiple functions in (a) growth and development of the nervous system and heart, and (b) cancer (Fischbach, G D et al. (1997) *Annu Rev Neurosci* 20:429-458). In one case, NRGs released from motor nerve endings at neuromuscular synapses activate members of the epidermal growth factor (EGF) family of tyrosine kinase receptors erbB2, erbB3 and erbB4 in the postsynaptic muscle membrane (Loeb, J A et al. (1999) *Development* 126: 781-791; Goodearl, A D et al. (1995) *J Cell Biol* 130: 423-1434). As discussed herein, NRGs are potent mitogens that are often released from certain tumor cells thus acting in an autocrine manner to activate the same family of receptors on the same tumor cells, resulting in enhanced proliferation and metastatic activity (Li Q et al. (2004) *Cancer Res* 64:7078-85).

A common feature of all NRGs is the epidermal growth factor-like (EGF-like) domain. This domain, even when expressed by itself, is sufficient for receptor binding and activation of homo- and heterodimers of erbB2, erbB3, and erbB4 receptors which are highly concentrated, for example, at the neuromuscular synapses in the postsynaptic muscle membrane (Altiok, N. et al. (1995) *EMBO J* 14: 4258-4266). Rapid autophosphorylation of the receptors' Tyr residues initiates a signaling cascade that translates the initial binding event into the induction of AChR genes (Corfas, G. et al. (1993) *Proc. Natl Acad Sci USA* 90, 1624-1628). This signaling cascade involves a number of signaling pathways including both the mitogen-activated protein (MAP) kinase pathway and phosphatidylinositol 3-kinase (PI3K) pathways (Si, J. et al. (1996) *J Biol Chem* 271:19752-19759; Tansey, M G et al. (1996) *J Cell Biol* 134, 465-476; Altiok, N et al. (1997) *EMBO J* 16:717-725).

Most spliced forms of NRG also have an immunoglobulin-like (IG-like) domain N-terminal to the EGF-like domain (FIG. 1). Because this domain is a heparin-binding domain ("HBD") it is referred to herein as the neuregulin HBD (or "N-HBD"). The terms "IG-like domain" (from NRG) and "N-HBD" are used interchangeably here.

The present inventor and others have shown that the N-HBD interacts with HSPGs and may lead to the deposition of NRGs in the ECM of neuromuscular synapses and within the central nervous system (CNS) (Loeb et al., supra; Loeb, J A et al. (1995) *J Cell Biol* 130, 127-135; Meier, T. et al. (1998) *J Cell Biol* 141, 715-726). In the developing nervous system, HSPGs may "direct" the accumulation of NRG forms that include the N-HBD to the basal lamina of developing neuromuscular synapses at key stages of development (Loeb et al., 1999, supra).

One distinguishing feature of NRG is the presence of distinct domains, separated by a glycosylated spacer region, for heparan sulfate binding and for receptor binding. Recognition of this fact led the present inventor to determine the direct effects of HSPG binding on receptor activation and gene activation.

Rio, C et al., *Neuron* 19:39-50 (1997) described a 27 amino acid peptide of chick NRG that corresponded to the HBD, which was produced only for use as an immunogen to produce an antiserum in rabbits. Loeb, J A et al., 1995, supra, speculated that immobilization of NRGs to the ECM might involve their Ig-like domains binding to HSPGs. This speculation was based indirectly on observations that heparin inhibited receptor tyrosine phosphorylation induced by recombinant NRGs.

Since NRGs bind to heparin, T. Meier et al. (*J Cell Biol*, 1998, 141:715-726) examined whether recombinant HRG (=NRG) cloned from a human cDNA library bound directly to the recombinant HSPG chick agrin by the negatively charged glycosaminoglycan (GAG) side chains as proposed by Loeb et al., supra. Indeed, the Ig-like domain mediated binding to these GAG chains. The Ig-like domain, but not the EGF-like domain, bound to agrin.

While there have been numerous disclosures of Ig-C regions or various parts of Ig molecules fused to other proteins for various purposes, these regions primarily are derived from true Ig molecules. The N-HBD described here has less than 40% homology or sequence similarity to these true Ig domains so as to be distinct structurally and functionally from those in the prior art. Examples of such disclosures include the following. U.S. Pat. Nos. 5,116,964 and 5,428,130 describe a ligand, completely distinct from the NRG-HBD neuregulin IG domain described herein, that was said to target active peptides to cell surfaces. However, such targeting is not directed to, nor specific for, heparan sulfates at the cell surfaces. U.S. Pat. No. 5,565,335 describes an "immunoadhesion" comprising a fusion protein in which a polypeptide making up the adhesion variable (V) region is fused at its C-terminus to the N-terminus of an Ig C region polypeptide.

U.S. Pat. No. 6,018,026 and U.S. Pat. No. 5,155,027 describe biologically active polypeptides (and their coding DNA), and, specifically, dimerized fusion products comprising a first and a second polypeptide chain, each of which comprises a non-Ig polypeptide and requires dimerization for biological activity, joined to a heterologous "dimerizing" protein. Also described is a polypeptide chain of the non-Ig polypeptide dimer, joined to at least one Ig H chain C region domain (any of $C_H1$-$C_H4$). The expressed, dimerized fusion polypeptide exhibits biological activity characteristic of the non-Ig polypeptide dimer.

U.S. Pat. No. 5,541,087 describes DNA encoding a fusion protein comprising a sequence encoding an Ig Fc region lacking at least the $C_H1$ domain, and a target protein sequence. U.S. Pat. No. 5,869,046 discloses a method for preparing a variant "polypeptide of interest" which is an Fab or a (Fab')$_2$ fragment, the Ig domain (or Ig-like domain) of which comprises at least one of a $C_H1$ or $C_L$ region. U.S. Pat. No. 6,121,022 discloses a modified polypeptide having an Ig C domain or an Ig-like C domain and an epitope that binds to a salvage receptor within the Ig- or Ig-like C domain. This epitope, absent from the unmodified polypeptide, is taken from two loops of the $C_H2$ domain of an Ig Fc region. The Ig-like domains described in these documents are clearly distinct from the N-HBD of the present invention.

U.S. Pat. No. 6,121,415 describes a family of polypeptides, collectively called neuregulins (NRG1) that appear to result from alternate splicing of a single gene mapped to the short arm of human chromosome 8 (Orr-Urtreger et al. (1993) *Proc Natl Acad Sci USA* 90:1867-71). The NRG3s (murine and human) were disclosed as being about 713 and 720 amino acids in length, respectively, and to comprise an EGF-like domain, an N-terminal hydrophobic segment, the Ser/Thr-rich portion, a predicted transmembrane domain, and a predicted intracellular domain.

Holmes et al. (*Science* (1992) 256:1205-10; WO 92/20798; and U.S. Pat. No. 5,367,060) described isolation and cloning of a family of polypeptide activators for the HER2 receptor which they called heregulin-α (HRG-α), heregulin-β1 (HRG-β1), heregulin-β2 (HRG-β2), heregulin-β2-like (HRG-β2-like), and heregulin-β3 (HRG-β3). These documents describe (1) the ability of the purified HRG (=NRG) polypeptides to activate tyrosine phosphorylation of the HER2 receptor in MCF7 breast tumor cells and (2) the mitogenic activity of the HRG polypeptides on tumor cells expressing high levels of the HER2 receptor. Like other EGF family growth factors, soluble HRG polypeptides appear to be derived from a membrane bound precursor (pro-HRG) which is proteolytically processed to release the 45 kDa soluble form. Although substantially identical in the first 213 amino acid residues, the HRGs are classified into two major types, α and β, based on two variant EGF-like domains which differ in their C-termini. Based on an amino acid sequence comparison between the first and sixth Cys residues in the EGF-like domain, HRGs were 45% similar to heparin-binding EGF-like growth factor (HB-EGF), 35% identical to amphiregulin, 32% identical to TGF-α, and 27% identical to EGF.

Falls et al. (1993) *Cell* 72:801-815 described a chicken heregulin family member named "acetylcholine receptor inducing activity" (ARIA) polypeptide, that stimulated synthesis of muscle AChRs. See also WO 94/08007. ARIA is a β type HRG and lacks the entire spacer region rich in glycosylation sites between the Ig-like domain and EGF-like domain of HRGα, and HRGPβ1-β3.

Marchionni et al. (1993) *Nature* 362:312-318, identified several bovine-proteins named glial growth factors (GGFs) which share the Ig-like domain and EGF-like domain with the other NRG/HRG proteins described above, but which also have an N-terminal kringle domain. See also WO 92/18627; WO 94/00140; WO 94/04560; WO 94/26298; and WO 95/32724.

Ho et al. (1995) *J. Biol. Chem.* 270:14523-32, described another member of the HRG family called "sensory and motor neuron-derived factor" (SMDF) which has an EGF-like domain characteristic of all other HRG polypeptides but a distinct N-terminal domain. The major structural difference between SMDF and the other HRG polypeptides is the lack of an Ig-like domain and the "glyco" spacer characteristic of all the other HRG polypeptides.

Caraway et al. (1994) *J Biol. Chem.* 269:14303-06 subsequently demonstrated that ErbB3 is a receptor for HRG and mediates phosphorylation of intrinsic Tyr residues and of ErbB2 receptor in cells which express both receptors. HRG was the only known member of the EGF-like family that could interact with several receptors (Carraway et al. (1994) *Cell* 78:5-8.

A number of biological activities of the NRG/HRG proteins have been described:
(1) myotube differentiation via synthesis and concentration of neurotransmitter receptors in the postsynaptic muscle (Falls et al., supra);
(2) increased number of sodium channels in chick muscle (Corfas et al., 1993, *J. Neuroscience* 13:2118-25);
(3) mitogenic stimulation of subconfluent quiescent human myoblasts and their differentiation to yield more myotubes (Sklar et al., WO 94/26298; and
(4) activation of myocardial ErbB2 and ErbB4 receptors by NRG1 (Ford, B D et al., *Dev Biol.* (1999) 214:139-50; Carraway, K L et al., *Bioessays* (1996) 18:263-66.

As described herein and as discussed in the present inventor's earlier application; see also Li et al., 2001, *J Biol Chem.* 276:38068-75).), N-HBD targets the NRG protein to the cell surface by interacting with agrin and other HSPGs in the ECM. See also: Li Q, et al., *Mol. Cell. Neurosci.* 26:558-69. This interaction between NRG and HSPGs not only concentrates NRG proteins near its erbB receptors, but also keeps it there for a sufficiently long time to induce biological activity (in this case, AChR gene expression). Results presented herein, supported by other reports demonstrating the mitogenic effects of NRG in breast and ovarian cancer (Aguilar, Z et al., 1999, *Oncogene.* 18:6050-62. Gilmour, L M et al., 2002, *Clin Canc Res.* 8:3933-42) indicate that blocking NRG activity is an important new method to treat these forms of cancers. For example, a naturally-occurring secreted form of human p85 erbB3 receptor negatively regulates NRG-induced breast cancer cell growth (Lee, H et al., 2001, *Cancer Res.* 61:4467-73). A 120 kDa fusion polypeptide named IgB4 is an NRG antagonist that includes the ECD of the erbB4 receptor fused in frame to the Fc portion of human IgG1 (hinge, $CH_2$ and $CH_3$ domains) (Chen, X, 1996, *J Biol Chem* 271:7620-9). IgB4 is dimeric because of the interchain disulfide bonds between the two Ig γ chains. Both the soluble erbB3 and the IgB4 antagonists worked as dominant-negative NRG receptors by competing with endogenous erbB receptors for NRG binding. While both dominant-negative receptors were reported to block NRG constructs that comprise the EGF-like domain alone, the present inventor and others have been unable to efficiently inhibit the activity of the Ig-EGF form of NRG (measured as erbB phosphorylation). See, for example, Li Q et al. (2004) *Cancer Res* 64:7078-85). According to the present invention, this failure is explained by the fact that Ig-EGF forms of NRG accumulate at the cell surface through HBD/HSPG interactions, attaining high concentrations near their natural erbB receptors. Under such circumstances, soluble antagonists cannot block NRG activity except at very high, practically unattainable, concentrations. One objective of the present invention was to overcome this deficiency.

Heparan Sulfate and HSPGs

Heparan sulfate (HS) is a sulfated polysaccharide found on the surface of most cells as part of proteoglycans (HSPGs) and in the ECM. The polysaccharide mediates the interactions between a number of different proteins. HS consists of alternating hexuronate and glucosamine units. The hexuronate can be either D-glucuronate (GlcA) or L-iduronate (IdoA). The amine of the glucosamine is usually acetylated (N-acetylglucosamine or GlcNAc) or sulfated (N-sulfoglucosamine or $GlcNSO_3$), but it may also be unsubstituted. Potential sulfation sites located on the amino group or positions 2, 3, and 6 of each sugar molecule (Sugahara, K et al. (2002) *IUBMB Life* 54:163-175). Sometimes there are also 3-O-sulfate groups present on $GlcNSO_3$ units. Expression of HS epitopes may be temporally and spatially controlled within different organs and tissues (Lindahl, U et al. (1998) *J Biol Chem* 273:24979-82; Esko, J D et al. (1998) *J Clin Invest* 108:169-173). Thus HSPG specificity may be encoded by the diversity generated by differences in sugar composition and sulfation pattern of the GAG chains (Gabius, H J (2000) *Naturwissenschaften* 87:108-121; Capila, I et al. (2002) *Angew Chem Int Ed Engl* 41:391-412). For example, two fibroblast growth factors, FGF1 and FGF2, require N-sulfated pentasaccharide sequences for optimal binding, but differ in requirements for O-sulfation (Kreuger, J. et al. (2001) *J Biol Chem* 276:30744-52). Hepatocyte growth factor, platelet-derived growth factor, and lipoprotein lipase all depend on the presence of one or more GlcN 6O-sulfate groups (Lyon, M et al. (1994) *Biochem Soc Trans* 22:365-370; Feyzi, E et al. (1997) *J Biol Chem* 272:5518-24; Parthasarathy, N et al. (1994) *J Biol Chem* 269:22391-96). Antithrombin III requires a 3O-sulfated GlcNS unit (Petitou, M et al. (1988) *Carbohyd Res* 179:163-72. Further specificity in the FGF signaling system may also result from either simultaneous or sequential interactions between HS and FGF and its receptors (Allen, B L et al. (2003) *J Cell Biol* 163:637-48; Guimond, S E et al. (1999) *Curr Biol* 9:1343-46).

SUMMARY OF THE INVENTION

Some ABBREVIATIONS used herein include: NRG, neuregulin; NRG, heregulin; HBD, heparin-binding domain; N-HBD, neuregulin heparin-binding domain; AChR, acetylcholine receptor; B4 or B4D, extracellular domain of erbB4 receptor; HSPG, heparan-sulfate proteoglycan; EGF, epidermal growth factor; IG or Ig, immunoglobulin; MAPK, mitogen-activated protein kinase; PI3-K, phosphatidylinositol 3-kinase; BSA, bovine serum albumin; MEM, minimum essential media; CEE, chick embryo extract; α-BTX, α-bungarotoxin; FGF, fibroblast growth factor; ECD, extracellular domain; ECM, extracellular matrix; TGF-β transforming growth factor-β; CREB, cAMP response element-binding protein.

The present inventor conceived that N-HBD (also referred to as the neuregulin IG-like domain) functions to keep the EGF-like domain at sufficiently high concentrations near erbB receptors for a sufficiently long period of time necessary to induce events downstream from the receptor binding. In WO 03/012045, the present inventor described how NRG-HSPG interactions affect NRG-erbB receptor binding, erbB receptor auto-phosphorylation and downstream activation of AChR genes and newly-synthesized proteins. Using recombinant NRG β1 isoforms with and without the HBD, it was demonstrated that the N-HBD potentiated the EGF-like domain's action on receptor phosphorylation by interacting with endogenous HSPGs. Through these HSPG interactions, the N-HBD induced sustained NRG-erbB receptor phosphorylation. These results provided a molecular rationale for the high concentration of NRG in the ECM of neuromuscular synapses.

The N-HBD has two Cys residues separated by 55 amino acids with a Trp located 13 residues from the first Cys. This is characteristic of the Ig C2 subfamily of Ig gene superfamily. For example the native human N-HBD sequence has only 32% sequence identity with a more "conventional" Ig C2 Ig domain found in CD4 molecules. The N-HBD, homologue or functional derivative of the present invention preferably has the above sequence characteristic and less than about 40% identity with an Ig C2 domain of an Ig H or L chain from the same animal species.

The present invention is directed in particular to a novel hybrid or fusion polypeptide (and nucleic acids and expression vectors encoding the polypeptide) that includes at least two domains or peptidic structures: (1) a first "targeting" polypeptide domain whose role is to target the fusion polypeptide, and (2) a fusion partner referred to herein as a "targeted" polypeptide or "$P_{trg}$". The first targeting domain is preferably an animal N-HBD, more preferably a mammalian N-HBD, most preferably a human N-HBD. The second targeted polypeptide $P_{trg}$ preferably comprises the erbB4 ECD (B4D). The fusion polypeptide, through the action of said $P_{trg}$, has enhanced biological activity as an antagonist that blocks the target receptor as compared to native $P_{trg}$ or $P_{trg}$ that is not fused to the targeting polypeptide.

The present invention is also directed to a recombinant hybrid nucleic acid molecule encoding a N-HBD fusion polypeptide which molecule comprises (a) a first nucleic acid sequence of no more than about 100 nucleotides that encodes an animal N-HBD pol a homologue or functional derivative of said polypeptide, which polypeptide, homologue or functional derivative is characterized in that it
  (i) is a member of the C2 subfamily of the immunoglobulin superfamily but has less than about 40% sequence identity to a C2 domain of an immunoglobulin heavy or light chain from the same animal species; and
  (ii) binds to heparin and heparan sulfate proteoglycans with a $K_d$ of $10^{-5}M$ or lower when measured in a conventional heparin-binding or heparan-sulfate binding assay;
(b) optionally (and preferably), fused in frame with the first nucleic acid sequence, a linker nucleic acid sequence encoding a linker peptide; and
(c) a second nucleic acid sequence that (i) is linked in frame to said first nucleic acid sequence or to said linker nucleic acid sequence and (ii) encodes a second polypeptide $P_{trg}$ which second nucleic acid sequence encodes the erbB4 receptor (B4) ECD,
wherein the encoded fusion polypeptide is a neuregulin antagonist.

In the above nucleic acid molecule, the N-HBD polypeptide preferably comprises an amino acid sequence selected from the group consisting of:

(a)
GSKLVLRCET SSEYSSLRFK WFKNGNELNR KNKPQNIKIQ

KKPGKSELRI NKASLADSGE YMCKVISKLG (SEQ ID NO: 1)

from human NRG;

(b)
GSKLVLRCET SSEYSSLRFK WFKNGNELNR KNKPENIKIQ

KKPGKSELRI NKASLADSGE YMCKVISKLG (SEQ ID NO: 2)

from rat NRG;

(c)
GQKLVLRCET TSEYPALRKW LKNGKEITKK NRPENVKIPK

KQKKYSELHI YRATLADAGE YACRVSSKLG (SEQ ID NO: 3)

from avian NRG;
and (d)
a functional derivative or homologue of (a), (b)

or (c).

The above nucleic acid molecule may comprises a nucleotide sequence selected from the group consisting of SEQ ID NO:4, SEQ ID NO:5 or (SEQ ID NO:6).

In another embodiment, the invention is an isolated nucleic acid molecule of no more than about 100 nucleotides that hybridizes with any of the above nucleic acid molecules under stringent hybridization conditions.

The present invention is directed to a hybrid nucleic acid molecule encoding a fusion polypeptide, which molecule comprises:

(a) as a first nucleic acid sequence, any of the above nucleic acid molecules;

(b) optionally, fused in frame with the first nucleic acid sequence, a linker nucleic acid sequence encoding a linker peptide; and (c) a second nucleic acid sequence that (i) is linked in frame to the first nucleic acid sequence or to the linker nucleic acid sequence and (ii) encodes a second polypeptide $P_{trg}$ wherein the $P_{trg}$ preferably comprises the ECD of the erbB4 receptor (which domain is abbreviated herein "B4" or "B4D") and wherein the fusion polypeptide is a NRG antagonist.

If this fusion polypeptide further comprises a linker or spacer sequence S between the N-HBD and the B4D, a preferred spacer is the natural amino acid spacer of NRG having the amino acids sequence of residues 131-195 of SEQ ID NO:14, or a sequence homologous thereto. Other spacer sequences known in the art to provide the same physical characteristics to the polypeptide may be used.

Also provided is an expression vector comprising the above nucleic acid molecule operatively linked to (a) a promoter and (b) optionally, additional regulatory sequences that regulate expression of the nucleic acid in a eukaryotic cell, which vector can be expressed in a cell after delivery to the cell in vitro or in vivo. Preferred vectors are plasmids or viral vectors.

A related embodiment is a vector composition, comprising (a) a first recombinant expression vector having incorporated in its nucleic acid one or more nucleotide sequences encoding a N-HBD polypeptide or a biologically active fragment, homologue or other functional derivative thereof; and (b) a second recombinant expression vector having incorporated in its nucleic acid a nucleotide sequence encoding a polypeptide $P_{trg}$, which is the B4 ECD, wherein the expression vectors are able to co-infect or co-transfect a host cell resulting in co-expression of the $P_{trg}$ and the N-HBD polypeptide, fragment, homologue or derivative.

In the vector composition, the first vector preferably comprises SEQ ID NO:4, SEQ ID NO:5 or SEQ ID NO:6.

The present invention provides a cell transformed or transfected with any of the above nucleic acid molecules or vectors, preferably a mammalian cell, most preferably a human cell. A preferred embodiment is an isolated mammalian cell transfected with an exogenous nucleic acid molecule encoding a mammalian N-HBD polypeptide or a biologically active fragment, homologue or other functional derivative thereof, such that the polypeptide, fragment, homologue or derivative is expressed by the cell.

In the above cell, the exogenous nucleic acid molecule preferably comprises SEQ ID NO:4, SEQ ID NO:5 or SEQ ID NO:6, or a homologue, fragment or functional derivative thereof.

As noted above, this invention is also directed to a hybrid or fusion polypeptide wherein the second targeted polypeptide $P_{trg}$ preferably comprises the B4D and wherein the fusion polypeptide is a NRG antagonist. If this fusion polypeptide further comprises a linker or spacer sequence S between the N-HBD and the B4D, a preferred spacer is the natural amino acid spacer of NRG having the amino acids sequence of residues 131-195 of SEQ ID NO:14, or a sequence homologous thereto. Other spacer sequences known in the art to provide the same physical characteristics to the polypeptide may be used.

The above fusion polypeptide or biologically active fragment, homologue or other functional derivative of the polypeptide is preferably produced by recombinant expression of the above expression vector or vector composition.

In the above fusion polypeptide, the targeting polypeptide preferably has the amino acid sequence SEQ ID NO:1, SEQ ID NO:2 or SEQ ID NO:3, or a heparin binding functional derivative or homologue thereof. A preferred functional derivative is a fragment having the sequence

KWFKNGNELNRKNKPQNIKIQKKPGK, (SEQ ID NO: 7)

KWFKNGNELNRKNKPENIKIQKKPGK (SEQ ID NO: 8)
or

KWLKNGKEITKKNRPENVKIPKKQKK. (SEQ ID NO: 9)

The present fusion polypeptide may further comprise a tag sequence, preferably at its C-terminus; a preferred example is an influenza hemagglutinin (HA) sequence.

In this fusion polypeptide, the heparan sulfate binding region or all or part of the N-HBD, or the homologue or functional derivative, is preferably located N-terminal to the B4D. A most preferred fusion polypeptide has the following schematic structure (from N- to C-terminus): HBD-S-B4D-HA (wherein S is the spacer/linker and HA is the tag). Preferably, the HBD-S-B4D region is encoded by a nucleic acid molecule having the sequence SEQ ID NO:13. In a preferred fusion polypeptide, the HBD-S-B4D region has the sequence SEQ ID NO:14.

Also provided is a pharmaceutical composition useful for delivering a targeted polypeptide to a cell or tissue surface and enhancing the biological activity of the targeted polypeptide, comprising (a) the above B4D fusion polypeptide, and (b) a pharmaceutically acceptable excipient or carrier.

In another embodiment, the invention is directed to a method of inhibiting the activation by NRG of an EGF-receptor and/or stimulation of the growth of cells bearing such receptors by NRG, comprising providing to the receptors or cells an effective amount of the above B4D fusion polypeptide that inhibits binding of NRG and activation of the receptors.

Also included is a method for treating a disease or condition in a subject treatable by the inhibition of NRG signaling, comprising administering to the subject an effective amount of the above pharmaceutical composition whereby the biological activity of the fusion polypeptide is increased compared to the activity of native B4D or a B4D that is not fused to the targeting polypeptide, The invention is particularly useful to treat a tumor or cancer.

Tumors or cancers particularly amenable to the present treatment are those in which tumor growth or metastasis is dependent upon autocrine "loop" of NRG stimulation which is typically sustained and continuous in cells that make and secrete NRG and, at the same time, have activated receptors for this protein. Tumors likely to be most susceptible to the present compositions are those having HS's that are N-sulfated, as well as 2O- and 6O-sulfated. See, e.g., Pankonin M S et al. (2005) *J Biol Chem.* 2005 280:383-8.

Based on the present disclosure and the literature (see below), a wide variety of tumor cells can be inhibited and cancers can be treated in accordance with this invention, including breast and ovarian cancers, gastric, esophageal and colon cancer, pancreatic cancer, gliomas and medulloblastomas, to name a few.

In the above fusion polypeptides, the linker, if present, may be one cleavable by a protease, such as VPRGSD (SEQ ID NO:11) or DDKDWH (SEQ ID NO:12).

The fusion polypeptide may be a linear multimer of two or more repeats of monomers of the first targeting polypeptide linked end to end (i) directly or (ii) with a linker sequence present between the monomer repeats. One example, comprises a tandemly linked dimer or trimer of the first targeting polypeptide fused to the second targeted polypeptide. The second "targeted" polypeptide $P_{trg}$ is preferably (a) a soluble form of a cell surface receptor that is capable, as part of the fusion polypeptide, of binding a ligand for the receptor, thereby acting as an antagonist for ligand activation of the receptor;

(b) a ligand for a cell surface receptor that is capable, as part of the fusion polypeptide, of binding to the receptor and thereby acting as either an agonist or antagonist at the receptor.

The present invention also provides a pharmaceutical composition useful for delivering a targeted polypeptide to a cell or tissue surface and enhancing the biological activity of the targeted polypeptide, comprising: (a) the fusion polypeptide described above; and (b) a pharmaceutically acceptable excipient or carrier.

Also provided is a mammalian, preferably human, cell that expresses on its surface or secretes the above fusion polypeptide.

Another pharmaceutical composition that is useful for delivering a targeted polypeptide that is in a form expressed on the surface of, or secreted by, a recombinant cell, comprises (a) a cell as described above and (b) a pharmaceutically acceptable excipient or carrier.

This invention is further directed to a method for localizing a targeted polypeptide to a cell or tissue surface rich in heparan sulfate, and thereby enhancing its biological activity at the surface, comprising providing to the surface the above fusion polypeptide whereby the $P_{trg}$ of the fusion polypeptide is localized to the surface, such that the biological activity of the $P_{trg}$ is increased compared to the activity of native $P_{trg}$ or $P_{trg}$ not fused to the targeting polypeptide. The polypeptide is preferably provided in vivo. Cell surfaces that are to be preferentially targeted are those rich in N-sulfated, as well as 2O- and 6O-sulfated HSPGs.

Also included is a method for treating a disease or condition in a subject treatable by the action of the $P_{trg}$, comprising administering to the subject an effective amount of the above pharmaceutical composition, whereby the biological activity of the $P_{trg}$ of the fusion polypeptide is increased compared to the activity of native $P_{trg}$ or $P_{trg}$ not fused to the targeting polypeptide, thereby treating the disease or condition.

The method for treating a disease or condition in a subject treatable by the action of the $P_{trg}$, may comprise administering to the subject an effective amount of the above cellular pharmaceutical composition, whereby cells bearing or secreting the $P_{trg}$ are made available to the cell or tissue surface, and wherein, the biological activity of the $P_{trg}$ is increased compared to the activity of native $P_{trg}$ or $P_{trg}$ not fused to the targeting polypeptide, thereby treating the disease or condition.

As noted above, in a preferred embodiment, the disease or condition may be a tumor or cancer. In another embodiment, the disease or condition is a neurological disorder, for example, a neurodegenerative disease, multiple sclerosis, stroke, epilepsy or traumatic brain, spinal cord or peripheral nerve injury. Neurodegenerative diseases treatable by this method include Alzheimer's disease, Parkinson's disease and amyotrophic lateral sclerosis.

The present inventor and colleagues produced a series of 4 constructs either with the HBD of NRG in front of (N-terminal to) or behind (C-terminal to) the ECD of erbB4 receptor and incorporated a hemagglutinin (HA) tag to follow and purify the constructs. Among these 4 antagonists, recombinant proteins that bound heparin with high affinity were the most potent NRG antagonists for blocking NRG signaling. The preferred antagonist is a fusion polypeptide described as HBD-S-B4-HA, which fuses the HBD of NRG, a spacer S, an erbB4 ECD ("B4") and, optionally, an influenza HA sequence for ease of purification. Preferably this molecule is encoded by a nucleic acid molecule having the sequence SEQ ID NO:13. Preferably the fusion polypeptide has the sequence SEQ ID NO:14. More generally, these results show that NRG's HBD domain can be fused to other recombinant proteins as a useful means to target the recombinant proteins to the heparan sulfate rich ECMs. This concept provides a new method of protein drug delivery to specific tissues with significant strengthening of biological effects and less overall toxicity to non-heparin containing cells.

BRIEF DESCRIPTION OF THE DRAWINGS

FIGS. 2A and 2B C show construction and size of recombinant NRG antagonists with an HBD. FIG. 2A is a schematic drawing of NRG antagonist constructs. The ECD of erbB4 was inserted into the multiple cloning site (MCS) at the N terminus of HA tag producing a unique dominant negative erbB4 receptor-B4-HA. The other three antagonists were constructed by adding HBD with or without a spacer domain N-terminal to (HBD-B4-HA and HBD-S-B4-HA) and C-terminal to (B4-HBD-HA) the dominant negative erbB4 receptor (B4-HA). FIG. 2B shows the size of NRG antagonists secreted into the medium of transfected HEK293 cells. Samples of conditioned media from cell lines stably expressing the four NRG antagonists was resolved on 7.5% SDS-PAGE gel. Western blot was performed and anti-HA monoclonal antibody was used to detect the HA-tagged antagonists. All the NRG antagonists were secreted into the medium.

FIG. 5A-5D show studies with purified NRG antagonist fusion proteins. FIG. 5A shows a silver stained protein gel of purified recombinant proteins made in HEK293 cells. Left lane shows "GlyB4" recombinant which is HBD-S-B4-His tag fusion. Right lane shows "B4" which B4-His tagged fusion alone, showing the ease of purification with the incorporation of an His tag in place of the HA tag. FIG. 5B shows that pre-incubation with GlyB4 followed by washing produced a sustained disruption of neuregulin signaling measured as phosphorylation of p185. GlyB4 and B4 were pre-incubated with L6 muscle cells for one hour, then thoroughly washed before adding recombinant neuregulin. Pretreatment with GlyB4 led to complete and sustained blockade of neuregulin signaling, whereas B4 (lacking the HBD), had no sustained effects on neuregulin challenge. FIG. 5C shows that GlyB4 was more effective than B4 at blocking proliferation of MCF10CA1 human breast cancers which were treated with either no drug (control), GlyB4, B4, or Herceptin on days 0, 3, and 6. Identical concentrations of 1 nM GlyB4 were significantly more potent at blocking cancer cell growth compared growth of control cells or cells treated with B4. GlyB4 was comparable, if not slightly more effective, than a much higher concentration of Herceptin® (100 µg/ml). (See FIGS. 6-11 for additional studies with these human breast and breast cancer cell lines. FIG. 5D shows four photomicrographs of the cells whose growth is described graphically in FIG. 5C. Addition of GlyB4 blocks proliferation in part by promoting contact inhibition as shown in these photomicrographs of MCF 10CA1 cells grown for 6 days in the presence of medium only (control), B4, GlyB4 and Herceptin.

FIG. 7A shows Northern blots performed using total RNA isolated from MCF10A, MCF10AT and MCF10CA1 cells with or without 1 nM NRG treatment for 24 hours. The eight genes including heat shock genes (22832, L15189, M94859 and NM_006597), an oncogene (M19722), a cell cycle control gene (U47413) and genes involved in translation and metabolism (L41490 and Y00711) were analyzed for the three cell lines. Without NRG treatment, MCF10CA1 cells expressed much higher basal levels of these genes compared to the MCF10A cells, while pre-malignant MCF10AT cells expressed much lower levels thus requiring a longer exposures, shown on the far right. Each blot was reprobed four times and the 18S RNA is shown for each gel that was used for loading normalization. FIG. 7B shows quantitation (fold changes) of gene expression levels following NRG treatment. NRG treatment of MCF10A cells induced significantly more down-regulation than the MCF10AT cells, with minimal down-regulation of just a few genes seen with MCF10CA1 cells.

FIGS. 8A-8C show decreased responsiveness to NRG, increased erbB2, and decreased erbB3 receptor expression as MCF10A cells become more malignant. FIG. 8A shows ErbB receptor phosphorylation (p185, upper band) measured with increasing concentrations of NRG applied to MCF10A, MCF10AT and MCF10CA1 cells. The lower band represents phosphorylated EGF receptors (erbB1) that may also increase with higher doses of NRG. Quantitation of p185 levels revealed that erbB receptor phosphorylation was present in untreated MCF10AT and MCF10CA1 cells and that exogenous NRG treatment induced strong erbB phosphorylation in both MCF10A and MCF10AT cells, but minimally above a high baseline in the MCF10CA1 cells. FIG. 8B shows that, when reprobed with erbB2 antibodies, only the upper band in FIG. 8A is recognized when the blots are superimposed. Increasing levels of erbB2 were seen as the normal breast epithelial cells were transformed to malignant cancer cells. Quantitation showed statistically significant increases in erbB2 expression in MCF10AT (2-fold) and MCF10CA1 (6-fold) cells relative to the MCF10A cells. Both of these fold-changes had p values <0.001 using the two-tailed Student's t test (*). FIG. 8C shows results of reprobing the same blot with erbB3 antibodies, demonstrating that mostly the upper, but also a smaller proportion of the lower band contained erbB3. In contrast to erbB2, erbB3 expression decreased by almost 2-fold in both the MCF10AT (*p<0.01) and the MCF10CA1 cells (**p<0.005).

FIG. 9A shows RT-PCR performed on MCF10A, MCF10AT and MCF10CA1 cells and demonstrates increasing NRG mRNA (as a ~500 bp PCR product) as the breast epithelial cells became more malignant. FIG. 9B shows results with concentrated, conditioned media from MCF10A, MCF10AT and MCF10CA1 cells, revealing a progressive increase in the amount of NRG secretion. Culture media was applied to L6 cells for 45 min showing increasing levels of endogenous NRG production inducing erbB receptor phosphorylation (p185) as the cells became more malignant (left). The L6 cells were also treated with 0.10 and 50 pM NRG to produce a standard curve (right).

FIG. 10A-10C. The soluble NRG antagonist IgB4 blocked both erbB receptor phosphorylation and proliferation of MCF10CA1 cells. In FIG. 10A, MCF10CA1 cells were treated with and without 1 nM NRG in combination with IgB4 for 30 min followed by western blot analysis of p185 receptor phosphorylation. The membrane was reprobed for erbB2 receptor to normalize for protein loading. FIG. 10B shows quantitation of the p185/erbB2 levels. IgB4 inhibited p185 receptor phosphorylation induced by both endogenous and exogenous NRG. FIG. 10C shows cell proliferation assays that examined the effects of IgB4 (filled symbols) on MCF10CA1 growth rate with (triangles) and without (diamonds) NRG addition. IgB4 significantly blocked both normal and NRG-induced cell growth to a similar level.

FIG. 11A-11C show that the tyrosine kinase inhibitor AG1478 blocked both erbB receptor phosphorylation and proliferation of MCF10CA1 cells. In FIG. 11A, MCF10CA1 cells were treated with and without 1 nM NRG in combination with AG1478 for 30 min followed by western blot analysis of p185 receptor phosphorylation. The membrane was reprobed for erbB2 receptor to normalize for protein loading. This antagonist also block the lower, EGF receptor band. FIG. 11B shows quantitation of the p185/erbB2 levels. IgB4 inhibited p185 receptor phosphorylation induced by both endogenous and exogenous NRG. FIG. 11C shows cell proliferation assays that examined the effects of AG1478 (filled symbols) on MCF10CA1 growth rate with (triangles) and without (diamonds) NRG addition. AG1478 blocked both normal and NRG-induced cell growth to a similar level.

FIG. 12A-12C. An erbB2 specific mAb Trastuzumab (Herceptin®) reduced erbB receptor activation but had no effect on NRG-induced proliferation of MCF10CA1 cells. In FIG. 12A, MCF10CA1 cells were pre-treated with 100 μg/ml of the erbB2 receptor-specific mAb Trastuzumab for 24 hours followed by treatment with or without 1 nM NRG for 30 min. p185 receptor phosphorylation and erbB2 receptor expression were examined by western blot. FIG. 12B shows quantitation of p185/erbB2 levels. Trastuzumab did not affect erbB receptor phosphorylation when applied to MCF10CA1 cells alone, but reduced NRG-induced erbB receptor activation. In FIG. 12C MCF10CA1 cells were pre-treated with 100 μg/ml Trastuzumab (filled symbols) for 24 hours followed by either no treatment (diamonds) or 1 nM NRG treatment (triangles). Trastuzumab did not significantly reduce their growth rate in the absence of added NRG.

In FIG. 21A, 35 ng of NRG1 was incubated with the indicated concentration of heparin for 20 minutes and run on a non-denaturing gel. As the heparin concentration increased, NRG1 shifted in a dose-dependant manner to form NRG1-heparin complexes as determined by western blot using a NRG1 antibody and quantified in FIG. 14B).

FIG. 15A-15B shows that N-sulfation is more important for heparin-NRG1 binding than 2O- and 6O-sulfation. Parallel gel shift assays were performed using either (FIG. 15A) fully sulfated heparin, completely desulfated heparin, and De-N sulfated heparin, or (FIG. 15B) fully sulfated heparin, De-2O sulfated heparin, and De-6O sulfated heparin at 0, 1, 10, and 100 μg/ml. Completely desulfated and De-N sulfated heparins were not able to bind and shift NRG1, whereas De-2O and De-6O sulfated heparins shifted NRG1 better than De-N sulfated heparin but less than fully sulfated heparin. Schematic representations of each of the modified heparins are shown at the bottom of each gel with sulfate groups marked with an "S."

In FIG. 16A, 75 μm NRG1 was incubated in triplicate with heparin (at the given concentrations) for 20 minutes and applied to L6 cells. erbB receptor phosphorylation (p185) was progressively inhibited as heparin concentration increased. Western blots were reprobed for erbB receptors (erbB2/3) to normalize the data. FIG. 16B shows results of the same assay performed with desulfated, De-N sulfated, De-2O sulfated, and De-6O sulfated heparins. Completely desulfated and De-N sulfated heparins were least effective at inhibiting erbB receptor phosphorylation, followed by the De-2O and De-6O sulfated heparins and quantified as percent of control (FIG. 16C). Schematic representations of each of the modified heparins are included next to each gel with sulfate groups marked with an "S."

In FIG. 17A, 35 ng of NRG1 was incubated with fully sulfated heparin fragments ranging from 12 to 2 disaccharides in length for 20 minutes and run on a non-denaturing gel. As heparin chain lengths shortened, the position of the NRG1-heparin complexes, visualized with a NRG1 antibody, shifted upward reflecting decreases in charge/mass ratios associated with the smaller heparin fragments. The intensity of the NRG1 band also decreased with smaller chain length possibly reflecting a lower binding affinity for NRG1. The presence of multiple bands for some of the heparin lengths suggest the possibility of multimeric interactions. In FIG. 17B, each of the heparin fragments in FIG. 17A were incubated with NRG1 and applied to L6 cells. As the chain length of heparin shortened, its ability to inhibit NRG1-induced erbB receptor phosphorylation (p185) was reduced (shown as percent of control).

In FIG. 18A, triplicate cultures of L6 muscle cells were pretreated with either 25 or 50 mM chlorate for 48 hours and then incubated with either full length NRG1 (IgEGF) or NRG1 lacking the heparin-binding domain (EGF). 50 mM chlorate caused a significant decrease in erbB phosphorylation (p185) in IgEGF treated but not EGF treated myotubes, measured by western blotting of erbB2/3 immunoprecipitates using a phosphotyrosine antibody. Band intensities for each of the triplicates were quantified and normalized to the total amount of erbB receptor (erbB2/3) present in sample and expressed as average percent of control in (FIG. 18B). FIGS. 18A and 18B were resolved on separate gels developed for different periods of time, so quantitative comparisons cannot be made between the IgEGF and the EGF forms.

FIG. 19B shows that reduced expression of N-sulfated heparan sulfate decreased the potency of IgEGF NRG1-mediated erbB activation (*, p=0.004), but not NRG1 lacking the heparin-binding domain (EGF) (p=0.219) using the same assay as in FIG. 18A-C. The lane labeled "C" corresponds to a no NRG1 and no siRNA negative control. These results were first normalized to the total amount of erbB2/3 present and then plotted as a percent of the control siRNA treated cultures (FIG. 19C). Better resolution of the multiple p185 bands were seen in the EGF treatment assay in FIG. 19B. There was no statistical difference between IgEGF and EGF activity after +siRNA treatment (p=0.24). Significance was evaluated using the two-tailed Student's t-test, assuming equal variances.

DESCRIPTION OF THE PREFERRED EMBODIMENTS

Figure 1:
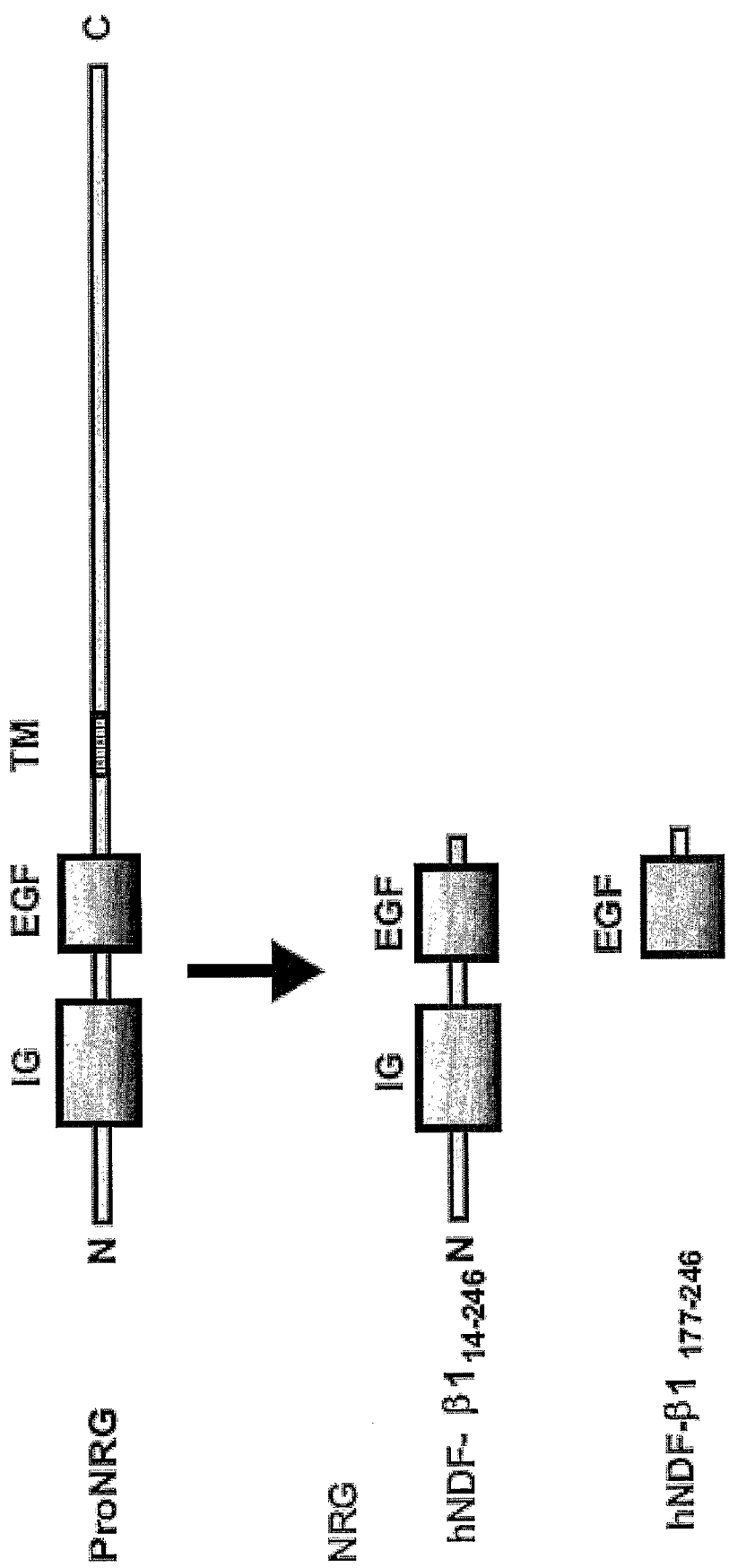
FIG. 1 shows NRG domain structure and constructs used. Type I β1 NRGs are initially synthesized as a transmembrane precursors called proNRG with a C-terminal cytoplasmic domain and a single membrane spanning domain TM. It is cleaved just outside the transmembrane domain and the soluble polypeptide containing the IG and the EGF domains is released. The isolated EGF-like domain construct used here corresponds to amino acid 177-246, and the IG-EGF domain construct corresponds to amino acid 14-246 of the human β1 form.
Figure 3:
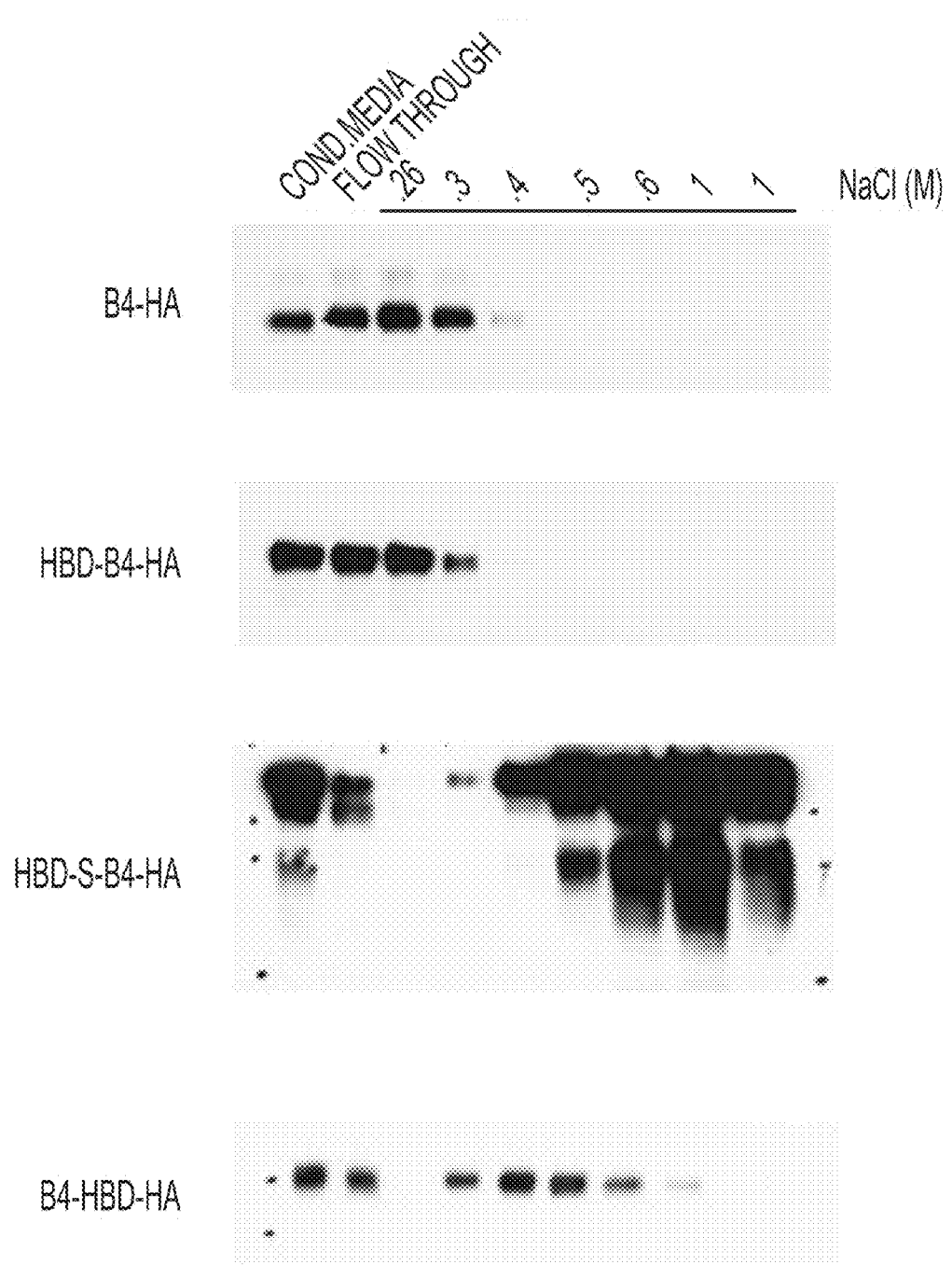
FIG. 3 shows that only recombinant proteins HBD-S-B4-HA and B4-HBD-HA were able to bind to heparin columns. Conditioned media containing the four NRG antagonists (schematically illustrated in FIG. 3A) was passed through heparin columns to allow binding, and then eluted by increasing salt concentrations. Anti-HA western blots from both flow through and elution revealed that both B4-HBD-HA and HBD-S-B4-HA bound to the heparin column with high affinity, while B4-HA and HBD-B4-HA did not bind heparin. HBD-S-B4-HA had a higher affinity of binding than B4-HBD-HA, as a higher salt concentration (1 M) was needed to disrupt HBD-S-B4-HA binding interactions, while only 0.4-0.5 M NaCl was able to elute B4-HBD-HA.
Figure 4:
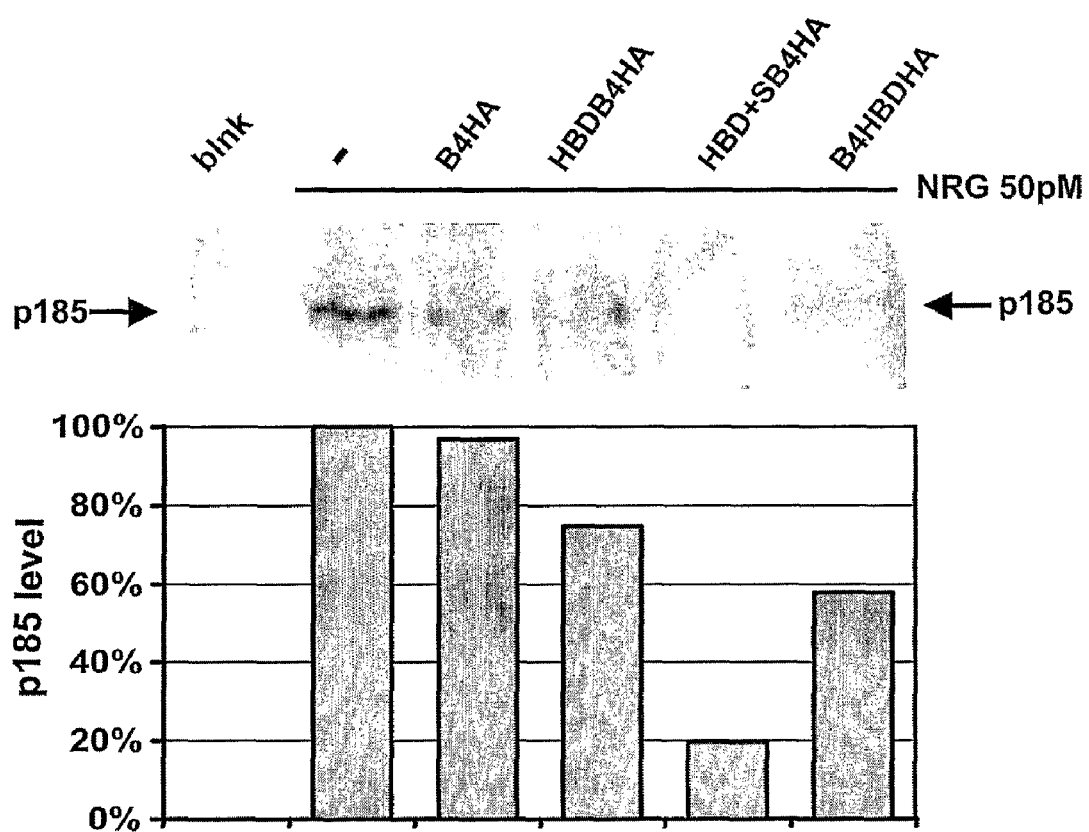
FIG. 4 shows that HBD-S-B4-HA was the most potent NRG antagonist in its ability to block NRG-induced erbB receptor activation in L6 cells. Comparable amounts of NRG antagonists in combination with NRG (50 pM of the IG-EGF form) in L6 media were used to treat L6 cells for 45 min. This was followed by western blot examine p185 erbB receptor phosphorylation. B4-HA and HBD-B4-HA had no effect on p185 receptor phosphorylation induced by NRG, while HBD-S-B4-HA and B4-HBD-HA reduced it to a lower level. HBD-S-B4-HA was a markedly more potent inhibitor of NRG-erbB activation than B4-HBD-HA.

Neuregulins (NRGs) bind to and activate members of the EGF receptor family of tyrosine kinases, thereby initiating a signaling cascade. When the target is the postsynaptic membrane of neuromuscular synapses, one consequence of this activation is the induction of AChR synthesis. In addition to an EGF-like domain, responsible for, and sufficient for receptor binding and tyrosine auto-phosphorylation, many spliced forms of NRGs also have an IG-like domain (=N-HBD) that binds HSPGs and maintains a high concentration of NRG at the synapse.

The present inventor has discovered that the N-HBD functions to keep the EGF-like domain at sufficiently high concentrations for a sufficiently long interval to permit induction of AChR gene expression in primary chick myotubes as a model system. Using recombinant NRGs with and without the N-HBD, it was discovered that N-HBD binding to endogenous HSPGs produces a 4-fold increase in receptor phosphorylation, an effect which was blocked by soluble heparin or by pre-treatment of the muscle cells with the enzyme heparitinase. At least 12-24 hrs of NRG exposure was found to be required to turn on substantial AChR gene expression and that it was important that erbB receptors were kept phosphorylated during this time. The need for sustained erbB receptor activation explains why NRGs are so highly concentrated in the ECM of synapses.

Based on these observations, the present inventor conceived of a broader utility for the N-HBD of NRG, to target any protein or polypeptide to which the domain is fused to a site rich in any binding partner for the domain, whether currently known or later discovered. Primarily such sites are known to be cell surfaces and ECM where HSPGs are expressed.

General References

Unless otherwise indicated, the practice of many aspects of the present invention employs conventional techniques of molecular biology, recombinant DNA technology and immunology, which are within the skill of the art. Such techniques are described in more detail in the scientific literature, for example, Sambrook, J. et al., *Molecular Cloning: A Laboratory Manual*, $2^{nd}$ Ed., Cold Spring Harbor Press, Cold Spring Harbor, N.Y., 1989, Ausubel, F. M. et al. *Current Protocols in Molecular Biology*, Wiley-Interscience, New York, current volume; Albers, B. et al., *Molecular Biology of the Cell*, $2^{nd}$ Ed., Garland Publishing, Inc., New York, N.Y. (1989); Lewin, B M, *Genes IV*, Oxford University Press, Oxford, (1990); Watson, J. D. et al., *Recombinant DNA*, Second Edition, Scientific American Books, New York, 1992; Darnell, J E et al., *Molecular Cell Biology*, Scientific American Books, Inc., New York, N.Y. (1986); Old, R. W. et al., *Principles of Gene Manipulation: An Introduction to Genetic Engineering*, $2^{nd}$ Ed., University of California Press, Berkeley, Calif. (1981); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *Methods in Enzymology: Guide to Molecular Cloning Techniques*, (Berger and Kimmel, eds., 1987); Hartlow, E. et al., *Antibodies: A Laboratory Manual*, Cold Spring Harbor Laboratory Press, Cold Spring Harbor, N.Y., 1988), Coligan, J E et al., eds., *Current Protocols in Immunology*, Wiley-Interscience, New York 1991. Protein structure and function is discussed in Schulz, G E et al., *Principles of Protein Structure*, Springer-Verlag, New York, 1978, and Creighton, T E, *Proteins: Structure and Molecular Properties*, W.H. Freeman & Co., San Francisco, 1983.

In one embodiment, DNA encoding the amino acid sequence corresponding to the N-HBD, from human or other mammals is used. Preferred DNA sequences are:

```
                                            (SEQ ID NO: 4)
ggt tcc aaa cta gtc ctt cgg tgt gaa acc agt tct gaa tac tcc tct ctc aga ttc aag tgg ttc aag aat ggg aat gaa ttg aat cga aaa aac aaa cca caa aat atc aag ata caa aaa aag cca ggg aag tca gaa ctt cgc att aac aaa gca tca ctg gct gat tct gga gag tat atg tgc aaa gtg atc agc aaa tta gga;

(SEQ ID NO: 5)
ggc tcc aag cta gtg ctc cgg tgc gaa acc agc tac gag tac tcc tca ctc aga ttc aaa tgg ttc aag aat ggg aac gag ctg aac cgc aaa aat aaa cca gaa aac atc aag ata cag aac aag cca ggg aag tca gag ctt
```

```
cga att aac aaa gca tcc ctg gct gac tct gga gag tat atg tgc aaa gtg atc agc aag tta gga;
and
                                          (SEQ ID NO: 6)
ggt cag aag cta gtg cta agg tgt gaa acc act tca gag tac cct gcg ctc aga ttc aaa tgg tta aag aac ggg aag gaa ata acg aaa aaa aac aga ccc gaa aat gtc aag atc ccc aaa aag caa aag aaa tac tct gag ctt cat att tat aga gcc acg ttg gct gac gct ggg gaa tac gca tgc aga gtg agc agc aaa cta ggg.
```

Preferably, this is joined to DNA encoding the amino acid sequences of a polypeptide or peptide to be targeted ("$P_{trg}$") (to cell surfaces or ECM) using PCR, to form a construct that is expressed as N-HBD-$P_{trg}$ fusion polypeptide. The techniques for assembling and expressing DNA encoding the N-HBD fusion polypeptides such as synthesis of oligonucleotides, PCR, transforming cells, constructing vectors, expression systems, and the like are well-established in the art. Those of ordinary skill are familiar with the standard resource materials, specific conditions and procedures.

The nucleic acid sequence encoding a construct that combines the NRG HBD, including its natural "spacer" and the erbB4 ECD (B4) as the $P_{trg}$ is shown below as SEQ ID NO:13. It is annotated as follows (referring to the encoded domains, etc.): Signal Sequence: lower case, underscore HBD: bold which includes the spacer double underscored, bold, italic (nt's 385-579) (this is the 'natural' spacer of NRG) following the HBD; Extraneous sequence from cloning (lower case italic); erbB4 ECD (bold, residues 200-822; B4: underscored (upper case, not italic, not underlined)

atgaagccgg cgacaggact ttgggtctgg gtgagccttc tcgtggcggc ggggaccgtc 60 cagccagcg attc*tcagtc aggtac*CAAG AAGAAGGAGC GAGGCTCCGG CAAGAAGCCG 120

GAGTCCGCGG CGGGCAGCCA GAGCCCAGCC TTGCCTCCCC GATTGAAAGA GATGAAAAGC 180

CAGGAATCGG CTGCAGGTTC CAAACTAGTC CTTCGGTGTG AAACCAGTTC TGAATACTCC 240

TCTCTCAGAT TCAAGTGGTT CAAGAATGGG AATGAATTGA ATCGAAAAAA CAAACCACAA 300

AATATCAAGA TACAAAAAAA GCCAGGGAAG TCAGAACTTC GCATTAACAA AGCATCACTG 360

GCTGATTCTG GAGAGTATAT GTGC*AAAGTG ATCAGCAAAT TAGGAAATGA* 420
*CAGTGCCCTCT*

*GCCAATATCA CCATCGTGGA ATCAAACGAG ATCATCACTG GTATGCCAGC CTCAACTGAA* 480

*GGAGCATATG TGTCTTCAGA GTCTCCCATT AGAATATCAG TATCCACAGA AGGAGCAAAT* 540

*ACTTCTTCAT CTACATCTAC ATCCACCACT GGGACAAGCg* gtacccagtcc AGTGTGTGCA 600

GGAACGGAGA ATAAACTGAG CTCTCTCTCT GACCTGGAAC AGCAGTACCG AGCCTTGCGC 660

AAGTACTATG AAAACTGTGA GGTTGTCATG GGCAACCTGG AGATAACCAG CATTGAGCAC 720

AACCGGGACC TCTCCTTCCT GCGGTCTGTT CGAGAAGTCA CAGGCTACGT GTTAGTGGCT 780

CTTAATCAGT TTCGTTACCT GCCTCTGGAG AATTTACGCA TTATTCGTGG GACAAAACTT 840

TATGAGGATC GATATGCCTT GGCAATATTT TTAAACTACA GAAAAGATGG AAACTTTGGA 900

CTTCAAGAAC TTGGATTAAA GAACTTGACA GAAATCCTAA ATGGTGGAGT CTATGTAGAC 960

CAGAACAAAT TCCTTTGTTA TGCAGACACC ATTCATTGGC AAGATATTGT TCGGAACCCA 1020

TGGCCTTCCA ACTTGACTCT TGTGTCAACA AATGGTAGTT CAGGATGTGG ACGTTGCCAT 1080

AAGTCCTGTA CTGGCCGTTG CTGGGGACCC ACAGAAAATC ATTGCCAGAC TTTGACAAGG 1140

ACGGTGTGTG CAGAACAATG TGACGGCAGA TGCTACGGAC CTTACGTCAG TGACTGCTGC 1200

CATCGAGAAT GTGCTGGAGG CTGCTCAGGA CCTAAGGACA CAGACTGCTT TGCCTGCATG 1260

AATTTCAATG ACAGTGGAGC ATGTGTTACT CAGTGTCCCC AAACCTTTGT CTACAATCCA 1320

ACCACCTTTC AACTGGAGCA CAATTTCAAT GCAAAGTACA CATATGGAGC ATTCTGTGTC 1380

AAGAAATGTC CACATAACTT TGTGGTAGAT TCCAGTTCTT GTGTGCGTGC CTGCCCTAGT 1440

TCCAAGATGG AAGTAGAAGA AAATGGGATT AAAATGTGTA AACCTTGCAC TGACATTTGC 1500

CCAAAAGCTT GTGATGGCAT TGGCACAGGA TCATTGATGT CAGCTCAGAC TGTGGATTCC 1560

AGTAACATTG ACAAATTCAT AAACTGTACC AAGATCAATG GGAATTTGAT CTTTCTAGTC 1620

ACTGGTATTC ATGGGGACCC TTACAATGCA ATTGAAGCCA TAGACCCAGA GAAACTGAAC 1680

GTCTTTCGGA CAGTCAGAGA GATAACAGGT TTCCTGAACA TACAGTCATG GCCACCAAAC 1740

-continued

```
ATGACTGACT TCAGTGTTTT TTCTAACCTG GTGACCATTG GTGGAAGAGT ACTCTATAGT   1800

GGCCTGTCCT TGCTTATCCT CAAGCAACAG GGCATCACCT CTCTACAGTT CCAGTCCCTG   1860

AAGGAAATCA GCGCAGGAAA CATCTATATT ACTGACAACA GCAACCTGTG TTATTATCAT   1920

ACCATTAACT GGACAACACT CTTCAGCACA ATCAACCAGA GAATAGTAAT CCGGGACAAC   1980

AGAAAAGCTG AAAATTGTAC TGCTGAAGGA ATGGTGTGCA ACCATCTGTG TTCCAGTGAT   2040

GGCTGB4TTG GGGACCTGGG CCAGACCAAT GTCTGTCGTG TCGCCGCTTC AGTAGAGGAA   2100

GGATCTGCAT AGAGTCTTGT AACCTCTATG ATGGTGAATT TCGGGAGTTT GAGAATGGCT   2160

CCATCTGTGT GGAGTGTGAC CCCCAGTGTG AGAAGATGGA AGATGGCCTC CTCACATGCC   2220

ATGGACCGGG TCCTGACAAC TGTACAAAGT GCTCTCATTT TAAAGATGGC CCAAACTGTG   2280

TGGAAAAATG TCCAGATGGC TTACAGGGGG CAAACAGTTT CATTTTCAAG TATGCTGATC   2340

CAGATCGGGA GTGCCACCCA TGCCATCCAA ACTGCACCCA AGGGTGTAAC GGTCCCACTA   2400

GTCATGACTG CATTTACTAC CCATGGACGG GCCATTCCAC TTTACCACAA CATGCTAAGA   2460

ATTC                                                                2464
```

The translated amino acid sequence of SEQ ID NO:13, above is shown below as SEQ ID NO:14. It includes a signal sequence, HBD, spacer (S) and erbB4 ECD (B4) which are annotated as follows: Signal sequence:—italics (residues 3-27);
HBD—underscored (residues 31-195), particularly a loop that forms is that between the two Cys residues (from $C^{75}$-$C^{150}$ shown as bold and underscored)
Spacer double underscored, bold, italic (residues 131-195)—this is the 'native spacer' found in native NRG just C-terminal to the HBD.
Extraneous sequence from cloning (1. case) from aa 196-199; erbB4 ECD residues 200-822.

Expression Vectors and Host Cells

This invention includes an expression vector comprising a nucleic acid sequence of the invention that encodes an IG-domain fusion polypeptide, operably linked to at least one regulatory sequence. "Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, D., *Meth in Enzymol.* vol. 185, Academic Press (1990)). Those skilled in

```
QKMKPATGLW VWVSLLVAAG TVQPSDSQSG YKKKERGSGK KPESAAGSQS    50

PALPPRLKEM KSQESAAGSK LVLRCETSSE YSSLRFKWFK PNGNELNRKN   100

KQNIKIQKKP GKSELRINKA SLADSGEYMC KVISKLGNDS ASANITIVES   150

NEIITGMPAS TEGAYVSSES PIRISVSTEG ANTSSSTSTS TTGTSgtqsV   200

CAGTENKLSS LSDLEQQYRA LRKYYENCEV VMGNLEITSI EHNRDLSFLR   250

SVREVTGYVL VALNQFRYLP LENLRIIRGT KLYEDRYALA IFLNYRKDGN   300

FGLQELGLKN LTEILNGGVY VDQNKFLCYA DTIHWQDIVR NPWPSNLTLV   350

STNGSSGCGR CHKSCTGRCW GPTENHCQTL TRTVCAEQCD GRCYGPYVSD   400

CCHRECAGGC SGPKDTDCFA CMNFNDSGAC VTQCPQTFVY NPTTFQLEHN   450

FNAKYTYGAF CVKKCPHNFV VDSSSCVRAC PSSKMEVEEN GIKMCKPCTD   500

ICPKACDGIG TGSLMSAQTV DSSNIDKFIN CTKINGNLIF LVTGIHGDPY   550

NAIEAIDPEK LNVFRTVREI TGFLNIQSWP PNMTDFSVFS NLVTIGGRVL   600

YSGLSLLILK QQGITSLQFQ SLKEISAGNI YITDNSNLCY YHTINWTTLF   650

STINQRIVIR DNRKAENCTA EGMVCNHLCS SDGCWGPGPD QCLSCRRFSR   700

GRICIESCNL YDGEFREFEN GSICVECDPQ CEKMEDGLLT CHGPGPDNCT   750

KCSHFKDGPN CVEKCPDGLQ GANSFIFKYA DPDRECHPCH PNCTQGCNGP   800

TSHDCIYYPW TGHSTLPQHA KN                                 822
``` the art appreciate that the particular design of an expression vector of this invention depends on considerations such as the host cell to be transfected and/or the type of protein to be expressed.

The present expression vectors comprise the full range of nucleic acid molecules encoding the various embodiments of N-HBD when included in a fusion polypeptide: full length domain and its functional derivatives (defined herein) including shorter polypeptide fragments, variants, etc. Thus, in one embodiment, the expression vector comprises a nucleic acid encoding at least a portion of the N-HBD, either alone or fused to another polypeptide.

Such expression vectors are used to transfect host cells for expression of the DNA and production of the encoded proteins which include fusion polypeptides. A genetically modified cell expressing the N-HBD polypeptide may transiently express the exogenous DNA for a time sufficient for the cell to be useful for its stated purpose. Thus, if the cell is to serve as a production source or delivery vehicle for the fusion polypeptide in vivo, the duration of expression, or that the cell remain alive, is the time necessary for the cell to exert its production/delivery function. For example, expression of an N-HBD fusion polypeptide may be for as little as 6 hrs, preferably 24 hrs, more preferably for at least 2-4 days. Of course, expression may also be stable (i.e., for the life of the cell). Appropriate expression vectors and regulatory elements (e.g., inducible or constitutive promoters) discussed herein are selected in accordance with the desired duration of expression.

Also provided are methods for producing the N-HBD polypeptide and functional derivatives. For example, a host cell transfected with a nucleic acid vector that encodes an expressable fusion polypeptide comprising at least a portion of the N-HBD polypeptide is cultured under appropriate conditions to allow expression of the fusion polypeptide.

Host cells may also be transfected with one or more expression vectors that singly or in combination comprise DNA encoding at least a portion of the N-HBD protein and DNA encoding at least a portion of a second polypeptide (the $P_{trg}$) so that the host cells produce the fusion polypeptides that include both the portions. When the recombinant expression vector comprises DNA encoding a portion of N-HBD and DNA encoding a $P_{trg}$, the resulting fusion polypeptide may have altered solubility, binding affinity and/or valency. A N-HBD fusion polypeptide is preferably secreted by transfected host cells in cultures and may therefore be isolated from the culture medium. Alternatively, if a protein is retained in the cytoplasm, the cells may be lysed, permitting isolation of the polypeptide from this lysate.

A culture typically includes host cells, appropriate growth media and other byproducts. Suitable culture media are well known in the art. N-HBD protein can be isolated from medium or cell lysates using conventional techniques for purifying proteins and peptides, including ammonium sulfate precipitation, fractionation column chromatography (e.g., ion exchange, gel filtration, affinity chromatography, etc.) and/or electrophoresis. See generally, *Methods in Enzymology* 22:233-577 (1971)). Once purified, partially or to homogeneity, the recombinant N-HBD fusion polypeptide of the invention can be utilized in pharmaceutical compositions as described in more detail herein.

Prokaryotic or eukaryotic host cells transformed or transfected to express N-HBD or functional derivative thereof, preferably fusion polypeptides, are within the scope of the invention. For example, N-HBD may be expressed in bacterial cells such as *E. coli*, insect cells (using a baculovirus vector), yeast cells, or mammalian cells such as Chinese hamster ovary cells (CHO) or human cells. Other suitable host cells may be found in Goeddel, supra, or are otherwise known to those skilled in the art. Expression in eukaryotic cells leads to partial or complete glycosylation and/or formation of relevant inter- or intra-chain disulfide bonds of the recombinant protein.

Examples of vectors for expression in the yeast *S. cerevisiae* well-known in the art include pYepSec1, pMFa, pJRY88, and pYES2. Baculovirus vectors for expression of proteins in cultured insect cells (SF 9 cells) include the pAc series and the pVL series. Generally, COS cells are used in conjunction with such vectors as pCDM8 for transient amplification/expression in mammalian cells, while CHO (dhfr-negative CHO) cells are used with vectors such as pMT2PC for stable amplification/expression in mammalian cells. The NS0 myeloma cell line (a glutamine synthetase expression system.) is available from Celltech Ltd.

In fusion expression vectors, a proteolytic cleavage site may be introduced at the junction of the fusion partner sequences, such as in the case of a reporter group and a target protein, to enable separation of the fusion partners subsequent to purification. Proteolytic enzymes for such cleavage and their recognition sequences include Factor Xa, thrombin and enterokinase. These are discussed below. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein. Inducible non-fusion expression vectors include pTrc and pET 11d (Studier et al., *Meth Enzymol* (1990) 185:60-89).

One embodiment of this invention is a transfected cell which expresses a novel N-HBD fusion polypeptide de novo. In the case of a cell already expressing a N-HBD, the present invention provides a transfected cell expressing increased amounts of the N-HBD polypeptide or functional derivative (defined below). The nucleic acid constructs of this invention can be expressed in cells (or tumors growing in vivo) for purposes of paracrine release and binding to the expressing cells themselves or to other nearby cells which are being targeted. For example, a tumor cell such as a sarcoma, melanoma, leukemia, lymphoma, carcinoma or neuroblastoma is transfected with an expression vector directing the expression of N-HBD or fusion polypeptide either on the tumor cell surface or in secreted form. Such transfected tumor cells can be directed to sites rich in HSPGs. Moreover, cells co-expressing an N-HBD and an immunostimulatory cytokine (e.g., IL-2, IL-4, GM-CSF, and the like) can potentiate the action of the cytokine at a tumor site.

Tumor cells are known to express differential amounts of HSPGs that correlate with their metastatic potential. The balance between HSPG expression and enzymes that degrade HSPGs (e.g., heparanases) can drastically affect their growth and metastasis. For example, pre-treatment of MCF-7 cells with heparanase blocks FGF-induced cell growth, whereas chlorate treatment of MDA-MB-231 cells, that normally produce twice the amount of cell-surface HSPGs, promotes their responsiveness to FGF (Delehedde, M et al., 1996, *Exp Cell Res* 229:398-406. Binding of heparin by FGF, and its close modulation by HSPGs, this suggests a close relationship between FGF responsiveness and HSPG expression. Furthermore, the metastatic potential of tumor cells can be enhanced by expression of endogenous heparanases (Vlodavsky, I. et al., 1999, *Nat Med* 5:793-802). Levels of a prominent HSPG, syndecan-1, is reduced in metastatic tumors (Stanley, M J et al., 1999, *Am J Clin Pathol* 112:377-83). Low molecular weight heparin compounds can actually reduce the metastatic potential of melanoma cells by blocking endogenous heparanases (Miao, H Q et al., 1999, *Int J Cancer* 83:424-31). In view of the foregoing, the present invention is used to differentially target peptides or polypeptides to specific HSPGs.

Vector Construction

Construction of suitable vectors containing the desired coding and control sequences employs standard ligation and restriction techniques which are conventional in the art. Isolated plasmids, DNA sequences, or synthesized oligonucleotides are cleaved, tailored, and religated in the form desired. The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize it in vitro starting from the individual nucleotide derivatives. A nucleic acid, including an entire gene sequence for genes of sizeable length, e.g., 500-1000 bp may be prepared by synthesizing individual overlapping complementary oligonucleotides and filling in single stranded nonoverlapping portions using DNA polymerase in the presence of the dNTPs. This approach has been used successfully in the construction of several genes. See, for example, Edge, M D (1981) *Nature* 292:756; Nambair, K P, et al. (1984) *Science* 223:1299; and Jay, E. *J Biol Chem* (1984) 259:6311.

Synthetic oligonucleotides are prepared by either the phosphotriester method as described by references cited above or the phosphoramidite method (Beaucage, S L et al. (1981) *Tetrahed. Lett.* 22:1859; and Matteucci, M D et al. (1981) *J Am Chem Soc* 103:3185) and can be prepared using commercially available automated oligonucleotide synthesizers. Kinase treatment of single strands prior to annealing or for labeling is achieved using an excess of polynucleotide kinase. Once the components of the desired vectors are thus available, they can be excised and ligated using standard restriction and ligation procedures. Site-specific DNA cleavage is performed by treating with the suitable restriction enzyme (or other nuclease) under known conditions, and the particulars of which are specified by the manufacturer of these commercially available enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hr to two hrs at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Meth Enzymol* (1980) 65:499-560. Restriction cleaved fragments may be blunt ended by treating with the large fragment of *E. coli* DNA polymerase I (Klenow) in the presence of the four dNTPs using known incubation times and concentrations of dNTPs, salts and buffers. If desired, selective repair can be performed by supplying only one, or selected, dNTPs within the limitations dictated by the nature of the overhang. After treatment with Klenow, the mixture is extracted and ethanol precipitated. Treatment under appropriate conditions with S1 nuclease or BAL-31 results in hydrolysis of any single-stranded portion. Ligations are performed under standard conditions and temperatures. Intermolecular "sticky end" ligations are usually performed at 33-100 µg/ml total DNA (5-100 nM final concentration). Intermolecular blunt end ligations may be performed at 1 mM final concentration. In vector construction employing "vector fragments", the fragment is commonly treated with bacterial alkaline phosphatase or calf intestinal alkaline phosphatase to remove the 5' phosphate and prevent self-ligation. Digestions are conducted at pH 8 and the preparation extracted with phenol/chloroform and ethanol precipitated.

Any of a number of methods are used to introduce mutations into the coding sequence to generate desired amino acid sequence variants of the invention. These mutations include simple deletions or insertions, systematic deletions, insertions or substitutions of clusters of bases or substitutions of single bases. For example, modifications of N-HBD DNA sequence (cDNA or genomic DNA) are created by site-directed mutagenesis, a well-known technique for which protocols and reagents are commercially available (Zoller, M J et al. (1982) *Nucl Acids Res* 10:6487-6500; Adelman, J P et al. (1983) *DNA* 2:183-193). Using conventional methods, transformants are selected based on the presence of a selectable marker such as an antibiotic (ampicillin, tetracycline, etc.) resistance gene depending on the mode of plasmid construction. Plasmids are then prepared from the transformants with optional chloramphenicol amplification (Clewell, D B et al. (1969) *Proc Natl Acad Sci USA* 62:1159; (1972) *J Bacteriol* 110:667). Several mini DNA preps are commonly used. See, e.g., Holmes, D S, et al. (1981) *Anal Biochem* 114:193-97; Birnboim, H C et al. (1979) *Nucleic Acids Res* 7:1513-1523. The isolated DNA is analyzed by restriction and/or sequenced by the dideoxy nucleotide method (Sanger (1977) *Proc Natl Acad Sci USA* 74:5463; Messing et al. (1981) *Nucleic Acids Res* 9:309) or by the method of Maxam et al. (1980) *Meth Enzymol* 65:499.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Suitable promoters may be inducible, repressible or constitutive. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M et al., *Cell* 41:521 (1985)) or in the RSV-LTR (from Rous sarcoma virus) (Gorman, C. M., *Proc Natl Acad Sci USA* 79:6777 (1982). Also useful are the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* 290:304-10 (1981)); and the yeast gal4 gene promoter (Johnston, S A et al., *Proc Natl Acad Sci (USA)* 79:6971-75 (1982); Silver, P. A., et al., *Proc Natl Acad Sci (USA)* 81:5951-55 (1984)). Other illustrative descriptions of transcriptional factors associated with promoter regions and their separate activation and DNA binding include: Keegan et al., *Nature* (1986) 231:699; Fields et al., *Nature* (1989) 340:245; Jones, *Cell* (1990) 61:9; Lewin, Cell (1990) 61:1161; Ptashne et al., *Nature* (1990) 346:329; Adams et al., *Cell* (1993) 72:306. The disclosure of all of these above-listed references is hereby incorporated by reference.

The promoter region may further include an octamer region which may also function as a tissue-specific enhancer by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in Roy-Burman et al., U.S. Pat. No. 5,112,767). For a general discussion of enhancers and their actions in transcription, see, Lewin, B M, *Genes IV*, Oxford University Press, Oxford, (1990), pp. 552-76. Particularly useful are retroviral enhancers (e.g., viral LTRs). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency on the DNA molecule of the present invention.

The nucleic acid sequences of the invention can also be chemically synthesized using standard techniques. Various methods of chemically synthesizing polydeoxynucleotides are known, including solid-phase synthesis which, like peptide synthesis, has been fully automated with commercially available DNA synthesizers (See, e.g., Itakura et al., U.S. Pat. No. 4,598,049; Caruthers et al., U.S. Pat. No. 4,458,066; and Itakura, U.S. Pat. Nos. 4,401,796 and 4,373,071, incorporated by reference herein).

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% Ficoll/0.1% polyvinylpyrrolidone/50 nM sodium phosphate buffer at pH 6.5 with 750 mM sodium chloride, 75 mM sodium citrate at 42 C. Another example is use of 50% formamide, 5×SSC (0.75 M NaCl, 0.075 M sodium citrate), 50 mM sodium phosphate (pH 6/8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. Yet another example is hybridization using a buffer of 10% dextran sulfate, 2×SSC and 50% formamide at 55° C., followed by a high-stringency wash consisting of 0.1×SSC containing EDTA at 55° C.

Proteins and Polypeptides

The present invention includes an "isolated" N-HBD polypeptide fragment of human NRG having the sequence

```
                                            (SEQ ID NO: 1)
GSKLVLRCET SSEYSSLRFK WFKNGNELNR KNKPQNIKIQ

KKPGKSELRI NKASLADSGE YMCKVISKLG
``` or, preferably, a fusion polypeptide comprising this sequence, wherein this fusion polypeptide is not to be construed as the native NRG protein.

A preferred subfragment of SEQ ID NO:1 is a fragment rich in basic amino acids: KWFKNGNELNRKNKPQNI-KIQKKPGK (SEQ ID NO:7) which due to its charge would have a relatively high binding affinity for acidic heparan sulfates to which polypeptide or fusion polypeptide comprising SEQ ID NO:7 is intended to be targeted.

The amino acid sequence of the rat N-HBD homologue within rat NRG is

```
                                            (SEQ ID NO: 2)
GSKLVLRCET SSEYSSLRFK WFKNGNELNR KNKPENIKIQ

KKPGKSELRI NKASLADSGE YMCKVISKLG.
```

A preferred fragment of the above sequence is the fragment rich in basic amino acids: KWFKNGNELNRKNKPENI-KIQKKPGK (SEQ ID NO:8) which would have a relative high affinity for the basic heparan sulfates to which the sequence is intended to be targeted.

Homologous chicken sequences were used by the present inventor in the Examples herein. The N-HBD of chicken NRG is

```
                                            (SEQ ID NO: 3)
GQKLVLRCET TSEYPALRK•WLKNGKEITK K NRPENVKIP

KKQKKYSELHI YRATLADAGE YACRVSSKLG
```

As with the human and rat sequence, a preferred fragment of the above sequence is the fragment rich in basic amino acids: KWLKNGKEITKKNRPENVKIPKKQKK (SEQ ID NO:9)

Another preferred functional derivative is a polypeptide having the sequence K-x-x-K-x-x-x-x-x-x-R-K-x-K-x-x-x-K-x-x-K-K-x-x-K (SEQ ID NO:10), wherein x is any amino acid, or a fragment of SEQ ID NO:10 that includes at least four, preferably at least six Lys and/or Arg residues.

While the present disclosure exemplifies the use of fragments of the full length chicken NRG, namely the N-HBD and the EGF-like domain, at the protein and DNA levels, it is to be understood human homologues of the chicken sequences (e.g., SEQ ID NO:1 and 7, and the N-HBD from other mammalian species and mutants thereof that possess the characteristics disclosed herein are intended within the scope of this invention.

Also included is a "functional derivative" of N-HBD which is means an amino acid substitution variant (=mutant), a "fragment," or a "chemical derivative" of N-HBD, which terms are defined below. A functional derivative retains measurable N-HBD activity, preferably that of binding to heparin, heparan sulfate or a HSPG in solution or HSPG on the surface of cells or in an ECM preparation, which permits utility of the derivative in accordance with the present invention.

"Functional derivatives" encompass mutants, "variants" and "fragments" regardless of whether the terms are used in the conjunctive or the alternative herein. Preferred variants are single amino acid conservative substitution variants, though conservative substitution of 2, 3, 4 or 5 residues, for example, is also intended.

A functional homologue must possess the above biochemical and biological activity. In view of this functional characterization, use of homologous N-HBD polypeptides from other species, including polypeptides not yet discovered, fall within the scope of the invention if these polypeptides have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence. For example, when aligning a second sequence to the human N-HBD amino acid sequence (SEQ ID NO:2) having 276 amino acid residues, at least 83, preferably at least 110, more preferably at least 138, even more preferably at least 166, and even more preferably at least 193, 221 or 248 amino acid residues are aligned). The amino acid residues (or nucleotides) at corresponding amino acid positions (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at the Worldwide Web URL gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the above-listed URL), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleotide and amino acid sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to, e.g., human or chicken N-HBD nucleic acid molecules. BLAST protein searches can be performed with the XBLAST program, score=50, wordlength=3 to obtain amino acid sequences homologous to human or murine N-HBD protein molecules of the invention. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See the World Wide Web site www.ncbi.nlm.nih.gov.

Thus, a homologue of the N-HBD protein described above is characterized as having (a) functional activity of a reference N-HBD polypeptide, and (b) sequence similarity to a reference N-HBD polypeptide (such as SEQ ID NO:1) when determined above, of at least about 30% (at the amino acid level), preferably at least about 50%, more preferably at least about 70%, even more preferably at least about 90%.

It is within the skill in the art to obtain and express such a polypeptide using DNA probes based on the disclosed sequences of N-HBD and the published full length sequences of NRG that include flanking nucleotide sequence. Then, the polypeptide's biochemical and biological activity can be tested readily using art-recognized methods such as those described herein, for example, binding to cells or ECM via recognition of the heparan sulfate component of HSPGs associated with cell surfaces and with ECM. Such binding will indicate whether the homologue has the requisite activity to qualify as a "functional" homologue.

Preferred assays measure the functional characteristics of N-HBD which can be "simulated" by binding to the synthetic ligand heparin or assessed by measuring binding to its "natural" ligand heparan sulfate. As exemplified herein, binding of N-HBD (or a fusion polypeptide thereof) to its natural ligand (s) on, for example, muscle cells, permits an associated polypeptide, namely the EGF-like domain of NRG, to transmit a signal (or act as an antagonist and inhibit transmission of a signal) via the tyrosine kinase receptor (erbB4). Any relevant downstream event can be measured whether by biochemical means (e.g., phosphorylation) or by a cellular assay, or a physiologic or pharmacologic assay. As noted above, such binding to muscle cells promotes the transition of AChRs from an embryonic to an adult forms by inducing the switch to the α-AChR subunit and the expression of voltage-gated sodium channels. Moreover, for the engineered fusion polypeptides of this invention that comprise an N-HBD or functional derivative, any assay appropriate for measuring the action of the fusion partner ($P_{trg}$ as defined herein) can be used.

All the polypeptides, fusion polypeptides or other functional derivatives and chemical derivatives including peptidomimetics and multimeric peptides described herein preferably have at least about 20% of the activity of native N-HBD in an in vitro assay. Alternatively, or in addition, these derivatives should compete with labeled N-HBD polypeptide (with an $IC_{50} \leq 10$ μM, more preferably $\leq 1$ μM) for binding to a ligand or binding partner, preferably heparin or HS or HSPG when tested in a binding assay with whole cells, cell fractions, isolated target molecules.

A mutant or "variant" of N-HBD refers to a molecule substantially identical to either the full protein or to a fragment thereof in which one or more amino acid residues have been replaced (substitution variant) or which has one or several residues deleted (deletion variant) or added (addition variant). A "fragment" of N-HBD refers to any subset of the molecule, preferably one that includes the ECD, that is, a shorter polypeptide of the full-length protein.

A number of processes can be used to generate fragments, mutants and variants of the isolated DNA sequence. Small subregions or fragments of the nucleic acid encoding the N-HBD protein, for example 1-30 bases in length, can be prepared by standard, chemical synthesis.

Fusion Polypeptides and Linkers or Spacers

As noted above, a preferred functional derivative is a fusion polypeptide that includes a functional fragment of N-HBD fused or linked to a $P_{trg}$.

The N-HBD or derivative may be linked to the $P_{trg}$ by any type of linker moiety known in the art, e.g., a stretch of Gly residues, a peptide linker comprising various amino acids, or a chemical cross-linking moiety. A preferred linker is one that is cleavable by an enzyme that is present and active in the vicinity of, the cell surface or ECM to which the $P_{trg}$ is being targeted, e.g., at a tumor site. The N-HBD would be released from the therapeutic $P_{trg}$ when the enzyme acts on the fusion polypeptide. Preferred enzymes are a matrix metalloprotease, urokinase, a cathepsin, plasmin or thrombin, which can act to release the $P_{trg}$ in vivo (or in situ) in the tumor milieu. Preferred linkers of this type are peptides having the sequence VPRGSD (SEQ ID NO:11) or DDKDWH (SEQ ID NO:12).

A preferred spacer is the natural NRG spacer at the C-terminal end of the N-HBD (e.g., amino acid residues 131-195 of SEQ ID NO:14, or a homologue or functional derivative thereof.

Multidomain and Multimeric Fusion Polypeptides

The present invention also includes longer polypeptides in which a "unit" peptidic sequence obtained from the sequence of N-HBD or a variant thereof is repeated from about two to about 100 times, with or without intervening spacers or linkers.

A multimer of the peptide referred to symbolically in this section as $\underline{HBD}$ is shown by the following formula $$(\underline{HBD}\text{-}X_m)_n\text{-}\underline{HBD}$$

wherein m=-0 or 1, n=1-100. X is a spacer group, consisting of 1-20 glycine residues, a peptide linker as described above, or a chemical cross-linking moiety.

A preferred HBD unit of such a multimer is KWFKNGNELNRKNKPQNIKIQKKPGK SEQ ID NO:7, or a functional fragment thereof.

Another preferred functional derivative is a polypeptide having the sequence K-x-x-K-x-x-x-x-x-x-R-K-x-K-x-x-x-K-x-x-K-K-x-x-K (SEQ ID NO:10), wherein x is any amino acid, or a fragment of SEQ ID NO:10 that includes at least six Lys or Arg residues. In a more generic version of the above polypeptide, any basic amino acid residue can substitute at the positions occupied by Lys or Arg in SEQ ID NO:10.

It is understood that even if the basic subunit of the multimer has relatively low heparin- (or HS-) binding affinity, the multimer will have increased affinity and/or avidity to the target structure, thereby enabling the use of the multimer in accordance with this invention.

It is also understood that such multimers may be built from any of the polypeptide or peptide variants defined herein. Moreover, a peptide multimer may comprise different combinations of non-identical peptide monomers and the disclosed substitution variants thereof. Such oligomeric or multimeric peptides can be made by chemical synthesis or by recombinant DNA techniques as discussed herein. When produced chemically, the oligomers preferably have from 2-8 repeats of the monomer sequence. When produced recombinantly, the multimers may have as many repeats as the expression system permits, for example from two to about 100 repeats.

In tandem multimers, preferably dimers and trimers, of the N-HBD peptide or polypeptide, the chains bonded by interchain disulfide bonds or other "artificial" covalent bonds between the chains such that the peptide units are "side-by-side" rather than "end-to-end."

Multimers may also include more than one repeat of $P_{trg}$ or a functional derivative thereof that has similar biologic and pharmacologic activity to that of the $P_{trg}$. More than one type of $P_{trg}$ may be combined in a single fusion polypeptide. In this regard, an antigen binding domain of an antibody (Ab) molecule may be fused with an N-HBD and another $P_{trg}$ to result in an Ab:N-HBD:$P_{trg}$ fusion product. Such a polypeptide adds the Ab's selectivity to the delivery mediated by the N-HBD and the desired biological activity provided by the $P_{trg}$. Thus, for example, the Ab may be specific for a tumor cell surface antigen (as is the case with Her2/Neu mAbs used in cancer therapy) so that once the fusion construct is concentrated in the ECM by the N-HBD, the activity may be focused onto tumor cells within that milieu. The Ab domain is preferably introduced into the fusion construct at the DNA level by use of a nucleic acid encoding an Ab Fab fragment, Fv fragment (Hochman, J. et al. (1973) Biochemistry 12:1130-35; Sharon, J, et al. (1976) Biochemistry 15:1591-94) a "single-chain antibody" (scFv, also termed "scAb"). The latter is a single chain polypeptide molecule wherein an Ig $V_H$ domain and an Ig $V_L$ domain are artificially linked by a short peptide linker that allows the scFv to assume a conformation which retains specificity and binding capacity for the antigen (or epitope) against which the original antibody (from which the $V_H$ and $V_L$ domains are derived) was specific. See, for example, Skerra, A et al. (1988) *Science,* 240:1038-41; Pluckthun, A. et al. (1989) *Meth. Enzymol.* 178:497-515; Winter, G. et al. (1991) *Nature* 349:293-99); Bird et al. (1988) *Science* 242:423; Huston et al. (1988) *Proc Natl Acad Sci USA* 85:5879; U.S. Pat. No. 4,704,692, 4,853,871, 4,94,6778, 5,260,203, or 5,455,030.

A "soluble N-HBD" is a cell-free form of N-HBD that may be shed, secreted or otherwise extracted from the producing cells. Soluble N-HBD preferably includes soluble fusion polypeptides wherein the N-HBD is fused genetically or conjugated chemically to a biologically active molecule, such as a $P_{trg}$.

As noted above, a preferred group of N-HBD variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |

| | |
|---|---|
| 3 Polar, positively charged residues | His, Arg, Lys; |
| 4 Large aliphatic, nonpolar residues | Met, Leu, Ile, Val (Cys) |
| 5 Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most preferred deletions, insertions and substitutions according to the present invention are those that do not produce radical changes in the characteristics of the N-HBD polypeptide, maintaining its binding to heparin, HS or HSPGs. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are made by site-specific mutagenesis of the nucleic acid encoding the N-HBD polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

Chemical Derivatives of N-HBD

"Chemical derivatives" of N-HBD contain additional chemical moieties not normally a part of the protein. Covalent modifications of the polypeptide are included within the scope of this invention. Such derivatized moieties may improve the solubility, absorption, biological half life, and the like. Moieties capable of mediating such effects are disclosed, for example, in *Remington's Pharmaceutical Sciences,* $16^{th}$ ed., Mack Publishing Co., Easton, Pa. (1980). Such modifications may be introduced into the molecule by reacting targeted amino acid residues of the polypeptide with an organic derivatizing agent that is capable of reacting with selected side chains or terminal residues. Another modification is cyclization of the protein. Examples of chemical derivatives of the polypeptide are provided below. Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N═C═N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups. Also included are peptides wherein one or more D-amino acids are substituted for one or more L-amino acids.

Peptidomimetics

Another class of compounds useful in this regard are low molecular weight peptidomimetic compounds which mimic the activity of an N-HBD polypeptide. Structure of such peptidomimetics may be derived from the structure of either the free N-HBD or N-HBD bound to its ligand, e.g., heparan sulfate. A peptidomimetic of N-HBD mimics the biological effect of a N-HBD peptide and may be an unnatural peptide or a non-peptide agent which has the stereochemical properties of a N-HBD peptide such that it has the binding activity or biological activity of the peptide. Hence, this invention includes compounds wherein a peptidomimetic compound is coupled to another peptide.

A peptidomimetic agent may be an unnatural peptide or a non-peptide agent which recreates the stereospatial properties of the binding elements of N-HBD such that it has the binding activity or biological activity of N-HBD. Similar to the linear peptides corresponding to N-HBD, a peptidomimetic will have a binding face (which interacts with heparan sulfate) and a non-binding face. Again, similar to linear peptides of N-HBD, the non-binding face of a peptidomimetic will contain functional groups that can be modified by various therapeutic moieties without modifying the binding face of the peptidomimetic. A preferred embodiment of a peptidomimetic would contain an aniline on the non-binding face of the molecule. The $NH_2$-group of an aniline has a pKa ~4.5 and could therefore be modified by any $NH_2$-selective reagent without modifying any $NH_2$ functional groups on the binding face of the peptidomimetic. Other peptidomimetics may not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic moiety could also be directly incorporated during the synthesis of a peptidomimetic and preferentially be displayed on the non-binding face of the molecule.

This invention also includes compounds, which retain partial peptide characteristics. For example, any proteolytically unstable bond within a peptide of the invention could be selectively replaced by a non-peptidic element such as an isostere (N-methylation; D-amino acid at a particular site) or a reduced peptide bond while the rest of the molecule retains its peptide nature.

Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Hruby, V J *Biopolymers* 33:1073-82 (1993); Wiley, R A et al., *Med Res Rev* 13:327-84 (1993); Moore et al., *Adv. in Pharmacol* 33:91-141 (1995); Giannis et al., *Adv. in Drug Res.* 29:1-78 (1997), which references are incorporated by reference in their entirety). These methods are used to make peptidomimetics that possess at least the binding capacity and specificity of N-HBD peptides and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the 3D structure of a peptide determined by crystallography or by nuclear magnetic resonance (NMR) spectroscopy, either when the peptide is free or bound in complex. The better knowledge of the stereochemistry of the interaction of a peptide with its ligand will contribute to the rational design of such peptidomimetic agents.

Engineering of Polypeptides with Improved Specificity and Affinity

Mutants or variant HBD sequences, whether in the form of polypeptides, fusion polypeptides, multimers, etc., with increased binding activity (defined as increased specificity, affinity or both) for a target HS, HSPG or other sugar can be produced and tested using the methods described herein and known in the art. Thus, one screens the binding specificity or affinity of a candidate variant or mutant HBD on oligosaccharide arrays to determine the optimal sugar structures that bind to that HBD. With that information in hand, one can screen a peptide library of the HBD or, in a directed manner, mutate selected residues in the HBD, and screen these mutants for binding to, for example, a tissue array. This generates HBD modules that are characterized in that they bind to specific saccharide moieties expressed on specific tissues or cells. In this way, variant HBDs with improved binding activity for particular targets, e.g., tumors, can be identified and used to engineer better antagonists, such as HBD-containing fusion polypeptides, for that particular target. Methods for preparing and using tissue arrays are described by Richter J et al., 2000, *Am J Pathol* 157:787-94; Fernandez P L et al., *Virchows Arch* 438:591-94; and Simon R et al., 2001, *Cancer Res* 61:4514-19). Tissue binding studies of heparin-binding proteins are described in (Allen B L et al., 2001, *J Cell Biol* 155:845-58; Friedl A et al., 2001, *Methods Mol Biol* 171:535-46; Raparaeger A C, 2002, *Meth Cell Biol* 69:83-109. Thus the present invention includes methods for identifying an HBD with optimal tissue specificity and for making tissue-specific targeting vectors which may be antagonists of a selected biological function. Testing in the appropriate tissue culture system or animal model is performed to determine effectiveness of targeting, toxicity and biological function of the engineered HBD.

The structural specificity required for HBD binding to heparin is exemplified and described in Example III below, and, as in Example II, supports the embodiments of targeting specific cell surfaces based on their unique HS patterns. The N-sulfate group, followed by the 2-O and 6-O sulfate groups, are important for HBD binding (as exemplified in a gel shift experiment and an activity-blocking assay). The importance of these sulfate group, particulate the N-sulfate, was confirmed in cultured cells by specifically blocking the enzyme that catalyzes N-sulfation. It is therefore possible to target a large range of biopharmaceuticals/macromolecular drugs such as proteins, viruses, nanoparticles and oligonucleotides to HS-containing tissues with prominent N-sulfation patterns.

Modification of some of the key amino acids of SEQ ID NO:1 (or SEQ ID NO:2 and 3) would alter the affinity of the HBD for the N-sulfate, 2-O and 6-O sulfate groups and result in altered specificity that would serve as the basis for targeting the HBD to different cell surfaces expressing different sulfation patterns. This permits differentially targeting one cell type in the body vs another (e.g., brain vs. kidney).

Thus, a modified HBD that preferentially bind to HS's with a particular sulfate patterns can then be linked to various biopharmaceuticals for targeting to different tissues in the body.

Based on the foregoing, the present invention includes a method to select a modified HBD from a library, such as a phage display library, which HBD is selective for a particular tissue with a particular sulfation patterns by using sulfated surfaces as the selection means.

In addition to generating tissue-specific targeting HBDs, this method can also be used to target pathological tissues such as biopsies of human cancers. The selection scheme for selecting library members would employ, for example, cancer cells and normal cells to select HBDs that bind with higher affinity to any desired type of cancer cells than to the analogous normal cells (or any other desired normal cells) in the body.

Such a selected set of HS-pattern-specific HBDs can then be linked to a biopharmaceutical that inhibits growth of cancer cells, and, on the basis of selective targeting, has little to no effect on normal cells that do not express the same HS pattern.

Therapeutic Compositions and their Administration

The N-HBD fusion polypeptide or a cell expressing this polypeptide is administered to a mammalian subject, preferably a human. A composition having the activity of N-HBD as described herein is administered in a pharmaceutically acceptable carrier in a biologically effective or a therapeutically effective amount. The N-HBD fusion polypeptide (or cell expressing the polypeptide) may be given alone or in combination with another protein, peptide or other drug.

The N-HBD fusion polypeptide that may be employed in the pharmaceutical compositions of the invention include all of those compounds described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

A composition of this invention may be active per se, or may act as a "pro-drug" that is converted in vivo to the active form.

Compositions within the scope of this invention include all compositions wherein the N-HBD fusion polypeptide, functional derivative, etc. is contained in an amount as defined below that is effective to achieve its intended purpose. The following doses and amounts also pertain to the antibodies of the invention when administered to a subject. A therapeutically effective amount is a dosage that, when given for an effective period of time, achieves the desired pharmacological or clinical effect.

A therapeutically active amount of a polypeptide having N-HBD activity may vary according to factors such as the disease state, age, sex, and weight of the individual, and the ability of the polypeptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount of any of the fusion polypeptides of the present invention is between about 1 ng and about 1 gram per kilogram of body weight of the recipient, more preferably between about 1 µg and 100 mg/kg, more preferably, between about 100 µg and about 100 mg/kg. Dosage forms suitable for internal administration preferably contain (for the latter dose range) from about 0.1 mg to 500 mg of active ingredient per unit. The active ingredient may vary from 0.5 to 95% by weight based on the total weight of the composition. Alternatively, an effective dose of cells expressing N-HBD, such as transduced cells is between about $10^4$ and $10^9$ cells, more preferably between about $10^6$ and $10^8$ cells per subject, preferably in split doses. Those skilled in the relevant therapeutic arts will be able to adjust these doses without undue experimentation.

The active compound, e.g., N-HBD fusion polypeptide or cell transduced with N-HBD DNA, may be administered in a convenient manner, e.g., injection or infusion, by a convenient and effective route. Preferred routes include subcutaneous, intradermal, intravenous and intramuscular routes. Other possible routes include oral administration, intracerebroventricular, intrathecal, inhalation, transdermal application, or rectal administration. For the treatment of tumors which have not been completely resected, direct intratumoral injection is also intended.

Depending on the route of administration, the active compound may be coated in a material to protect the compound from the action of enzymes, acids and other natural conditions which may inactivate the compound. Thus, to a administer a polypeptide or peptide having N-HBD activity by an enteral route, it may be necessary to coat the composition with, or co-administer the composition with, a material to prevent its inactivation. For example, a peptide may be administered to an individual in an appropriate carrier, diluent or adjuvant, co-administered with enzyme inhibitors (e.g., pancreatic trypsin inhibitor, diisopropylfluorophosphate (DFP) and trasylol). or in an appropriate carrier such as liposomes (including water-in-oil-in-water emulsions as well as conventional liposomes (Strejan et al. (1984) *J. Neuroimmunol* 7:27).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, a polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prolonged absorption of the injectable compositions can be brought about by including in the composition an agent which delays absorption, for example, aluminum monostearate and gelatin. Prevention of the action of microorganisms can be achieved by various antibacterial and antifungal agents, for example, parabens, chlorobutanol, phenol, ascorbic acid, thimerosal, and the like.

Parenteral compositions are preferably formulated in dosage unit form for ease of administration and uniformity of dosage. Dosage unit form refers to physically discrete units suited as unitary dosages for a mammalian subject; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

For topical application, the proteins of the present invention may be incorporated into topically applied vehicles such as salves or ointments, which have both a soothing effect on the skin as well as a means for administering the active ingredient directly to the affected area.

The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like.

Other pharmaceutically acceptable carriers for the N-HBD fusion polypeptide according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Delivery of DNA Encoding N-HBD Fusion Polypeptide

DNA delivery to animals, for example to effect what is generally known as "gene therapy," or to cells ex vivo, involves introduction of a "foreign" DNA into a cell and ultimately, into a live animal. As used herein, the term "gene therapy" is not intended to be limited to the correction or replacement of a deficient gene in vivo, rather, the delivery of a polynucleotide, preferably a DNA molecule, of the present invention (not necessarily a "gene") in a manner permitting it expression and thereby, its utility as described. Several general strategies for gene therapy have been studied and have been reviewed extensively (Yang, N-S, *Crit. Rev Biotechnol* 12:335-56 (1992); Anderson, W. F., *Science* 256:808-13 (1992); Miller, A S, *Nature* 357:455-60 (1992); Crystal, R G, *Amer. J. Med.* 92(*suppl 6A*):44S-52S (1992); Zwiebel, J A et al., *Ann. N.Y. Acad. Sci.* 618:394-404 (1991); McLachlin, J R et al., *Prog Nucl Acid Res Molec Biol* 38:91-135 (1990); Kohn, D B et al., *Cancer Invest.* 7:179-92 (1989), which references are herein incorporated by reference in their entirety). One approach comprises nucleic acid transfer into primary cells in culture followed by autologous transplantation (implantation) of the ex vivo transformed cells into the host, either systemically or into a particular organ or tissue.

For accomplishing the objectives of the present invention, nucleic acid therapy would be accomplished by direct transfer of a functionally active, expressable, DNA molecule into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the N-HBD expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful transfer reported in the art include: (a) direct injection of plasmid DNA into mouse muscle tissues, which led to expression of marker genes for an indefinite period of time (Wolff, J A et al., *Science* 247:1465 (1990); (b) retroviral vectors are effective for in vivo and in situ infection of blood vessel tissues; (c) portal vein injection and direct injection of retrovirus preparations into liver effected gene transfer and expression in vivo (Horzaglou, M et al., *J Biol Chem* 265:17285 (1990); Ferry, N et al., *Proc Natl Acad Sci USA* 88:8387 (1991)); (d) intratracheal infusion of recombinant adenovirus into lung tissues was effective for in vivo transfer and prolonged expression of foreign genes in respiratory epithelium (Rosenfeld, M A et al., *Science* 252:431 (1991); (e) Herpes simplex virus vectors achieved in vivo DNA transfer into brain tissue (Ahmad, F et al., eds, *Miami Short Reports—Advances in Gene Technology: The Molecular Biology of Human Genetic Disease*, Vol 1, Boehringer Mannheim Biochemicals, USA, 1991).

Retroviral-mediated human therapy utilizes amphotrophic, replication-deficient retrovirus systems (Temin, H M, *Hum Gene Ther* 1: 111 (1990); Temin et al., U.S. Pat. Nos. 4,980,289, 4,650,764, and 5,124,263; Wills, J W, U.S. Pat. No. 5,175,099; Miller, A D, U.S. Pat. No. 4,861, 719). Such vectors have been used to introduce functional DNA into human cells or tissues, for example, the adenosine deaminase gene into lymphocytes, the NPT-II gene and the gene for TNFα into tumor infiltrating lymphocytes. Retrovirus-mediated gene delivery generally requires target cell proliferation for gene transfer (Miller, D G et al., *Mol Cell Bio.* 10:4239 (1990). This condition is met by certain of the preferred target cells herein, i.e., actively growing tumor cells. Gene therapy of cystic fibrosis using transfection by plasmids using any of a number of methods and by retroviral vectors has been described by Collins et al., U.S. Pat. No. 5,240,846.

The DNA molecules encoding the N-HBD sequences may be packaged into retrovirus vectors using packaging cell lines that produce replication-defective retroviruses, as is well-known in the art (see, for example, Miller, A D et al., *Molec Cell Biol.* 5:431-37 (1985). Newer safe and effective packaging cell lines for gene transfer are described in, e.g., U.S. Pat. No. 5,278,056.

This approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M S, In: *Virology*, Fields, B N et al., eds, Raven Press, NY, 1990, p. 1679; Berkner, K L (1992) *Curr Top Microbiol Immunol* 158:39-66); Strauss, S E, In: *The Adenoviruses*, Ginsberg, H S, ed., Plenum Press, NY, 1984, ch. 11), or herpes simplex virus (HSV) for neuron-specific delivery and persistence. Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R J et al., *EMBO J.* 10:3941 (1991) and is within the scope of this invention.

Vaccinia virus which can be rendered non-replicating can express the DNA molecule of the present invention and is useful in the present therapeutic setting, particularly in humans (U.S. Pat. Nos. 5,225,336; 5,204,243; 5,155,020; 4,769,330; Sutter, G et al., *Proc Natl Acad Sci USA* (1992) 89:10847-51; Fuerst, T R et al., *Proc Natl Acad Sci USA* (1989) 86:2549-2553; Falkner F G et al.; *Nucl Acids Res* (1987) 15:7192; Chakrabarti, S et al., *Molec Cell Biol* (1985) 5:3403-3409). Descriptions of recombinant vaccinia viruses and other viruses containing heterologous DNA and their uses in immunization and DNA therapy are reviewed in Moss, B, *Curr Opin Genet Dev* (1993) 3:86-90; Moss, B, *Biotechnology* (1992) 20: 345-62; Moss, B, *Curr Top Microbiol Immunol* (1992) 158:25-38; Moss, B, *Science* (1991) 252:

1662-67; Piccini, A et al., *Adv Vir Res* (1988) 34:43-64; and Moss, B et al., *Gene Amplif Anal* (1983) 3:201-13.

In addition to naked DNA or RNA, or viral vectors, engineered bacteria may be used as vectors, for example, any of a number of bacterial species including *Salmonella*, BCG and *Listeria monocytogenes* (LM) (Hoiseth et al., *Nature* 291: 238-39 (1981); Poirier, T P et al. *J Exp Med* 168:25-32 (1988); Sadoff, J C, et al., *Science* 240:336-38 (1988); Stover, C K et al., *Nature* 351:456-60 (1991); Aldovini, A. et al., *Nature* 351:479-82 (1991); Schafer, R. et al., *J. Immunol.* 149:53-9 (1992); Ikonomidis, G. et al., *J Exp Med* 180:2209-18 (1994)). The enteric routes of infection of such organisms is a promising characteristic for their use because they may be delivered orally.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N-S, et al., *Proc Natl Acad Sci USA* 87:9568 (1990); Williams, R S et al., *Proc Natl Acad Sci USA* 88:2726 (1991); Zelenin, A V et al., *FEBS Lett.* 244:65 (1989) and *FEBS Lett.* 280:94 (1991); Zelenin, A V et al., *FEBS Lett.* 244:65 (1989); Johnston, S A et al., *In Vitro Cell Dev Bio.* 27:11 (1991)). Furthermore, electroporation, a well-known means to transfer genes into cell in vitro, can be used to transfer DNA molecules according to the present invention to tissues in vivo (Titomirov, A V et al., *Biochim Biophys Acta* 1088:131 ((1991))

"Carrier mediated" gene transfer (or DNA delivery) has also been described (Wu, C H et al., *J Biol Chem.* 264:16985 (1989); Wu, G Y et al., *J Bio. Chem* 263:14621 (1988); Soriano, P et al., *Proc Natl Acad Sci USA* 80:7128 (1983); Wang, C Y. et al., *Proc Natl Acad Sci USA* 84:7851 (1982); Wilson, J M et al., *J Biol Chem* 267:963 (1992)). Preferred carriers are targeted liposomes (Nicolau, C. et al., *Proc Natl Acad Sci USA* 80:1068 (1983); Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Qiagen procedure (Qiagen), followed by DNA purification using known methods, such as the methods exemplified herein.

Again, as noted above, for the utility of transduced N-HBD molecules according to this invention may not require stable or prolonged expression. Rather, transient expression of the polypeptide may be sufficient for transduced cells to perform their "production" or "delivery" function.

Other Therapeutic Compositions

In another embodiment, the N-HBD polypeptide or fusion polypeptide of this invention is "therapeutically conjugated" and used to deliver a therapeutic agent to the site to which the compounds home and bind, i.e., tissues or regions rich in HS such as tumor sites, tumor metastases or foci of infection/inflammation. The term "therapeutically conjugated" means that the modified N-HBD polypeptide is conjugated to another therapeutic agent that is acts on an underlying cause of a disease or to a "component" or step of the process of inflammation, tumor invasion or angiogenesis.

Therapeutic radionuclides that are useful include $^{125}$I, $^{131}$I, $^{90}$Y, $^{67}$Cu, $^{217}$Bi, $^{211}$At, $^{212}$Pb, $^{47}$Sc, and $^{109}$Pd. These atoms can be conjugated to the N-HBD polypeptide compounds directly, indirectly as part of a chelate, or, in the case of iodine, indirectly as part of an iodinated Bolton-Hunter group (whereby the iodine can be introduced either before or after coupling of this group).

Preferred doses of the radionuclide conjugates are a function of the specific radioactivity to be delivered to the target site which varies, in the case of tumors, with tumor type, tumor location and vascularization, kinetics and biodistribution of the N-HBD polypeptide "carrier," energy of radioactive emission by the nuclide, etc. Those skilled in the art of radiotherapy can readily adjust the dose of the polypeptide in conjunction with the dose of the particular nuclide to effect the desired therapeutic benefit without undue experimentation. For example, an effective dose of $^{131}$I-N-HBD polypeptide is between about 1 and 1000 µCi per gram of tumor for an extracranial tumor.

Another therapeutic approach included here is the use of boron neutron capture therapy, in which a boronated polypeptide is delivered to a desired target site, such as a tumor, most preferably an intracranial tumor (Barth, R F, *Cancer Invest* 14:534-50 (1996); Mishima, Y. (ed.), *Cancer Neutron Capture Therapy*, Plenum, N.Y., 1996; Soloway, A H, et al. (eds) *J. Neuro-Oncol.* 33:1-188 (1997). The stable isotope $^{10}$B is irradiated with low energy (<0.025 eV) thermal neutrons, and the resulting nuclear capture yields α particles and $^7$Li nuclei which have high linear energy transfer and respective path lengths of about 9 and 5 µm. This method is predicated on selective $^{10}$B accumulation in the tumor while lower levels present in blood, endothelial cells and normal tissue (e.g., brain). Such delivery has been accomplished using EGF (Yang. W et al., *Cancer Res* 57:4333-39 (1997).

Other therapeutic agents which can be coupled to the N-HBD polypeptides according to the method of the invention are chemotherapeutic drugs, prodrugs, enzymes for activating pro-drugs, photosensitizing agents, nucleic acid therapeutics, antisense vectors, viral vectors, lectins and other toxins.

The compositions of the present invention are useful in treating a wide range of diseases and disorders affecting the nervous system, musculature, and epithelia. In addition, these compositions can be used in the treatment of cancer. As used herein, "treatment" encompasses the treatment of an existing disease or condition as well as prophylactic administration prior to detection or manifestation of the disease or condition (whether primary or recurrent).

Accordingly, the present invention provides a pharmaceutical composition including a N-HBD fusion polypeptide that is useful in treating any of a variety of diseases or disorders. In one embodiment, a pharmaceutical N-HBD fusion polypeptide composition is employed to treat a mammal. In particular, the composition is useful for treating humans, farm animals (e.g., cows and sheep), zoo animals, sporting, animals (e.g., racehorses), and pets. In a preferred embodiment, the composition is used to treat a human.

Two classes of disease or disorder are particularly susceptible to the methods of this invention, based on the knowledge of the effects of NRGs and their antagonists. Described broadly, these include cancer and diseases of the nervous system. The compounds are useful for inhibiting tumor cell invasion and metastasis. Nervous system diseases are preferably neurodegenerative diseases (e.g., Alzheimer's disease, Parkinson's disease, amyotrophic lateral sclerosis (ALS)) stroke, epilepsy, multiple sclerosis (MS), myasthenia gravis, Huntington's chorea, Down's Syndrome, nerve deafness, and Meniere's disease.). Also included are peripheral neuropathies as in diabetes, and repair after traumatic injury to the brain or spinal cord.

The present compositions are used to treat a neuropathy, including a peripheral neuropathy which is a disorder affecting the peripheral nervous system, most often manifested as one or a combination of motor, sensory, sensorimotor, or autonomic neural dysfunctions. Examples include, distal sensorimotor neuropathy and autonomic neuropathies, such as reduced gastrointestinal motility or atony of the urinary bladder. Peripheral neuropathies amenable to treatment by the present compositions can be (a) inherited, (b) a result of a systemic disease, or (c) induced by a toxic agent. Examples of hereditary neuropathies are Charcot-Marie-Tooth disease, Refsum's disease, abetalipoproteinemia, Tangier disease, Krabbe's disease, metachromatic leukodystrophy, Fabry's disease, and Dejerine-Sottas syndrome. Examples of neuropathies resulting from systemic disease include post-polio syndrome. Toxic neuropathies include those that arise as side effects of cancer chemotherapy.

The present hybrid HBD-B4D polypeptides have been primarily characterized herein as antagonists. However, these molecules are also capable of acting as agonists of a more recently described signaling pathway, particularly in neurons. Such signaling is referred to as "back signaling" or "retrograde" signaling and is based on the existence of transmembrane isoforms of NRG-1 that include a highly conserved Cys-rich intracellular domain of unknown function. Bao, J et al. (2003) *J Cell Biol.* 161:1133-41, disclosed that such isoforms can act as bidirectional signaling molecules in neurons. Stimuli for NRG back signaling include binding of erbB receptor dimers to the ECD of NRG and neuronal depolarization. These stimuli elicit proteolytic release and translocation of the intracellular domain of NRG-1 to the nucleus. Once in the nucleus, this molecule has the ability to repress expression of several regulators of apoptosis, resulting, for example, in decreased neuronal cell death. Bao et al., supra, concluded that regulated proteolytic processing of NRG results in retrograde signaling that appears to mediate contact-dependent and activity-dependent survival, at least of NRG-1-expressing neurons. According to the present invention, the present fusion polypeptides are agonists of such back-signaling and can be used to inhibit apoptosis and thereby promote survival of cells that express the appropriate form of membrane bound (vs. soluble) NRG.

High levels of erbB2 expression are associated with accelerated tumor progression and metastatic activity, and erbB2 expression levels are considered to be well-characterized indicators of prognosis in patients with breast cancer (Rubin I et al. (2002)*Ann Oncol* 12(suppl 1):3-8). Furthermore, erbB2 is now a target of novel breast cancer treatments with Trastuzumab (Herceptin®), a mAb against erbB2. In human malignant tissue, overexpression of erbB receptors and/or amplification of their genes are frequent. Among them, EGF receptor is widely distributed throughout the gastrointestinal epithelium. EGF peptides, including transforming growth factor-• (TGF-•), heparin-binding EGF-like growth factor and amphiregulin, activate the tyrosine kinase of the EGF receptor. These peptides are known to exert a variety of effects through EGF receptor on gastrointestinal tract. Expression of erbB2 has also been detected in intestinal and colonic epithelia and gastrointestinal cancers (Quirke P et al. (1989) *Br J Cancer* 60:64-69; Tsujino T et al. (1990) *Br J Cancer* 62:226-30; Jankowski J et al. (1992) *Gut* 33:033-1038). Amplification of the erbB2 gene or overexpression of the erbB2 protein occurs in gastric adenocarcinoma, correlating with metastasis and survival (Ross J S et al. (2001), *Cancer Invest* 19:554-68). In colon cancer, both erbB2 and erbB3 expression levels were higher than in normal mucosa (Maurer C A et al. (1998) *Hum Pathol* 29:771-77). Accumulating evidence suggests that regulation of the HRG/erbB2/erbB3 pathway may play an important role in tumor growth of the colon (Venkateswarlu S et al. (2002) *Oncogene* 21:78-86). Some studies suggest that erbB4 may contribute to the growth of gastric cancer (Kataoka H et al. (1998) *Life Sci* 63:553-64). More recently, associations have been found between erB2 (and EGF-) receptor expression and esophageal adenocarcinoma (including Barrett's esophagus-associated adenocarcinoma) (Chiba, T (2004) *Digestion* 70:93-94). Nakamura T et al., *Cancer* 73:1785-94) found a significant correlation between erbB2 overexpression and increasing depth of invasion, lymph node metastasis, and distant organ metastasis.

Day J D et al. (1996) *Hum Pathol.* 27:119-24 presented histopathologic findings in of pancreatic tissue showing that erbB2 is a potential mediator of growth factor-related signal transduction in pancreatic duct lesions, and provided additional support for the hypothesis that lesions once regarded as various grades of hyperplasia may rather represent intraepithelial neoplasms with the potential for subsequent invasion and metastasis. In normal pancreatic ducts and ductules, erbB2 expression was absent in all but one case. In contrast, erbB2 was expressed in 82% of ducts with flat mucinous hyperplasia, 86% of ducts with papillary mucinous hyperplasia without atypia, 92% of ducts with atypical papillary mucinous hyperplasia, and all specimens with carcinoma in situ. erbB2 expression was observed in 69% of the moderately differentiated infiltrating carcinomas and none of the poorly differentiated infiltrating carcinomas.

Gliomas are the most frequently diagnosed adult primary brain malignancy and have a tendency to invade diffusely into the surrounding healthy brain tissue, thereby precluding their successful surgical removal. NRG-1 plays an important modulatory role in glioma cell invasion (Ritch P A et al. (2003) *J Biol Chem.* 278:20971-78). erbB2 is overexpressed in human glioma biopsies receptor activation by NRG-1 enhanced cell motility in two-dimensional scratch motility assays and stimulated cell invasion in three-dimensional Transwell migration assays.

ErbB-2 and ErbB-4 have been reported to be coexpressed, heterodimerized and of prognostic significance in childhood medulloblastoma (an embryonal tumor of the cerebellar external granule cell layer) (Gilbertson R J et al. (1998) *Cancer Res* 58:3932-41). An NRG-driven ErbB-2/ErbB-4 autocrine loop is an important factor in medulloblastoma tumorigenesis. RT-PCR analysis showed that expression of the ErbB-2 and ErbB-4 receptors (but not ErbB-1 or ErbB-3) were deregulated in medulloblastoma compared with normal developing cerebellum. And NRG1-β was expressed in 87% of medulloblastoma primary tumors, with the greatest expression levels occurring in tumors with high ErbB-2 and ErbB-4 receptor coexpression. Expression of all three components of the proposed autocrine loop (i.e., ErbB-2, ErbB-4, and NRG1-β) was significantly related to the presence of metastases at diagnosis.

Thus, based on the present disclosure and the literature, a wide variety of tumor cells can be inhibited and cancers can be treated in accordance with this invention, including breast and ovarian cancers, gastric, esophageal and colon cancer, pancreatic cancer, gliomas and medulloblastomas, to name a few.

Tumor Systems

The compositions of the present invention are tested for therapeutic efficacy in well established rodent models which are considered to be representative of a human tumor. The overall approaches are described in detail in:
1. Geran, R. I. et al., "Protocols for Screening Chemical Agents and Natural Products Against Animal Tumors and Other Biological Systems (Third Edition)", *Canc. Chemother. Reports*, Part 3, 3:1-112;
2. Plowman, J. et al., In: B. Teicher, ed., Anticancer Drug Development Guide: Preclinical Screening, Clinical Trials and Approval, Part II: In Vivo Methods, Chapter 6, "Human Tumor Xenograft Models in NCI Drug Development," Humana Press Inc., Totowa, N.J., 1997.

Both these references are hereby incorporated by reference in their entirety.

Human Tumor Xenograft Models

The preclinical discovery and development of anticancer drugs as implemented by the National Cancer Institute (NCI) consists of a series of test procedures, data review, and decision steps (Grever, M R, *Semin Oncol.*, 19:622-638 (1992)). Test procedures are designed to provide comparative quantitative data, which in turn, permit selection of the best candidate agents from a given chemical or biological class. Since 1975, the NCI approach to drug discovery involved pre-screening of compounds in the i.p.-implanted murine P388 leukemia model, followed by evaluation of selected compounds in a panel of transplantable tumors (Venditti, J. M. et al., In: Garrattini S et al., eds., *Adv. Pharmacol and Chemother* 2:1-20 (1984)) including human solid tumors. The latter was made possible through the development of immunodeficient athymic nude (nu/nu) mice and the transplantation into these mice of human tumor xenografts (Rygaard, J. et al., *Acta Pathol. Microbiol. Scand.* 77:758-760 (1969); Giovanella, G. C. et al., *J. Natl Canc. Inst.* 51:615-619 (1973)). Studies assessing the metastatic potential of selected murine and human tumor-cell lines (B16, A-375, LOX-IMVI melanomas, and PC-3 prostate adenocarcinoma) and their suitability for experimental drug evaluation supported the importance of in vivo models derived from the implantation of tumor material in anatomically appropriate host tissues; such models are well suited for detailed evaluation of compounds that inhibit activity against specific tumor types. Beginning about 1990, the NCI began employing human tumor cell lines for large-scale drug screening ((Boyd, M R, In: DeVita, V T et al., Cancer: Principles and Practice of Oncology, Updates, vol 3, Philadelphia, Lippincott, 1989, pp 1-12; B. Teicher, ed., *Anticancer Drug Development Guide: Preclinical Screening, Clinical Trials and Approval* chapter 2). Cell lines derived from seven cancer types (brain, colon, leukemia, lung, melanoma, ovarian, and renal) were acquired from a wide range of sources, frozen, and subjected to a battery of in vitro and in vivo characterization. This approach shifted the screening strategy from "compound-oriented" to "disease-oriented" drug discovery (Boyd, supra). Compounds of identified by the screen, demonstrating disease-specific, differential cytotoxicity such as the anti-melanoma activity of the compounds described herein, were considered "leads" for further preclinical evaluation. A battery of human tumor xenograft models was created to deal with such needs. The approach used to establish s.c. xenografts from human tumor cell culture lines is that obtained from the NCI tumor repository at Frederick, Md.). The cryopreserved cell lines are thawed, cultured in RPMI 1640 medium supplemented with 10%-heat-inactivated fetal bovine serum, and expanded until the population is sufficient to yield $\geq 10^8$ cells. Cells are harvested and then implanted s.c. into the axillary region of 10 athymic nu/nu mice ($10^7$ cells/0.5 ml/mouse). Preferred housing conditions for these mice include sterile, polycarbonate, filter-capped microisolator cages maintained in a barrier facility on 12-h light/dark cycles, and provision of sterilized food and water ad libitum. The implanted animals are observed twice weekly for tumor appearance. Growth of the solid tumors is monitored using in situ caliper measurements to determine tumor mass. Weights (mg) are calculated from measurements (mm) of two perpendicular dimensions (length and width) using the formula for a prolate ellipsoid and assuming a specific gravity of 1.0 g/cm$^3$ (Geran et al., supra). Fragments of these tumors may be subjected to histological, cytochemical, and ultrastructural analysis to monitor the characteristics of the in vivo material and to compare them with those of the in vitro lines and, where possible, with those reported for initial patient tumors (Stinson S F et al., *Anticancer Res* 12:1035-1054 (1992)). Both in vitro and in vivo tumor materials should exhibit characteristics consistent with tissue type and tumor of origin, though differences in the degree of differentiation between some of the cultured cell lines and corresponding xenograft materials are not uncommon.

The in vivo growth characteristics of the xenografts determine their suitability for use in the evaluation of test agent antitumor activity, particularly when the xenografts are utilized as early stage s.c. models. As used herein, an early stage s.c. model is defined as one in which tumors are staged to 63-200 mg prior to the initiation of treatment. Growth characteristics considered in rating tumors include take-rate, time to reach 200 mg, doubling time, and susceptibility to spontaneous regression.

Experimental Metastasis

A preferred model utilizes the set of breast tumor cell lines described herein in Example II. Preferably, the tumors are tested in an experimental metastasis model, in which appropriate numbers of tumor cells are injected intravenously (iv) into an immunocompromised mouse, and at various times thereafter, the lungs are removed to enumerate microscopic or macroscopic metastases. The compositions of the invention may be given before, together with, or after the tumor cells (or any combination of these). This permits differentiation between prophylactic and therapeutic activities of the compositions.

Other models are described briefly below.

Xenograft Model of Subcutaneous (s.c.) Tumor Growth

In an exemplary model system, nude (nu/nu) mice are inoculated with MDA-MB-231 cells (human breast carcinoma) ($10^6$ cells in 0.2 ml) s.c. in the right flank of the animals. The tumors are staged to 200 mm$^3$ and then treatment with a test composition is initiated (100 µg/animal/day given q.d. IP). Tumor volumes are obtained every other day and the animals are sacrificed after 2 weeks of treatment. The tumors are excised, weighed and paraffin embedded. Histological sections of the tumors are analyzed, for example, by H and E, anti-CD31, Ki-67, TUNEL, and CD68 staining.

Xenograft Model of Metastasis

The compounds of this invention are also tested for inhibition of late metastasis using an experimental metastasis model (Crowley, C W et al., *Proc. Natl. Acad. Sci. USA* 90 5021-5025 (1993)). Late metastasis involves the steps of attachment and extravasation of tumor cells, local invasion, seeding, proliferation and angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This approach permits utilization of either of these markers (fluorescence detection of GFP or histochemical calorimetric detection of enzymatic activity) to follow the fate of these cells. Cells are injected, preferably iv, and metastases identified after about 14 days, particularly in the lungs but also in regional lymph nodes, femurs and brain. This mimics the organ tropism of naturally occurring metastases in human prostate cancer. For example, GFP-expressing PC-3 cells ($10^6$ cells per mouse) are injected iv into the tail veins of nude (nu/nu) mice. Animals are treated with a test composition at 100 μg/animal/day given q.d. IP. Single metastatic cells and foci are visualized and quantitated by fluorescence microscopy or light microscopic histochemistry or by grinding the tissue and quantitative colorimetric assay of the detectable label.

Inhibition of Spontaneous Metastasis In Vivo in Rodent Model

The rat syngeneic breast cancer system (Xing et al., *Int. J. Cancer* 67:423-429 (1996) employs Mat BIII rat breast cancer cells. Tumor cells, for example about $10^6$ in 0.1 ml PBS, are inoculated into the mammary fat pads of female Fisher rats. At the time of inoculation, a 14-day Alza osmotic minipump is implanted intraperitoneally to dispense the test compound. The compound is dissolved in PBS (e.g., 200 mM stock), sterile filtered and placed in the minipump to achieve a release rate of about 4 mg/kg/day. Control animals receive vehicle (PBS) alone or a vehicle control peptide in the minipump. Animals are sacrificed at about day 14. In the rats treated with the active compounds of the present invention, significant reductions in the size of the primary tumor and in the number of metastases in the spleen, lungs, liver, kidney and lymph nodes (enumerated as discrete foci) are observed. Histological and immunohistochemical analysis reveal increased necrosis and signs of apoptosis in tumors in treated animals. Large necrotic areas are seen in tumor regions lacking neovascularization. HBD-S-B4-based fusion polypeptides ("GlyB4") (e.g., with an HA or His tag) and their derivatives are effective and are found to be at least two-fold more potent than the relevant control polypeptides. In contrast, treatment with control polypeptides fails to cause a significant change in tumor size or metastasis.

For a compound to be a useful anti-cancer agent in accordance with this invention, it should demonstrate significant anti-tumor activity (e.g., inhibiting proliferation of primary or metastatic tumors, metastasis of the tumor, tumor angiogenesis, etc.) in at least one art-recognized in vitro or in vivo assay system, such as those described above.

The application of the present fusion polypeptides that act as tyrosine kinase receptor antagonists is broad and includes conditions associated with abnormal or undesired angiogenesis or cell migration or invasion. A nonlimiting list of these include primary and metastatic solid tumors, benign hyperplasias, atherosclerosis, myocardial angiogenesis, post-balloon angioplasty vascular restenosis, neointima formation following vascular trauma, vascular graft restenosis, coronary collateral formation, deep venous thrombosis, ischemic limb angiogenesis, telangiectasia, pyogenic granuloma, corneal diseases, rubeosis, neovascular glaucoma, diabetic and other retinopathy, retrolental fibroplasia, diabetic neovascularization, macular degeneration, endometriosis, arthritis, fibrosis associated with chronic inflammatory conditions (including psoriasis and scleroderma), lung fibrosis, chemotherapy-induced fibrosis, wound healing with scarring and fibrosis, peptic ulcers, fractures, keloids, and disorders of vasculogenesis, hematopoiesis, ovulation, menstruation, pregnancy and placentation, or any other disease or condition in which angiogenesis is pathogenic or undesired.

In addition to the active EGF-like domain of NRG (as an agonist) and ECDs of the erbB receptors (as antagonists), other active growth and differentiation factors and their respective receptors could also be the $P_{trg}$ component of the present fusion polypeptides and could therefore be targeted to cell surfaces as agonists (growth/differentiation factor domains(s) as $P_{trg}$) or antagonists (receptor ECD as $P_{trg}$). This includes, without limit, EGF. fibroblast growth factors (FGFs), neurotrophins (such as brain derived neurotrophic factor, BDNF, glial derived neurotrophic factor (GDNF), nerve growth factor (NGF), NT4, etc.), VEGF, HB-EGF, and cytokines including but not limited to transforming growth factors α and β (TGFα and TGFβ), netrins and ephrins.

Non-limiting examples of selected nerve growth factors (NGF's) for use in particular neurological disorders are as follows. In ALS, a preferred $P_{trg}$ is BDNF or NT4 which is delivered to HSPG-rich cell surfaces to provide neuroprotection. In Alzheimer's disease, a preferred $P_{trg}$ is any neurotropic factor that stimulates survival or growth of neurons, e.g., central cholinergic neurons. For Parkinson's disease, a preferred $P_{trg}$ is any neurotrophic factor that promotes survival or growth of nigrostriatal dopaminergic neurons (or other dopaminergic cells transplanted to the same site). In myasthenia gravis, the preferred $P_{trg}$ is neuregulin or other stimulator of postsynaptic AChRs delivered to cholinergic neuromuscular junctions. For diabetic neuropathy, a preferred $P_{trg}$ is NGF delivered to any appropriate target organ, such as retina or kidney.

Having now generally described the invention, the same will be more readily understood through reference to the following examples which are provided by way of illustration, and are not intended to be limiting of the present invention, unless specified.

Example I

Targeting Recombinant NRG Antagonists to the ECM By NRG's Heparin Binding Domain Materials and Methods NRG β1 recombinant protein IG-EGF form which corresponding to amino acid 14-276 was provided by Amgen (Thousand Oaks, Calif.). The NRG antagonist IgB4 construct was a gift from Dr. Y. Yarden (Weizmann Inst., Rehovot, Israel). All the media, buffers and ingredients for cell culture and transfection reagents were purchased from Gibco-Invitrogen Life Science (Carlsbad, Calif.). The heparin column was from Sigma (St. Louis, Mo.). Phosphotyrosine antibody 4G10 was purchased from Upstate Biotechnology Incorporation (Lake Placid, N.Y.); anti-HA monoclonal raw ascites fluid HA.11 was from Covance Inc. (Princeton, N.J.); the anti-HA affinity matrix (3F10) was from Roche (Indianapolis, 1N); Goat anti-mouse secondary antibody was from Chemicon (Temecula, Calif.). The Gelcode SilverSNAP Stain kit was purchased from Pierce Biotechnology (Rockford, Ill.).

2. B4-HA and B4-Fc-HA Construct Preparation:

The ECD of erbB4 receptor corresponds to residues 28-1978 bp of the human erbB4 NM_005235 mRNA [see SEQ ID NO:13], and 34-108 bp is translated into a 25 amino acid signal sequence for the localization of the mature protein. The HBD and HBD-S domains of NRG were derived from human NRG1 NM_013964, in which the HBD domain corresponds to 172-489 bp of the DNA sequence, while HBD-S (including the spacer domain) extended from 172 bp to 663 bp. Plasmid pMH (Boehringer Mannheim, Indianapolis, Ind.) which the multiple cloning site (MCS) is located at the $NH_2$ terminus of the HA tag was used to generate B4-HA and B4-Fc constructs from NRG antagonist IgB4 (Chen, X, 1996, *J Biol Chem* 271:7620-9) in plasmid pcDM7. PCRs of IgB4 were performed to add restriction enzyme sites Kpn I and EcoR I on both the ECD of erbB4 (B4HA) alone and erbB4-Fc (B4FcHA).

The primer pair for B4HA was:

forward
[SEQ ID NO: 15]
5'-C TTG GGT ACC CAA AAA ATG AAG CCG GCG ACA G-3';

reverse
[SEQ ID NO: 16]
5'-CG CGA ATT CTT AGC ATG TTG TGG TAA AGT GG-3'

The primer pair for B4FcHA was:

forward
[SEQ ID NO: 17]
5'-C TTG GGT ACC GAA AAA ATG AAG CCG GCG ACA G-3' reverse
[SEQ ID NO: 18]
5'-CCG CGA ATT CAC TCA TTT ACC CGG AGA CAG GG-3'.

Conditions for PCR were as follows: 10 mM Tris-HCl, pH 8.5, 50 mM KCl, 15 mM $MgCl_2$, 200 mM dNTP, 0.5 mM of each primer and 1.25 U of Taq polymerase (Takara Bio., Madison, Wis.). Both the plasmid and the PCR products were digested with restriction enzymes Kpn I and EcoR I. The fragments were "cleaned up" by Quiax gel extraction kit (Qiagen, Valencia, Calif.) before ligation at room temperature for 5 min using rapid DNA ligation kit (Boehringer Mannheim, Indianapolis, Ind.). The complete coding region was sequenced in order to verify the PCR fragment and the ligation.

3. B4-HBD-HA, HBD-B4-HA and HBD-S-B4-HA Construct Preparation:

B4-HBD-HA was subcloned from B4-Fc-HA construct. The human HBD domain of NRGβ1 form was amplified from plasmid HARIA $PATH_2$ (from S. Tejvir, University of Pennsylvania) to add BamHI and EcoRI restriction enzyme sites using primer pair:

forward
[SEQ ID NO: 19]
5'-CAG GAT CCC AAG AAG AAG GAG CGA GGC CTC C-3';

reverse
[SEQ ID NO: 20]
5'-G CGA ATT CCC TAA TTT GCT GAT CAC TTT GC-3'

The HBD PCR fragment was digested with BamHI and EcoRI and inserted into the MCS site after the Fc portion was cut out of the B4FcHA construct.

HBD-B4-HA and HBD-S-B4-HA were made by three steps.

(1) A SS-HA construct was made by subcloning the signal sequence (SS) of erbB4 into the MCS site of pMH by adding Hind III and Kpn I sites using primer pairs:

forward
[SEQ ID NO: 21]
5'-G CCA AGC TTG CAA AAA ATG AAG CCG GCG ACA G-3';

reverse
[SEQ ID NO: 22]
5'-GA GGT ACC CTG AGA ATC GCT GGG CTG GAC G-3'.

(2) The SS-erbB4-HA construct was then subcloned by inserting the erbB4 ECD without its signal sequence into the SS-HA construct between the restriction enzyme sites Kpn I and EcoR I by using the primer pair:

forward
[SEQ ID NO: 23]
5'-TTG GGT ACC CAG TCA GTG TGT GCA GGA ACG-3';

reverse
[SEQ ID NO: 24]
5'-CG CGA ATT CTT AGC ATG TTG TGG TAA AGT GG-3'.

(3) PCRs were performed to obtain the HBD and HBD-S domains with Kpn I site on both sides. The primer pair used for HBD domain was:

forward
[SEQ ID NO: 25]
5'-TG GGT ACC AAG AAG AAG GAG CGA GGC TCC G-3';

reverse
[SEQ ID NO: 26]
5'-GA GGT ACC TCC TAA TTT GCT TAT CAC TTT GC-3'.

The primer pair used for HBD-S domain was:

forward
[SEQ ID NO: 27]
5'-TG GGT ACC AAG AAG AAG GAG CGA GGC TCC G-3';

reverse
[SEQ ID NO: 28]
5'-GA GGT ACC GCT TGT CCC AGT GGT GGA TGT AG-3'.

The HBD-B4-HA and HBD-S-B4-HA constructs were finally made when the PCR products of HBD or HBD-S was inserted between the SS and the erbB4 sequences of the SS-erbB4-HA construct. DNA sequencing was applied to verify the fusion constructs sequence and the proper orientation in frame.

4. Cell culture: The L6 cells were cultured in DMEM supplemented with 10% fetal calf serum, 1 mM L-glutamine and 1000 U/ml penicillin/streptomycin at 37° C. in 10% $CO_2$ incubator. The HEK293 cells were cultured in DMEM with 10% fetal calf serum, 1 mM L-glutamine, 2 mM sodium pyruvate, 0.1 mM non-essential amino acids, 1000 U/ml penicillin/streptomycin at 37° C. in 10% $CO_2$ incubator. The selective antibiotics Geneticin 200 μg/ml (Gibco-Invitrogen) was added to the cell cultures of stably transfected HEK293 cells harboring the NRG antagonists.

5. Stable expression of NRG antagonists in HEK293 cells: HEK293 cells were cultured in 25 mm flasks to 80% confluence and transfected with the four NRG antagonist constructs using lipofectamine 2000 (Invitrogen Life Science) as instructed. The antibiotic Geneticin was then added at a concentration of 400 μg/ml to the transfected HEK293 cells to select the positive antagonist transfected cells. After three weeks of Geneticin selection, the transfected HEK293 cells were diluted and plated in 96 well plates to yield single positive clones. The single clones that expressed the highest levels of antagonists (confirmed by western blot using HA antibody) were then maintained in culture media with 200 μg/ml Geneticin. Optimem I (Gibco-Invitrogen) was applied to the stably transfected NRG antagonist cell lines at 37° C. in 10% $CO_2$ incubator for 2 days. The conditioned Optimem I media was then used in the following experiments.

6. Heparin column binding: The conditioned media containing the four NRG antagonists was passed through the heparin column to allow binding to heparin. The excessive unbound antagonist proteins were washed off by 1×PBS twice. The antagonist proteins were then eluted by increasing concentration of NaCl (0.25, 0.3, 0.4, 0.5, 0.6 and 1M). The flow through solution from each step was examined by anti-HA western blots, as described later, to determine heparin binding ability of the antagonists.

7. Purification and quantitation of recombinant proteins: The NRG antagonists were purified by anti-HA affinity matrix (3F10) (rat mAb) according to manufacturer's instructions. Briefly, the column was equilibrated with buffer containing 20 mM Tris pH 7.5, 0.1 M NaCl, 0.1 M EDTA, and each antagonist in conditioned medium was applied individually to the anti-HA affinity matrix. Excess unbound antagonist proteins were washed with 20 volume of washing buffer (20 mM Tris pH 7.5, 0.1 M NaCl, 0.1 M EDTA and 0.05% Tween 20). The bound NRG antagonists were eluted with 0.1 M glycine (pH 2). The purified recombinant protein was then quantified using a BioRad Protein Assay kit (Bio-Rad, Hercules, Calif.)

8. Silver stain: Both the conditioned media and the purified NRG antagonists were resolved on 7.5% reducing SDS-polyacrylamide gels. The gel was fixed with 30% ethanol and 10% acetic acid for 30 min. 10% ethanol and ultrapure water were used subsequently to wash the gel before staining with SilverSNAP stain solution with enhancer for 30 min. The gel was then developed using SilverSNAP developer solution with enhancer. 5% acetic acid was used to stop the reaction when the desired band intensity was reached. The gel was dried on filter paper using a vacuum gel dyer.

9. L6 assay: Comparable amounts of NRG antagonists in combination with 50 pM NRG were applied to L6 cells on the $8^{th}$ day after plating the cells and allowed to incubate for 45 min at 37° C. in a 10% $CO_2$ incubator. Positive control L6 cells were treated with 50 pM NRG alone. L6 cell lysates were prepared and run on 5% SDS-PAGE gel. Western blots of erbB receptor phosphorylation were performed using 4G10 antibody.

10. Western blot: Western blots were performed on both conditioned NRG antagonist media and the antagonist-treated L6 cells. The antagonist proteins and the L6 cells were solubilized in SDS sample buffer and boiled for 5 min as described above (see also Li et al., supra). The NRG antagonists run on 7.5% SDS-PAGE gel were detected by anti-HA mAb HA.11. Phosphotyrosine mAb 4G10 was used to detect phosphorylated erbB receptor (p185) in L6 cell western blot analysis following resolution on overrun 5% reducing SDS-polyacrylamide gels. The filters were then probed with goat anti-mouse IgG secondary antibody coupled with peroxidase, treated with chemiluminescence reagent (PerkinElmer Life Science, Boston, Mass.) and exposed to X-blue film (Eastman Kodak Co.).

Results

Figure 5A:
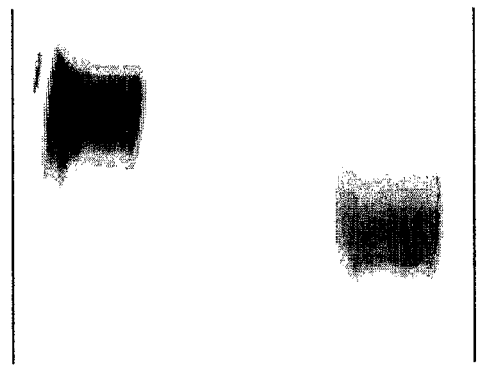
Figure 5B:
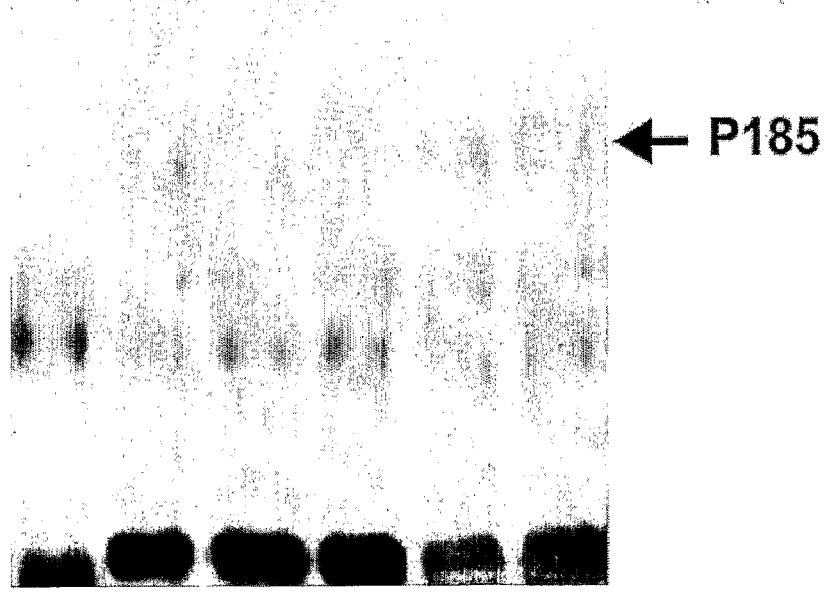

The aim of these studies was to make potent NRG antagonists using the extracellular ligand-binding domain of erbB4 receptor with an added "targeting" HBD domain. In order to follow the expression and purify the antagonist constructs, a 9 amino acid HA tag was introduced at the C terminus of erbB4 constructs in which the erbB4 domains and the HBD were tested in different relative positions. (FIG. 2A). As a control, the ECD of erbB4 was expressed alone without the HBD domain (B4-HA). The other three antagonists were constructed by either adding the HBD domain in N-terminal to (HBD-B4-HA and HBD-S-B4-HA) or C-terminal to (B4-HBD-HA) the dominant-negative erbB4 receptor (B4-HA). The 25 amino acid signal sequence of the erbB4 receptor was maintained at the N-terminus of each recombinant protein because it was known to be truncated during post translational modification. HBD-B4-HA and HBD-S-B4-HA constructs differed by the insertion of natural occurring, glycosylated spacer domain (S) between the HBD and the erbB4 receptor. All NRG antagonist constructs were verified by sequencing.

The four NRG antagonist constructs were stably expressed in HEK293 cells and detected by western blot of culture media using HA antibodies (FIG. 2B). As expected, HBD-S-B4-HA ran at a higher molecular weight of 160-180 kDa, while the other three antagonist proteins were approximately 120-140 kDa. The larger molecular weight of HBD-S-B4-HA was due to additional O-linked and N-linked glycosylation on the spacer region of the N-HBD (Fischbach, G D et al. (1997) *Annu Rev Neurosci* 20:429-458).

The ability of recombinant constructs to bind heparin was tested through HBD/heparin interactions in culture medium. Each construct was applied to a small heparin column. The flow-through as well as the eluate (with increasing salt concentrations) were analyzed by HA western blots as shown in FIG. 3. While the B4-HBD-HA and HBD-S-B4-HA proteins bound the heparin column, the B4-HA and HBD-B4-HA fusion polypeptides did not. The latter may result from the fact that the close proximity of erbB4 domain and the HBD interfere with the tertiary structure or block the positively charged Lys and Arg residues of the HBD domain.

Comparing the two HBD fusion polypeptides that bound heparin, it was evident that HBD-S-B4-HA had a higher binding affinity than did B4-HBD-HA. Higher salt concentrations (>1M) were needed to disrupt HBD-S-B4-HA binding interactions, whereas as little as 0.4-0.5 M NaCl eluted B4-HBD-HA from the heparin column. One explanation for this difference in affinity is that the HA tag in B4-HBD-HA may exert minor effects on the conformation of the HBD even though it consists of only 9 amino acids. A more likely explanation is that the spacer domain optimally separated the HBD from erbB4 to achieve the proper protein folding necessary for heparin binding. After all, in native NRG, the spacer domain is always present between the native HBD and EGF-like domains and thus may be important for proper spatial separation of these domains to support their function (Fischbach et al., supra).

Based on western blot measurements, comparable amounts of NRG antagonist fusion polypeptides were assayed for their ability to block erbB receptor phosphorylation by the IG-EGF form of NRG (p185) in L6 cells (FIG. 4). While B4-HA and HBD-B4-HA had little effect on p185 receptor phosphorylation, both HBD-S-B4-HA and B4-HBD-HA dramatically reduced erbB receptor activation. The HBD-S-B4-HA construct had the greatest effect. This order of potency correlates precisely with the heparin binding activity of the recombinant proteins. It is believed that stronger heparin binding capability localizes more of the recombinant antagonist into the HSPG-rich L6 cell surface where it can compete with endogenous erbB receptors, resulting in greater NRG antagonism.

To obtain more quantitative results and to test these proteins as potential cancer drugs in vivo, recombinant NRG antagonists were prepared with an HIS tag instead of the HA tag at their N-terminus for ease of purification on a Nickel affinity matrix. The silver staining shown in FIG. 5A demonstrates purified HBD-S-B4-HIS (called GlyB4) on the left and B4-HIS (134) on the right. A heparin column was also used to purify the GlyB4 antagonists that also binds to heparin. FIG. 5B shows that pre-incubation with GlyB4 followed by washing produced a sustained disruption of neuregulin signaling measured as phosphorylation of p185. GlyB4 and B4 were preincubated with L6 muscle cells for one hour, then thoroughly washed before adding recombinant neuregulin. Pretreatment with GlyB4 led to complete and sustained blockade of neuregulin signaling, whereas B4 (lacking the HBD), had no sustained effects on neuregulin challenge. FIG. 5C shows that GlyB4 was more effective than B4 at blocking proliferation of MCF10CA1 human breast cancers treated with either no drug (control), GlyB4, B4, or Herceptin® on days 0, 3, and 6. Identical concentrations of 1 nM GlyB4 were significantly more potent at blocking cancer cell growth when compared to growth of control cells or cancer cells treated with B4. GlyB4 was comparably, if not slightly more, effective than a much higher concentration of Herceptin® (100 µg/ml). (See FIGS. 6-11 for additional studies with these human breast and breast cancer cell lines.) FIG. 5D shows four photomicrographs of cells whose growth is described graphically in FIG. 5C. GlyB4 blocks proliferation in part by promoting contact inhibition as can be seen in these photomicrographs of MCF 10CA1 cells grown for 6 days in the presence of medium only (control), B4, GlyB4 and Herceptin®. (Experimental details for working with this human cancer cell line are described in Example II).

One of the most important issues in the treatment of human disease is selective (if possible) delivery of the agent to the targeted diseased tissue. This selectivity is critical not only to achieve sufficient levels of drug for efficacy, but also to minimize unwanted side effects at other sites. This is particularly important in cancer treatment. Recent trials of exogenous proteins such as brain-derived neurotrophic factor (BDNF) and glial cell line-derived neurotrophic factor (GDNF) in the treatment of Amyotrophic Lateral Sclerosis (ALS) have failed because of inadequate targeting to the desired sites of action. The present invention provides a means to target proteins to HSPG-rich cell surfaces using the HBD of NRG. This should also provide a means to bring these and other proteins closer to where they are needed and increase their stability and potency.

In summary, this present study defined the biochemical and biological characteristics of four recombinant NRG antagonists and showed that HBD-S-B4-HA ("GlyB4" (whether using HIS or HA as the "tag") was the most potent antagonist, due in part to its high heparin binding affinity which leads to its concentration on the cell surface through interactions with HSPGs in the ECM. The HBD-containing NRG antagonists are ideal candidates for blocking the autocrine NRG loop. Agents with such capability are expected to be effective breast and ovarian cancer therapeutics.

Example II

Development of an Autocrine Neuregulin Signaling Loop with Malignant Transformation of Human Breast Epithelial Cells Abbreviations Used: NRG, Neuregulin; PBS, Phosphate Buffered Saline; p185, Phosphorylated erbB Receptors; IgB4, Soluble erbB4-Immunoglobulin Fc Fusion Antagonist, EGF, Epidermal Growth Factor This Example helps define the need for targeted NRG antagonists, as it shows that disrupting autocrine neuregulin signaling can reduce the growth rate of human breast cancer cells. The MCF10 series of cells were used to investigate how NRG affects breast epithelial cell growth. Using cDNA microarray analysis, it was shown that that NRG reduces the growth rate of MCF10AT cells that correlates with a marked down-regulation of a group of NRG-response genes, many of which have been shown to up-regulated during cell proliferation. It is shown here that as cells in the MCF10 series become progressively malignant, exogenous NRG treatment of these cells results in a change from anti-proliferative to proliferative effects with the concomitant failure of NRG to down-regulate these genes. Using several different NRG and NRG signaling antagonists, it is demonstrated that malignant progression is associated with the development of a proliferative, autocrine NRG signaling loop, associated with a reduction of erbB3 expression and the over-expression of both erbB2 and NRG.

Materials and Methods

Reagents and cell lines: Insulin and hydrocortisone were purchased from Sigma (St. Louis, Mo.); epidermal growth factor was from Upstate Biotechnology Incorporation (Lake Placid, N.Y.); cholera toxin and AG1478 were purchased from Calbiochem (La Jolla, Calif.). All the other media, buffer and ingredients for cell culture were purchased from Invitrogen Life Sciences (Carlsbad, Calif.). Neuregulin β1 recombinant protein IG-EGF form which corresponds to amino acids 14-276 was provided by Amgen (Thousand Oaks, Calif.). Trastuzumab was a generous gift from Dr. Wei-Zen Wei, (Karmanos Institute, Wayne State University). Phosphotyrosine antibody 4G10 was purchased from Upstate Biotechnology Incorporation (Lake Placid, N.Y.); erbB2 and erbB3 antibodies were from Santa Cruz (Santa Cruz, Calif.); Goat anti-mouse and goat anti-rabbit antibodies were from Chemicon (Temecula, Calif.). Normal breast epithelial MCF10A, pre-malignant MCF10AT and malignant MCF10CA1 cells were provided by the Barbara Ann Karmanos Cancer Institute, Core Cell Facility, Wayne State University). The NRG antagonist IgB4-stablely transfected HEK 293 cells were a gift from Dr. Corfas (Harvard) and the plasmid originally from Dr. Yarden (Weizmann Institute, Israel).

Cell cultures: The MCF10A and MCF10AT cells were cultured in DMEM/F12 media supplemented with 5% horse serum, 10 mM HEPES buffer, 10 ng/ml insulin, 20 ng/ml epidermal growth factor, 100 ng/ml cholera toxin and 0.5 mg/ml hydrocortisone at 37° C. in a 5% $CO_2$ incubator. The MCF10CA1 cells were cultured in just DMEM/F12 media with 5% horse serum in a 5% $CO_2$ incubator. Cells were fed twice a week and passaged on a weekly bases. The L6 cells were cultured in DMEM supplement with 10% fetal calf serum, 1 mM L-glutamine and 1000 U/ml penicillin/streptomycin at 37° C. in a 10% $CO_2$ incubator as described previously. The NRG antagonist IgB4-stably transfected HEK293 cells were cultured in DMEM with 10% fetal calf serum, 1 mM L-glutamine, 2 mM sodium pyruvate, 0.1 mM nonessential amino acid, 1000 U/ml penicillin/streptomycin and selective antibiotic Geneticin 200 µg/ml at 37° C. in a 10% $CO_2$ incubator.

Cell proliferation assays: All three breast epithelial cell lines were plated at 5000 cells/well in 48 well plates in regular MCF10A/AT or MCF10CA1 media. After incubation for 3 days, 1 nM NRG in MCF10A/AT media or just MCF10A/AT media alone were applied to the cells for another 24 hours followed by washing them with culture media and then counting cell numbers using an hemocytometer on the $4^{th}$, $5^{th}$, $6^{th}$, $7^{th}$ and $8^{th}$ day.

RNA preparation and Northern blotting: MCF10A, MCF10AT and MCFCA1 cells were cultured in 25 cm flasks to approximately 60% confluence. The cells were treated with 1 nM NRG in MCF10A/AT media for 24 hours. The cells were then washed with phosphate buffered saline (PBS) once and harvested. Total RNA was extracted from cells using Ultraspec (Biotecx Laboratories, Inc.), "cleaned up" by Rneasy® purification kit (Qiagen, Valencia, Calif.), and subsequently to quantified using a fluorescent dye binding method called Ribogreen (Molecular Probes, Eugene, Oreg.). Northern blots were performed as described previously (Li & Loeb, supra) on RNA extracted from the 3 breast epithelial cell lines after NRG treatment in MCF10A/AT media verses control MCF10A/AT media. Probes were generated by PCR and then prepared by random priming to full-length cDNA clones from the clones provided by Alphagene Inc as described. The membranes were reprobed with a $^{32}$P-labeled GAPDH probe for normalization.

Western blots and L6 muscle assays: P185 receptor phosphorylation of the three cell lines was measured by phosphotyrosine western blots after NRG treatment for 30 min on 3 day old cultures as described in WO 03/012045 and Li Q & Loeb J A (2001) *J Biol Chem;* 276:38068-75. In experiments to block NRG-induced receptor activation, 1 nM of NRG with or without blocking reagents (IgB4, 10 μM AG1478 or 100 μg/ml Trastuzumab) on 3 day old MCF10CA1 cells for 30 min at 37° C. in a 5% $CO_2$ incubator. The media was discarded and phosphotyrosine western blots were performed as above. The membranes were stripped and reprobed with polyclonal rabbit erbB2 for the detection of overall erbB2 protein that was used for quantitation.

Concentrated culture media to assay for NRG from each cell line was prepared on 3 day-old cultures that had been placed in Optimem I (Invitrogen) for an additional 2 day period. The conditioned media was concentrated using a Centricon device (Fisher, Hanover Park, Ill.) at 4° C. At the same time, cell numbers of the 3 cell lines were counted and used to normalize the amount of conditioned media per cell added to the L6 bioassay for quantifying the amount of NRG released into the media.

RT-PCR: 1 μg of total RNA isolated from either MCF10A, MCF10AT, MCF10CA1 cells was used for RT-PCR. The RT-PCRs were performed using Superscript II RT-PCR system (Invitrogen) with the following primers that correspond to the heparin binding domain of human NRG β1 form: forward 5'-CAG GAT CCC AAG AAG GAG CGA GGC TCC-3' [SEQ ID NO:29]; reverse 5'-C GGG ATC CC TAA TTT GCT GAT CAC TTT GC-3' [SEQ ID NO:30]. The cDNAs were resolved on 1% agarose gels and photographed using Polaroid GelCam with Polaroid 667 film (VWR, Chicago, Ill.).

IgB4, AG1478 and Trastuzumab treatments: NRG antagonist IgB4-stablely transfected HEK 293 cells were cultured to 80% confluent before Optimem I was applied to the cells. After 2 days, the Optimem I conditioned media was concentrated by Centricon at 4° C. 40 μl of IgB4 conditioned media or 10 μM of tyrosine kinase inhibitor AG1478 were combined with 150 ml 1 nM NRG in MCF10A/AT media for 15 min at room temperature before being added to MCF10CA1 cells for 30 min treatment. For Trastuzumab experiment, the MCF10CA1 cells were pre-treated with 100 μg/ml Trastuzumab in MCF10CA1 media for 24 hours before the cells were treated with 1 nM NRG in the presence of 100 μg/ml Trastuzumab in MCF10A/AT media for 30 min. The amount of each antagonist was determined empirically based on its ability to block NRG-induced activation of L6 cells.

Results

NRG Changes from an Anti-Proliferative to a Proliferative Factor in the MCF10 Series and Loses its Ability to Down-Regulate Cell Proliferation Genes.

Figure 6A:
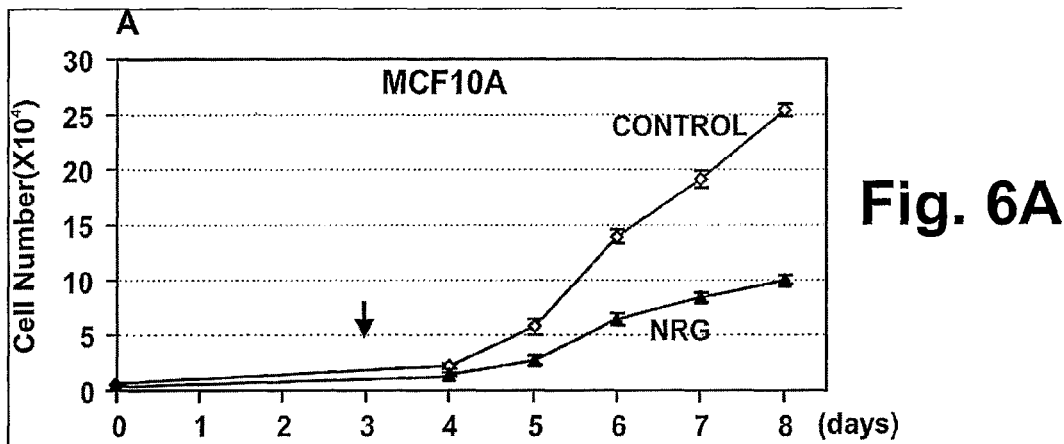
FIGS. 6A-6C. Differential effects of NRG on cell proliferation of breast epithelial cell lines MCF10A (FIG. 6A), MCF10AT (FIG. 6B) and MCF10CA1 (FIG. 6C). Breast epithelial cell lines MCF10A, MCF10AT and MCF10CA1 cells were plated at 5000/well in 48 well plates for 3 days. The cells were then treated with (triangles) or without (diamonds) 1 nM NRG in MCF10A/AT media for 24 hours (arrow) before the cell numbers were counted daily on days 4-8.
Figure 6B:
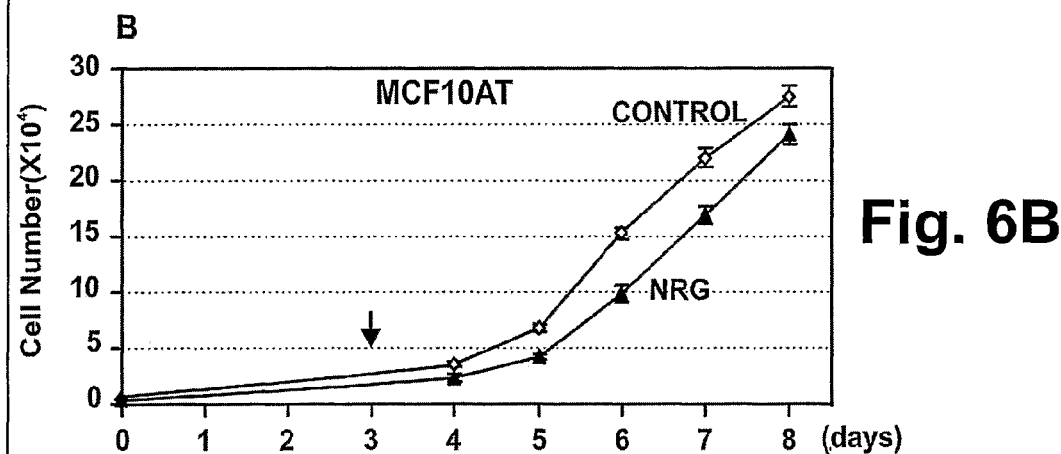
Figure 6C:
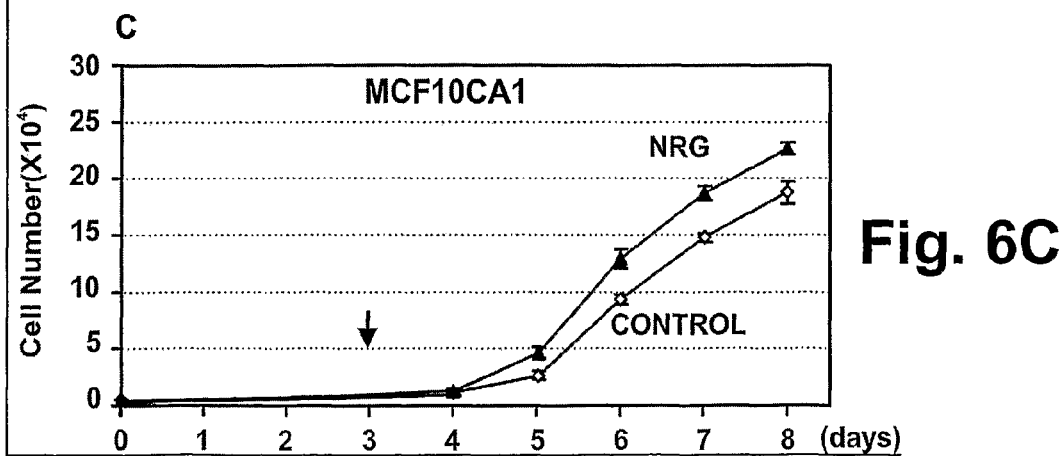

The effect of NRG on the proliferation rate of the MCF10 series of cell lines was examined with MCF10A, MCF10AT and MCF10CAL grown in serum-containing media (FIG. 6A-6C). Three days after plating, 1 nM NRG treatment for 24 hours produced a sustained reduction in the growth rate of the MCF10A cells. In contrast, NRG treatment increased the initial growth rate of the more malignant MCF10CA1 cells. NRG treatment of the MCF10AT cells was in between with only a small, initial reduction in growth rate. These results demonstrate a gradual transition on the effects of NRG on the growth of MCF10 cells that switches from an anti-proliferative to a proliferative effect as the cells become more malignant.

Figure 7A:
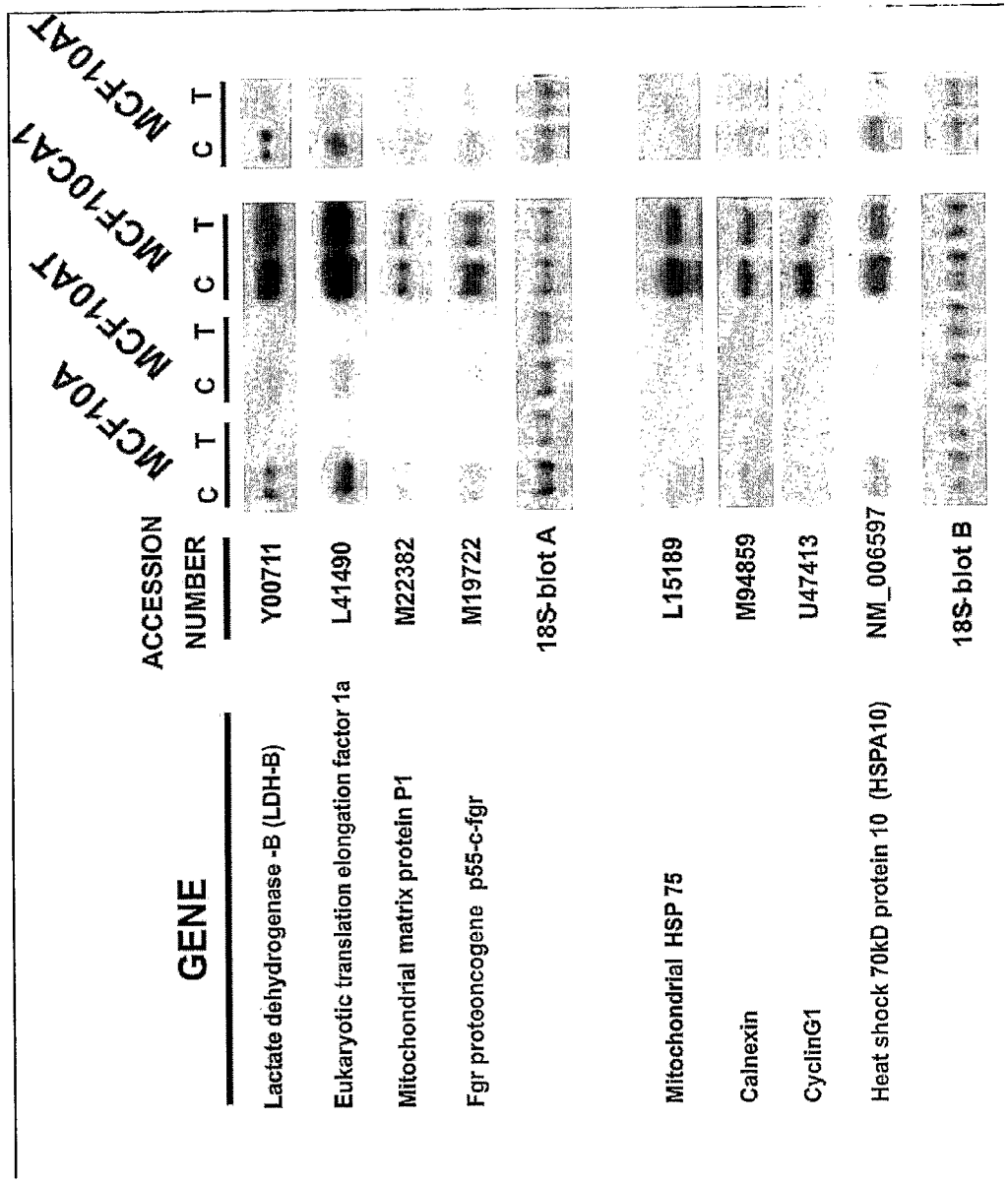
FIGS. 7A-7B. NRG treatment differentially regulated expression levels of eight "proliferation" genes in the three cell lines.
Figure 7B:
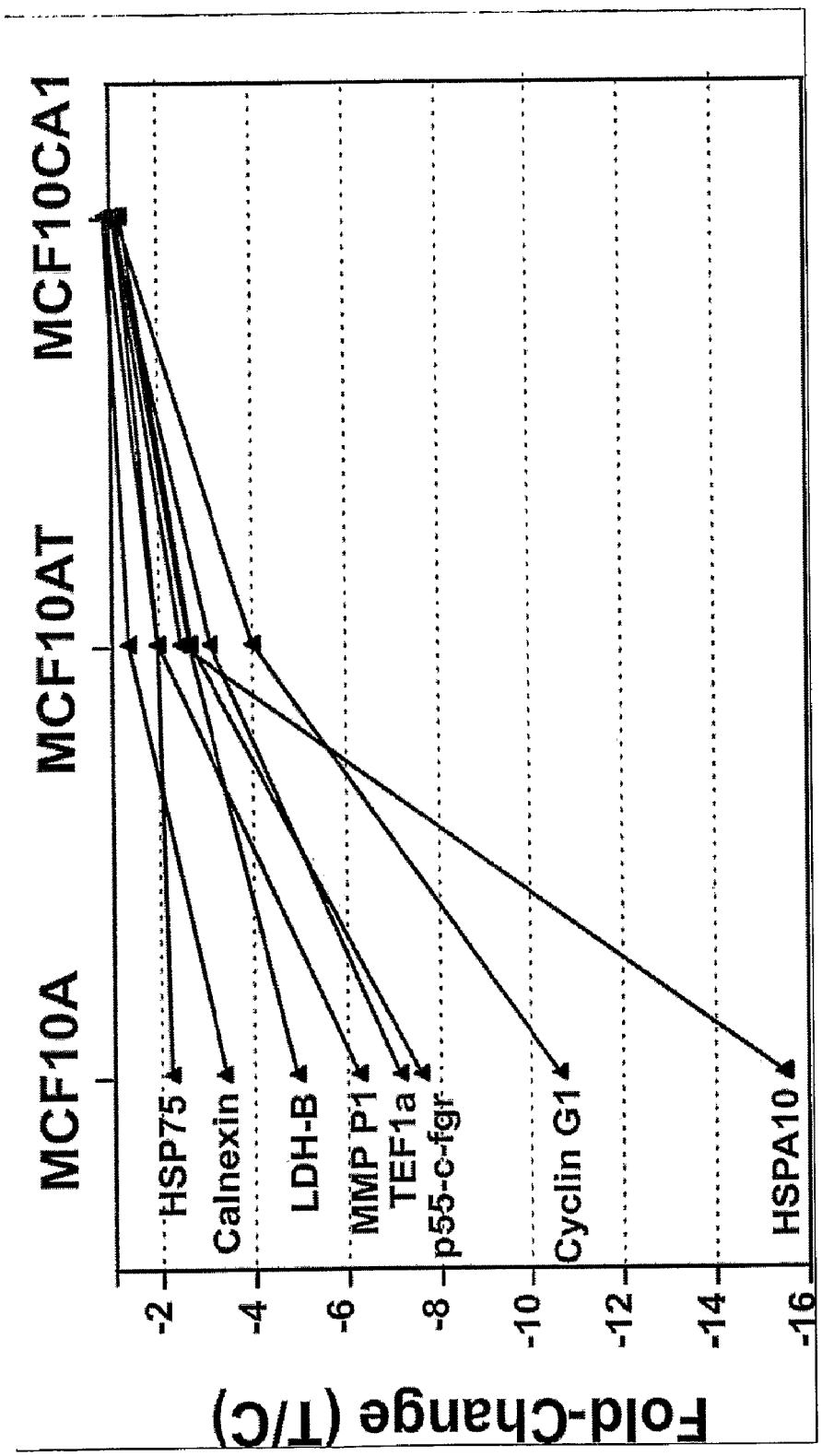

Cell growth is a complicated process that involves many genes. The inventor's group has recently used cDNA microarrays with northern blot confirmation to identify a group of NRG-response genes that were coordinately down-regulated in the first 24 hours of NRG treatment of the MCF10AT cells[3]. Many of these genes could be considered "proliferation" genes and include several oncogenes, cell cycle control genes, and cell proliferation genes. A representative group of 8 of these NRG-response genes that changed in response to NRG treatment was selected for testing with each of the three MCF10 cell lines (FIG. 7A-7B). Northern blots were performed on total RNA isolated from each cell line treated with or without 1 nM NRG for 24 hours. Without NRG treatment, the most malignant cell line MCF10CA1 expressed these genes at the highest baseline levels compared to the MCF10A cells, while the MCF10AT cell expressed them at the lowest levels thus requiring longer exposures (shown on the right side of FIG. 7A). NRG treatment produced a rapid down-regulation of all 8 of these genes to varying degrees in both the MCF10A and MCF10AT cells, however, as shown in FIG. 7B, the effect was significantly greater for the MCF10A than for the MCF10AT cells. This is consistent with NRG's effects on cell proliferation above where NRG had only transient effects on the MCF10AT cells. In contrast, there was very little down-regulation of only a few of these genes in the MCF10CA1 cells that increased their proliferation rate with NRG treatment. Thus, proliferation genes are both basally upregulated and are no longer effectively down-regulated by NRG in the more malignant MCF10CA1 cells, despite growing at a similar rate as the other cell lines (see FIG. 6A-6C). These results raise an important mechanistic question as to how signaling by the same growth factor leads to such different effects on cell proliferation in the MCF10 cell line series. The NRG Proliferation Response Correlates with Increased Expression of erbB2, Decreased Expression of erbB3, and Increased Secretion of Endogenous NRG.

One possibility is that differential erbB receptor expression and/or activation may contribute to the different responses to NRG in the MCF10 cell line series. In fact, MCF10A cells that over-express erbB2 are more sensitive to the mitogenic effects of NRG (Ram T G et al. (1995) *J Cell Physiol;* 163: 589-596). The degree of NRG-induced receptor tyrosine phosphorylation (p185) was therefore measured using a phosphotyrosine antibody and the relative abundance of erbB2 and erbB3 that can form active receptor heterodimers in MCF10A, MCF10AT and MCF10CA1 cells. Since p185 can be composed of multiple erbB receptors, the phosphotyrosine western blot in FIG. 8A was re-probed with specific antibodies to erbB2 (FIG. 8B) and erbB3 (FIG. 8C). The upper band (p185) consisted of predominantly erbB2 and erbB3. While the lower band contained a lesser amount of erbB3 immunoreactivity, its major constituent is erbB1 (EGF receptor; not shown) that remains phosphorylated in all three cell lines in the absence of NRG treatment. Given that the erbB receptors heterodimerize with one another, immunoprecipitation of individual receptor subtypes is not possible without brining down the others.

All three cell lines responded to NRG by inducing p185 phosphorylation, however, erbB receptors in the MCF10AT and MCF10CA1 were phosphorylated even without exogenous NRG treatment. Furthermore, while exogenous NRG treatment induced strong erbB receptor phosphorylation in both MCF10A and MCF10AT cells, only a small incremental amount of phosphorylation could be detected above the high basal levels in the MCF10CA1 cells (FIG. 8A; see also FIGS. 10A-10C & 12A-12C that show the small effect of NRG on MCF10CA1 cells more clearly). When reprobed with erbB2 antibodies, increasing levels of erbB2 were seen during the transition from normal breast epithelial MCF10A cells, to pre-malignant MCF10AT cells, and to malignant MCF10CA1 cells (FIG. 8B). At the same time erbB2 expression increased, erbB3 expression went down in the MCF10AT and MCF10CA1 cells (FIG. 8C). Specifically, the ratio of erbB2/erbB3 in the MCF10A compared to the MCF10CA cells changed from 0.29±0.08 to 2.7±0.45. No erbB4 receptors could be detected in these cell lines using the antibodies tested above (from Santa Cruz).

Figure 9A:
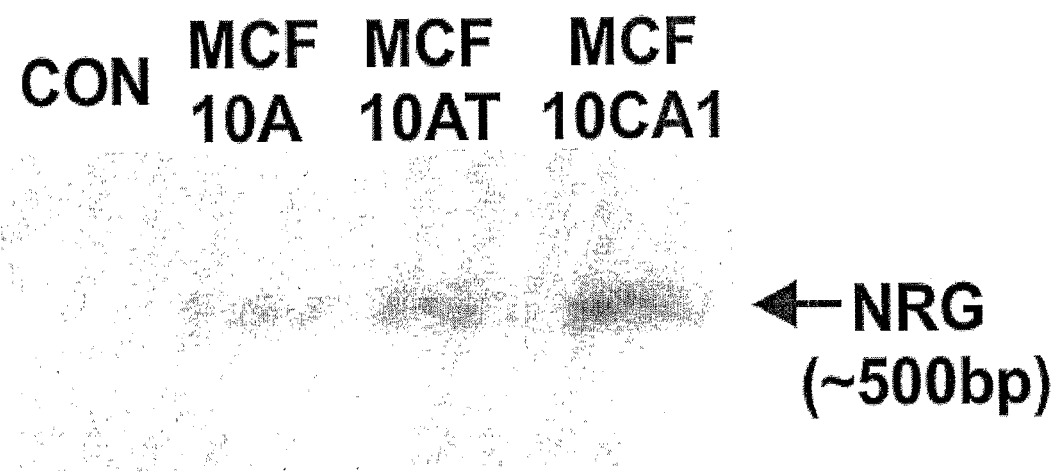
FIG. 9A-9B. Endogenous NRG expression was increased in MCF10 cell lines during the transformation from normal to malignant phenotype.
Figure 9B:
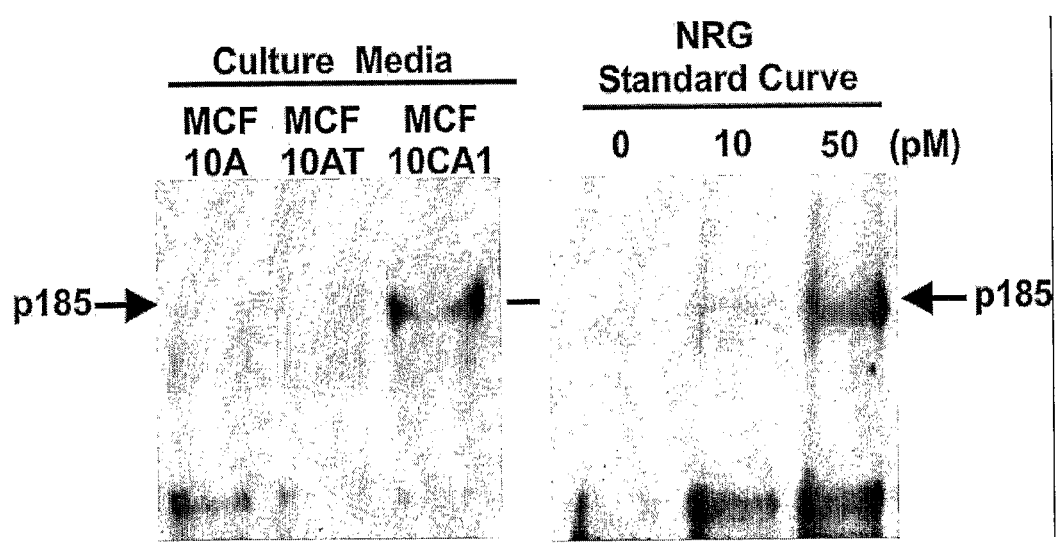

The presence of high basal levels of p185 receptor phosphorylation in the absence of exogenous NRG in the malignant cell lines raises the possibility that these cells secrete NRG that, in turn, activates the erbB2 and erbB3 receptors in an autocrine pathway. To test for the presence of NRG, RT-PCR of MCF10A, MCF10AT and MCF10CA1 cells was performed using a specific primer pair to the heparin-binding domain of human NRG (FIG. 9A). This domain is expressed in all soluble forms of NRG (Falls D L (2003) *Exp Cell Res* 284:14-30). While not quantitative, these results suggest that increasing levels of NRG are expressed as the breast epithelial cells become more malignant cancer cells. The amount of NRG activity released into the conditioned media from equivalent numbers of each of the three cell lines was measured using the L6 muscle cell line as a sensitive means to measure soluble NRG activity through p185 receptor phosphorylation (Corfas et al., supra). FIG. 9B shows that the amount of NRG activity in conditioned media from each of the three cell lines increased significantly as the cells become more malignant. This increase paralleled their degree of basal p185 phosphorylation suggesting that endogenous NRG production is responsible for high basal levels of erbB receptor phosphorylation in the more malignant cells.

Existence of an Autocrine Loop can be Revealed by NRG Antagonists.

The results reported above are consistent with the notion that, as the MCF10 cells become more malignant, they develop an autocrine NRG signaling loop that promotes cell proliferation. Blockade of this autocrine loop in the highly malignant MCF10CA1 cells, was therefore expected to reduce the cells' proliferation rate. NRG signaling was blocked using three complementary approaches: (A) By blocking endogenous NRG from activating cell-surface erbB receptors using a soluble erbB4 receptor antagonist called IgB4 which comprised the ECD of erbB4 fused to an Ig Fc domain to produce an antagonist that works by competing with cell-surface receptors for soluble NRG released into the culture media; (B By blocking erbB receptor signaling pharmacologically using the erbB-receptor specific tyrosine kinase inhibitor AG1478 (Levitzki A et al. (1995) *Science* 267:1782-88); and (C) By down-regulating erbB2 receptors with a specific mAb such as the commercially available mAb Trastuzumab or Herceptin® (currently in clinical use).

In MCF10CAL cells, IgB4 effectively blocked both the high basal levels and exogenous NRG-induced p185 receptor phosphorylation (FIGS. 10A-10B). IgB4 not only blocked MCF10CAL cell proliferation induced by exogenous NRG treatment, but also significantly reduced the baseline growth rate of these cells (no NRG treatment added) (FIG. 10C). Thus, endogenous NRG production is not only responsible for activating basal levels of erbB receptor phosphorylation, but directly induces MCF10CAL cell proliferation. The tyrosine kinase inhibitor AG1478 blocked NRG-induced erbB signaling, reducing both p185 (erbB2/3, upper band) and EGF receptor phosphorylation (lower band) in a dose dependent manner (FIGS. 11A and 11B). Similar to the IgB4, at an effective concentration of 10 μM, AG1478 reduced the growth rate of the MCF10CA1 cells, both with and without exogenous NRG (FIG. 11C). Finally, when pre-treated with Trastuzumab, the basal levels of erbB receptor phosphorylation in MCF10CA1 cells were not affected. However, the response to exogenous NRG was reduced (FIGS. 12A-12B). Consistently, although Trastuzumab reduced cell proliferation in response of exogenous NRG, it had no effect on proliferation in the absence of exogenous NRG (FIG. 12C).

Taken together, these results indicate that while the most effective way to block both NRG signaling and growth promotion is by disrupting an autocrine loop by reducing extracellular NRG with a soluble antagonist, such as the hybrid fusion polypeptide of the present invention, blocking downstream events—erbB receptor phosphorylation or cell-surface expression of erbB2—also reduce MCF10CA1 cell proliferation.

Discussion of Example II

Figure 13:
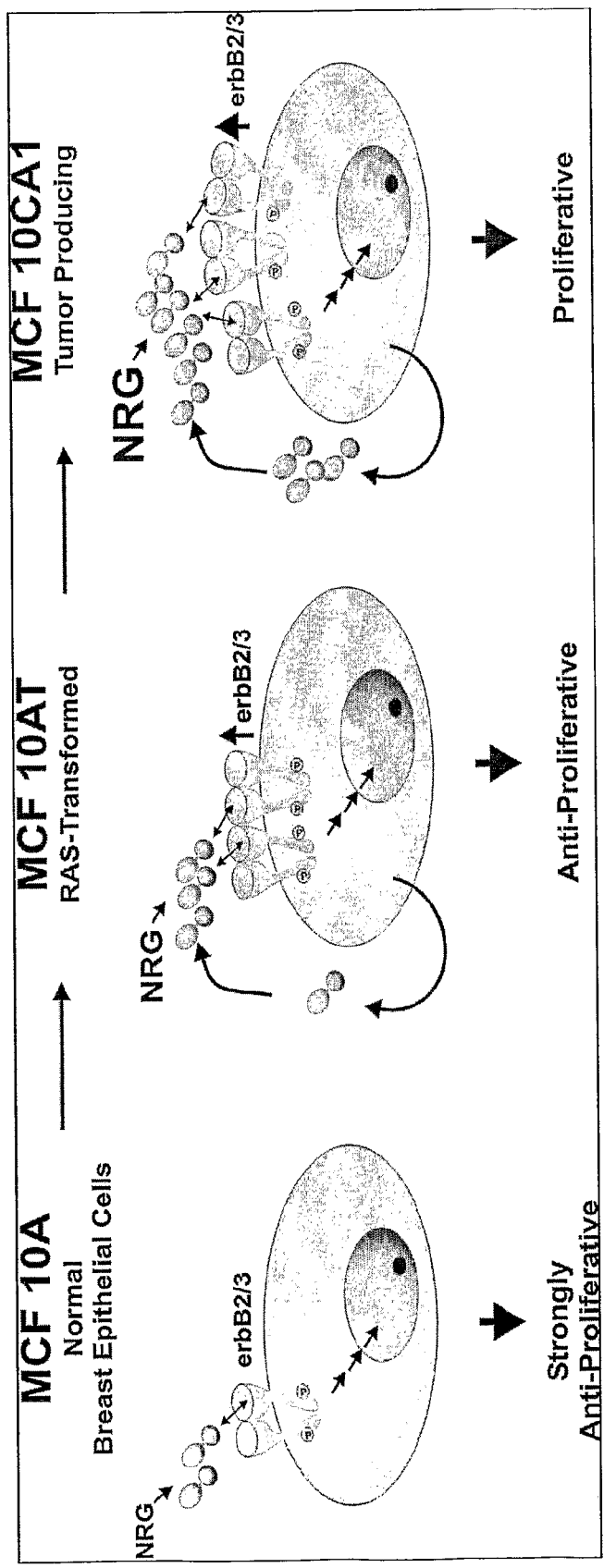
FIG. 13 is a schematic illustration summarizing NRG signaling and actions in the MCF10 series of breast epithelial cells. As the cells progress from normal MCF10A to pre-malignant MCF10AT to highly malignant MCF10CA1 cells, the effect of exogenous NRG switches from anti-proliferative to proliferative. This switch is associated with an increase in the expression ratio of erbB2 to erbB3 receptors that form heterodimers with each other and a marked elevation of endogenous NRG production. This produces an autocrine signaling loop that can be blocked in a number of different ways to reduce their proliferation rate. NRG is shown as having both an heparin-binding domain (lighter sphere) and receptor-binding EGF-like domain (darker sphere).

This example shows that progressive malignant transformation of the MCF10 cell line is associated with a loss of NRG's normal anti-proliferative effects and the development of an autocrine NRG signaling loop that stimulates cell proliferation. The MCF10 cell series covers the whole spectrum of tumorigenesis from the fairly normal MCF10A cells, to the pre-malignant MCF10AT cells, to the highly malignant MCF10CA1 cells in a single, isogenic series. Effects of exogenous NRG on this series of cell lines "switched" from anti-proliferative to proliferative as the cells changed from normal to malignant. This was associated with an relative increase in erbB2 and decrease in erbB3 expression. Since erbB2 cannot bind NRG and erbB3 has an inactive tyrosine kinase domain, the change in proportion of erbB2/3 could significantly alter NRG binding to erbB3 and signaling through erbB2. While the mechanism for this change in NRG responsiveness may stem from changes in erbB receptor subtype expression, it may also have resulted from markedly higher levels of endogenous NRG secretion that produce a high basal level of erbB receptor activation through an autocrine signaling loop (FIG. 13). Consistently, disrupting this autocrine loop by several different approaches effectively reduced both sustained erbB receptor activation and the rate of cell growth.

Exactly what leads to this "switch" of NRG from an anti-proliferative to a proliferative factor as these cells become more malignant is not clear. Since the MCF10AT cells were derived by ras transformation of the MCF10A cells, activating the ras oncogene may be necessary, but not sufficient for the preneoplastic phenotype (Wang B et al. (1997) *Anticancer Res* 17:4387-94; Miller F R et al. (1996) *Anticancer Res* 16:1765-69). An increase in the ratio of erbB2 to erbB3 could produce an altered receptor phosphorylation response resulting in a change in signaling pathways that could promote cell proliferation and/or suppress the normal anti-proliferative effects of NRG. Consistent with this later possibility, "NRG response" genes increased normally during periods of cell proliferation are down-regulated by NRG in MCF10A and MCF10AT cells, but expressed at high basal levels and resistant to NRG in the more malignant MCF10CA1 cells. These genes were recently identified in a microarray screen of MCF10AT cells treated with NRG for 24 hours. They include heat shock genes, oncogenes and cell cycle control genes often seen to be highly expressed in malignant, rapidly proliferating cells. Despite the basal upregulation of these "proliferation" genes, MCF10CAL cells do not grow appreciably faster than the MCF10A and MCF10AT cells.

The difference in NRG's effects on the growth of the malignant MCF10CA1 cells could also be due to a marked elevation in endogenous NRG secretion producing sustained, basal erbB receptor phosphorylation levels. Sustained receptor activation may result in part from the accumulation of secreted NRG in the ECM. Using RT-PCR, it was found that the MCF10 cell series express NRG isoforms containing a HBD (Falls, supra. Loeb J A. (2003) *J Neurocytol* 32:649-64). This HBD has been shown to restrict NRG to the ECM of various cells during development and significantly potentiates its biological activities (Loeb J A et al., 1995, supra; Li and Loeb, supra; Loeb J A et al., 1999, supra). Most previous studies used recombinant NRG forms that lack this HBD. In contrast, the present study used a naturally-occurring form of NRG that includes the JBD and thus would be expected to produce more sustained signaling responses. through matrix interactions This may be why others have observed proliferative effects of NRG on MCF10A cells whereas clear antiproliferative effects were found here (Ram et al., supra; Mincione G et al. (1996) *J Cell Biochem* 1996; 60:437-46). Another important difference between this study and those earlier studies that focused on growth factor-dependence is that they used serum-free, defined medium, whereas the present studies were done in medium that included serum as well as EGF and insulin in an effort to provide a more physiological basal background upon which to measure the growth effects of NRG.

Sustained signaling may be one way by which cells can decide to proliferate or differentiate based on the length of time they are exposed to a given growth factor. The present inventor (and colleagues) previously showed in muscle cells that a minimum of 8 hours of constant receptor activation is required for NRG-induced expression of AChRs (Li & Loeb, supra). In other systems, sustained receptor activation utilizes different signaling pathways that lead to different biological effects than those produced by transient receptor activation (Frohnert P W et al. (2003). *Glia* 43:104-18; Shah B H et al. (2003) *J Biol Chem* 278:19118-26; Liu F C et al. (1996) *Neuron* 17:1133-44). In the MCF10A series of cells, sustained erbB receptor activation may thus be important for the switch of NRG effects from differentiation to proliferation— an activity that can be blocked by disrupting NRG signaling in the most malignant cell line using compositions disclosed herein.

Autocrine loops for NRG signaling have been described previously in breast cancer cell lines (Peles E et al. (1992) *Cell* 69:205-16; Lupu R et al. (1996) *Breast Cancer Res Treat* 38:57-66; Mincione G et al., supra) and in cancer cells originating from other epithelial tissues. For example, endogenous NRG production has been found in a majority of ovarian cancer cancers and in colon cancer cells with both inhibition of apoptosis and cell growth that can be blocked by NRG or erbB receptor antibodies (Gilmour et al., supra; Venkateswarlu S et al. (2002) *Oncogene* 21:78-86). The development of a proliferative NRG autocrine signaling loop in the MCF10 series opens the opportunity to employ agents that specifically disrupt this autocrine loop, such as the present compositions, for effective therapy of cancer. A different type of agent, an NRG antisense cDNA that blocks endogenous NRG expression in MDA-MB-231 cells, successfully suppressed the aggressive and invasive phenotype of these cancer cells (Tsai M S et al. (2003) *Oncogene* 2003; 22:761-68).

One difficulty with many specific receptor tyrosine kinase inhibitors of (as well as the erbB-specific tyrosine kinase antagonist AG1478 used above) is a lack of specificity for NRG ligands. AG1478 not only blocks tyrosine phosphorylation of the erbB2 and erbB3 receptors, but also of the EGF receptor. Trastuzumab is a humanized mAb that binds to erbB2 and is currently used clinically in patients that overexpress erbB2. Trastuzumab had minimal effects on (a) blocking exogenous NRG-induced p185 receptor phosphorylation of MCF10CA1 cells even after 24 hours of pretreatment, and (b) reducing proliferation. Another mAb, 2C4, that works by blocking the association of erbB2 and erbB3, inhibits ligand activated erbB2 signaling and cell growth regardless of the expression level of erbB2 protein, but has no growth inhibition without exogenous ligand stimulation (Agus D B et al. (2002) *Cancer Cell* 2:127-37)

In summary, the present results suggest that sustained erbB receptor activation through the autocrine effects of NRG is a key promoter of cell proliferation and may be part of a developmental program in breast epithelial cells that produces a malignant phenotype where proliferation genes are chronically up-regulated. The present results therefore indicate that a focused approach that specifically disrupts NRG signaling, such as by using the fusion polypeptides of the present invention that include N-HBDs as HSPG-targeting domains and B4D as a targeted domain, are useful against various classes of cancer cells in which interruption of NRG autocrine signaling is inhibitory. Treatment with the present pharmaceutical compositions is expected to inhibit tumor growth and metastasis.

Example III

Specific Structural Features of Heparan Sulfate Proteoglycans Potentiate Neuregulin-1 Signaling This Example defines specific structural features required for NRG1-heparin interactions and shows the physiological importance of these features in vitro. A clear hierarchy of importance for specific sulfate groups is demonstrated, with the N-sulfate group most important followed by 2O- and 6O-sulfate groups for binding to NRG1 and blocking erbB receptor phosphorylation. Consistently, removal of all endogenous sulfate groups with chlorate or selective blockade of N-sulfation with an siRNA directed against the enzyme that promotes N-sulfation resulted in decreased NRG1-induced erbB receptor activation. This specificity provides a means by which tissues can localize and potentiate NRG1 signaling through modifications in GAG composition.

Experimental Procedures

Reagents—Recombinant human NRG1 β1 polypeptides were from R&D (Minneapolis Minn.). The isolated EGF-like domain corresponds to amino acids 177-246, and the intact IgEGF form of NRG1 corresponds to amino acids 14-246. Sodium chlorate was purchased from Sigma. The heparan sulfate antibody, 10e4, was from Seikagaku (Japan). De-N sulfated, De-2O sulfated, and De-6O sulfated heparins were prepared as described previously (Ostrovsky, O et al. (2002) *J Biol Chem* 277"2444-53). Different sized heparin fragments from 12 to 2 disaccharides in length were prepared by high resolution gel chromatography of low molecular weight heparin as described previously (Goger, B et al. (2002) *Biochemistry* 41:1640-46). For all experiments, the heparins were used at equal weight/volume (μg/ml) concentrations.

Cell Cultures and Western Blots for p185 phosphorylation—L6 Cells were used to quantify erbB receptor phosphotyrosine (p185) as described (WO 03/012045; Li & Loeb, supra). Cells were plated at 50,000 cells/well and grown for 8 days. Chlorate was filter sterilized and incubated with L6 cells for 2 days prior to the assay. Inhibition assays of p185 were performed by pre-incubating 75 pM of IgEGF NRG1 and various concentrations of the heparins at room temp for 20 minutes. 150 µL of this mixture was then applied to 8 day-old L6 cells for 45 minutes at 37° C. in 110% $CO_2$. The medium was aspirated, and the cells were solubilized in 50 µL sample buffer and boiled for 5 minutes as described previously (WO 03/012045; Li & Loeb, supra) 15 µL of this was resolved on a 5% denaturing polyacrylamide gel. Phosphorylated forms of the erbB receptors (p185) were detected by western blot analysis using the phosphotyrosine monoclonal antibody 4G10 (Upstate) and then verified and quantified by reprobing with a mixture of antibodies against erbB2 (Neomarkers Ab-17) and erbB3 (Neomarkers Ab-6). Quantitation was performed by determining the ratio of p185/(erbB2+erbB3) using Metamorph Imaging System (Universal Imaging Corp) on non-saturated images as described (Esper, R M & Loeb, J A (2004) J Neurosci 24:6218-27)

Gel Mobility Shift Assay (GMSA)—NRG1 alone, or NRG1 plus various heparins at various concentrations were incubated with binding buffer (2.7 mM KCl, 4.3 mM $Na_2HPO_4$, 10 mM $MgCl_2$, 1.4 mM $KH_2PO_4$, 12% glycerol, 1 mM DTT.) for 20 minutes and run on a 6% (29:1 acrylamide:bis) non-denaturing gel (10 mM Tris (pH 7.4), 1 mM EDTA) for 20 minutes at 200 V as described (Wu, Z L et al. (2002) FASEB J 16, 539-45; Wu, Z L et al. (2003) J Biol Chem 278:17121-29). While, the electrophoresis buffer consisted of 40 mM Tris (pH 8.0), 40 mM acetic acid, 1 mM EDTA, changing this to pH 9.0 above the isoelectric point of NRG1 (pI 8.8) did not appreciably change the mobility of NRG1 with or without added heparin. However, band resolution was sharper at pH 8.0 and was therefore used for our studies here. Protein was transferred to a polyvinylidene fluoride membrane (Millipore corp.) for 1 hr at 100V. NRG1 bands were detected by western blot analysis using a polyclonal rabbit antiserum (AD03) developed against the IgEGF polypeptide (Assay Designs Inc.). The filters were then probed with a goat anti-rabbit antibody coupled to peroxidase (Chemicon), exposed to X-blue film (Eastman Kodak Co.) after treatment with chemiluminescence reagents, and bands were quantified as above.

siRNA Silencing—siRNA molecules were designed with online software from Qiagen using the entire rat NDST-1 cDNA sequence (GenBank # M92042). The target sequence of 1406 to 1427 was chosen because of a 19 out of 21 base pair identity to NDST-2. 24 h after plating, L6 cells were incubated with either 2 µg NDST siRNA or random non-silencing siRNA (Qiagen) in 12 µL suspension buffer diluted to 200 µL of L6 media. The cells were then incubated at 37° C. for 3 days and either treated with NRG1 for 45 minutes followed by phosphotyrosine western blot as above. Parallel siRNA treated cultures were used to document reduced NDST mRNA levels by quantitative real-time RT-PCR and sulfation activity by immunostaining with an N-sulfate-specific antibody. Total RNA was isolated using the RNeasy kit from Qiagen according to the manufacturer's instructions. In order to reduce genomic DNA contamination, the column was treated with DNase (137.5 µg/ml) for 15 minutes. The concentration of mRNA eluted from the column was measured using the Ribogreen kit (Molecular Probes), and 1 µg RNA from each sample was reverse transcribed using Superscript II (Invitrogen). The following primers were designed using Primer Express software against NDST-1:

```
primer set 1
                                      [SEQ ID NO: 31]
    forward 5' GAG GAC AAA CGC CAC AAA GAC 3'

[SEQ ID NO: 32]
    reverse 5' GGG CTG TGG TGC CTG TTT T 3';

primer set 2
                                      [SEQ ID NO: 33]
    forward 5' CCA GCT CCG AGA CCT TTG AG 3'

[SEQ ID NO: 34]
    reverse 5' GTG TTG GAG GGA ATA GGG AAG A 3' primer set 3
                                      [SEQ ID NO: 35]
    forward 5' AAA GTG ATG GAC ACA GTG CAG AA 3'

[SEQ ID NO: 36]
    reverse 5' GCT GGC ACC AAA ATC CTT TC 3'

GAPDH
                                      [SEQ ID NO: 37]
    forward 5' AGT ATG ACT CTA CCC ACG GCA AGT 3'

[SEQ ID NO: 38]
    reverse 5' TCT CGC TCC TGG AAG ATG GT 3'
```

Each of these primer sets produced a single band of the correct size of ~100 bp. Amplitaq Gold® polymerase (Promega) with the following cycling parameters was used: 95° C. for 10 minutes, followed by 40 cycles of 95° C. for 15 seconds, 60° C. for 10 seconds, 72° C. for 50 seconds. For real-time quantitative PCR, the SybrGreen® system (Molecular Probes) was used on an MJ Research Opticon Machine and calculated the change in gene expression relative to GAPDH for each sample as described (Esper & Loeb, supra). Immunostaining was performed on L6 cells plated at 50,000 cells/well on an 8-well Flexiperm® chamber and fixed with 4% paraformaldehyde for 15 min at RT. After washing 3× with PBS cells were blocked for 40 minutes with 0.1% Triton-X 100, 2% goat serum, in PBS and then incubated with the 10e4 antibody at 1:30 dilution in the block buffer overnight at 4° C., washed 3×5 minutes in PBS, then visualized with Alexa 546 goat-anti mouse IgM (Molecular Probes) at 1:300 for 2 hr at RT using a Nikon Eclipse 600 epifluorescence microscope with a Princeton Micromax cooled CCD camera. Quantitation of fluorescence was performed using Metamorph software (Universal Imaging) in a similar manner as described previously (Esper et al., supra). The entire fields of three separate pairs of NDST-1 siRNA and control siRNA treated cells from 8-well Flexiperm®r chambers were compared after subtracting the background of nearby regions without cells. siRNA treated cells were reduced to 39, 43, and 60% of the values from control treated cells. This gave an average of 47±11% reduction relative to the control. (The error represents one standard deviation.)

Results

Specific Heparin Sulfate Groups are Required for NRG1 Binding

Figures 14A, 14B:
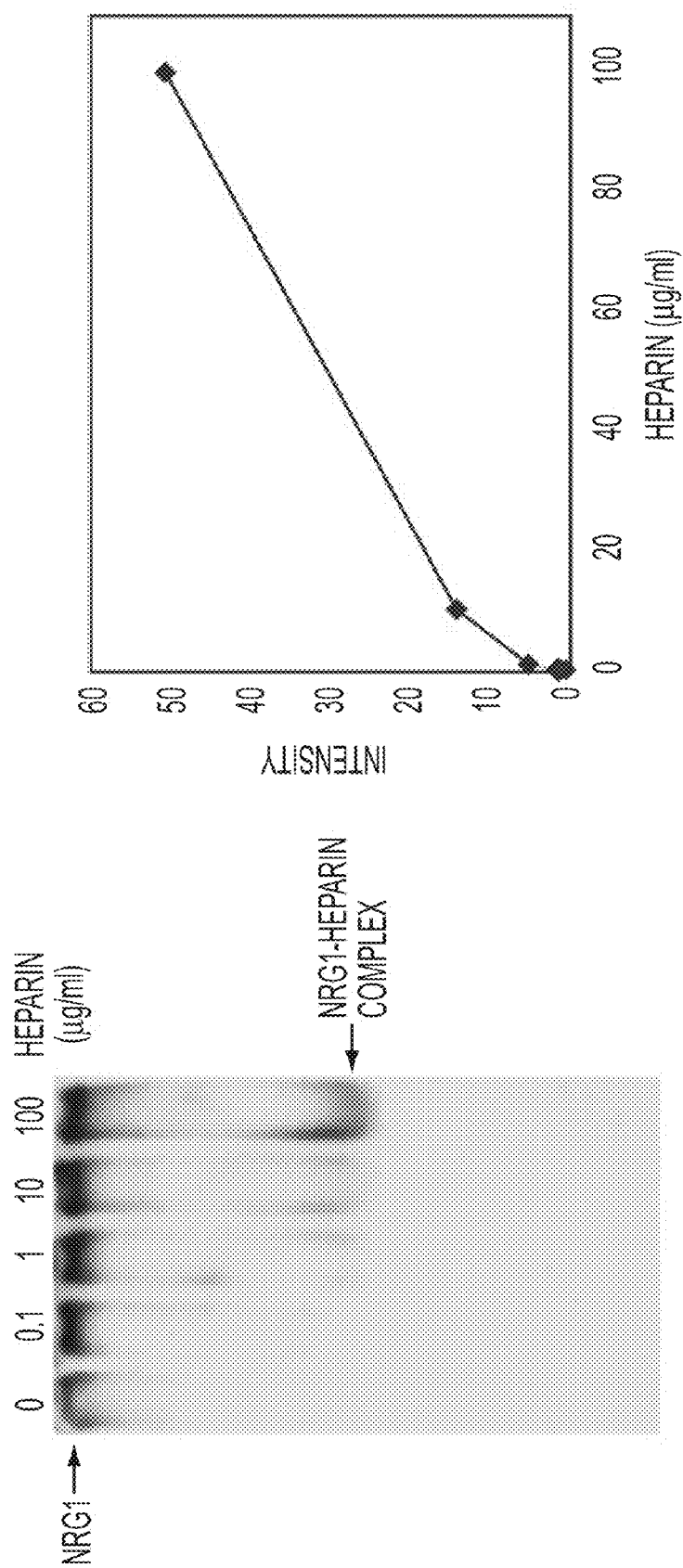
FIG. 14A-14B shows that heparin binds and shifts the position of NRG1 in a gel in a dose-dependant fashion.

A set of chemically modified heparins was prepared that lacked either all sulfate groups (completely desulfated), the N-sulfate groups (De-N sulfated), the 2O-sulfate groups (De-2O sulfated), or the 6O-sulfate groups (De-6O sulfated) in order to assess their importance in heparin-NRG1 interactions using a GMSA modeled after that described by Rosenberg and colleagues (Wu et al., supra). Heparin oligosaccharides were chosen since they are more highly and uniformly sulfated, but have a high degree of structural similarity to the endogenous, cell-surface heparan sulfates (Honke, K et al. (2002) Med Res Rev 22:637-54). This GMSA utilizes a non-denaturing polyacrylamide gel, which separates protein/oligosaccharide complexes based on their charge to mass ratio and conformation. The buffer conditions were optimized so that NRG1 (pI 8.8) was close to a net neutral charge resulting in minimal mobility in the charged field (FIG. 14A). However, when complexed with heparin, NRG1-heparin complexes migrated further and demonstrated a "shift" in the mobility of NRG1 by western blot. FIG. 14A shows that increasing concentrations of heparin shift NRG1 in a dose-dependent manner that is quantified in FIG. 14B.

Figure 15A:
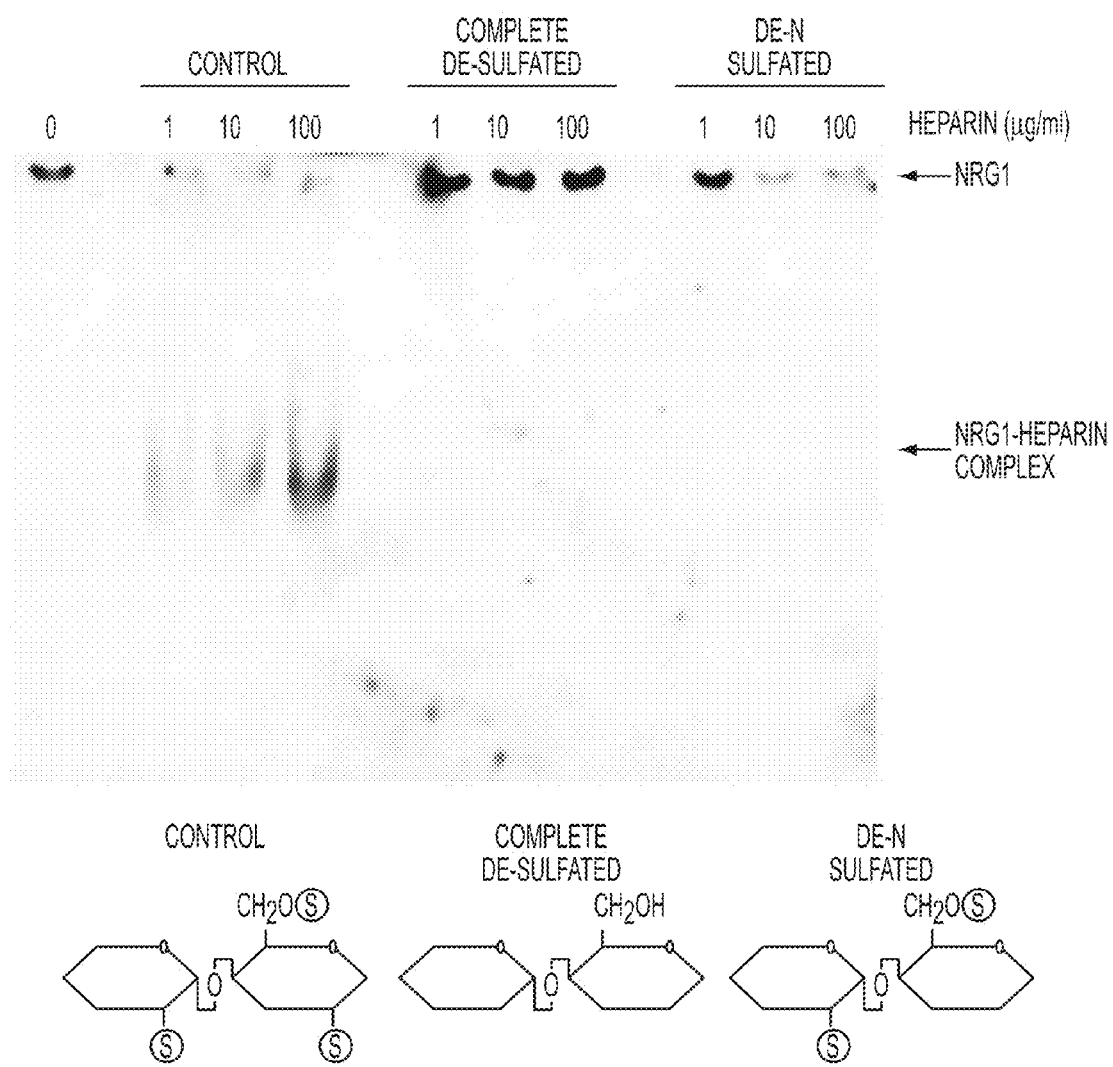
Figure 16A:
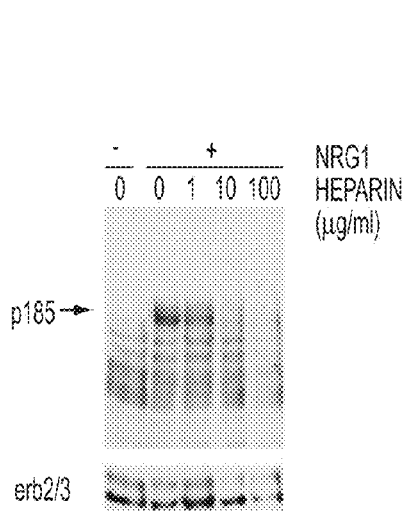
FIG. 16A-16C shows that N-sulfation is more important for inhibiting NRG1 induced erbB phosphorylation than 2O- and 6O-sulfation.
Figure 16B:
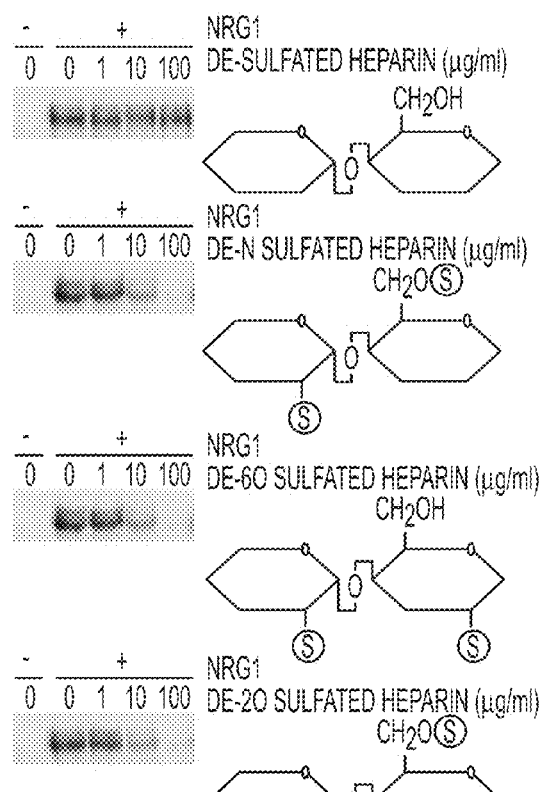
Figure 16C:
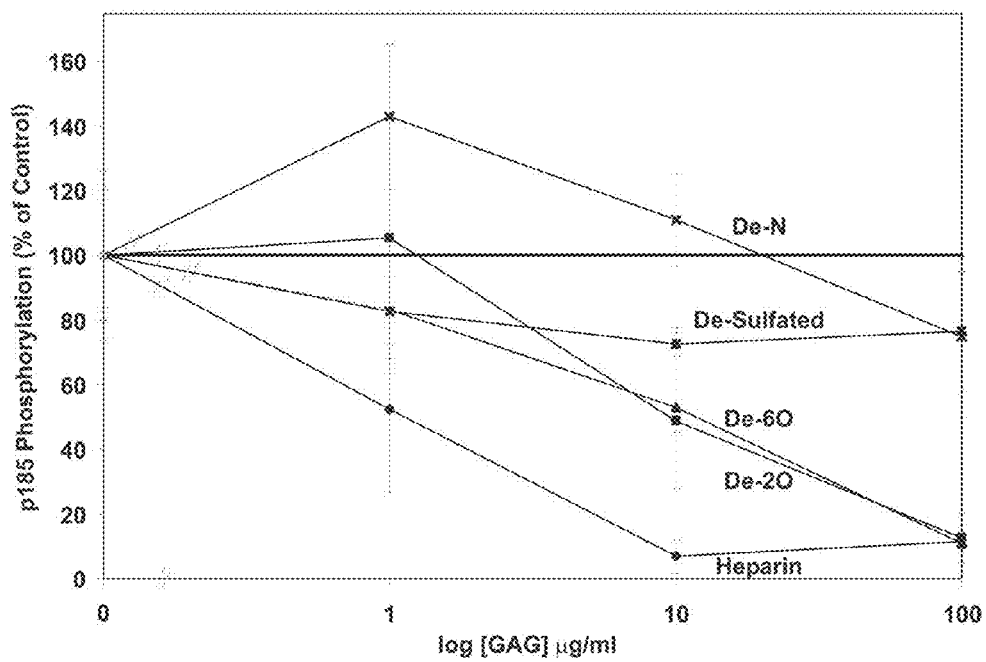
Figure 17A:
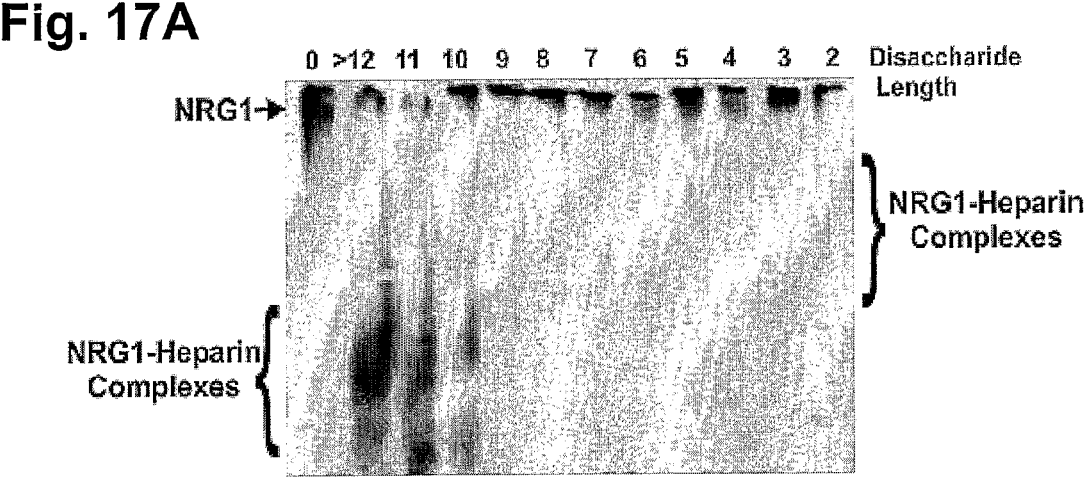
FIG. 17A-17B shows that sufficient heparin chain length is required for NRG1 binding and erbB receptor blockade.
Figure 17B:
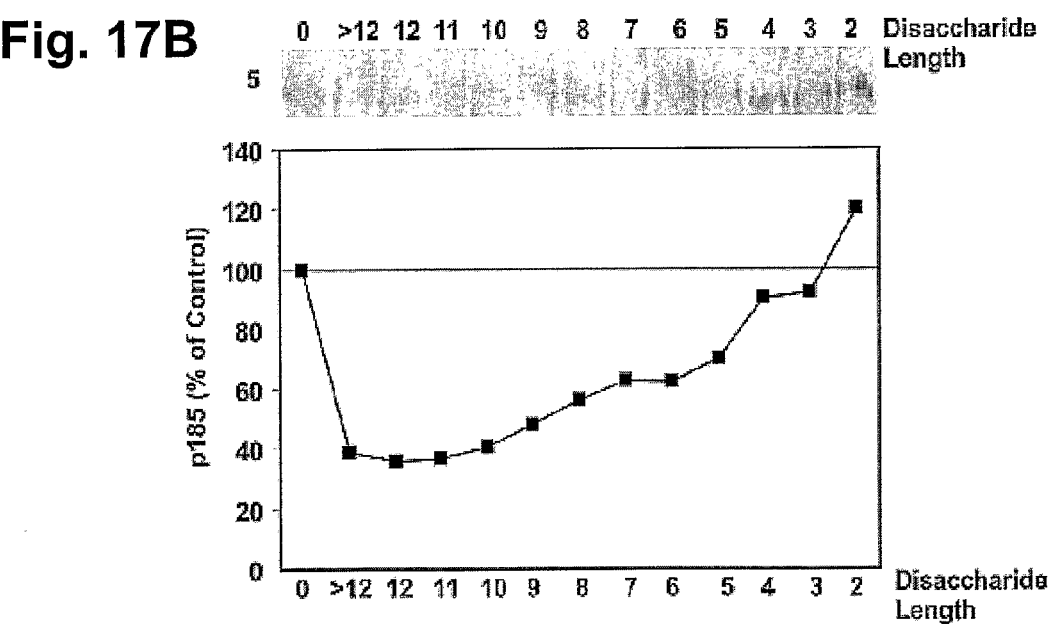
Figures 18A, 18B:
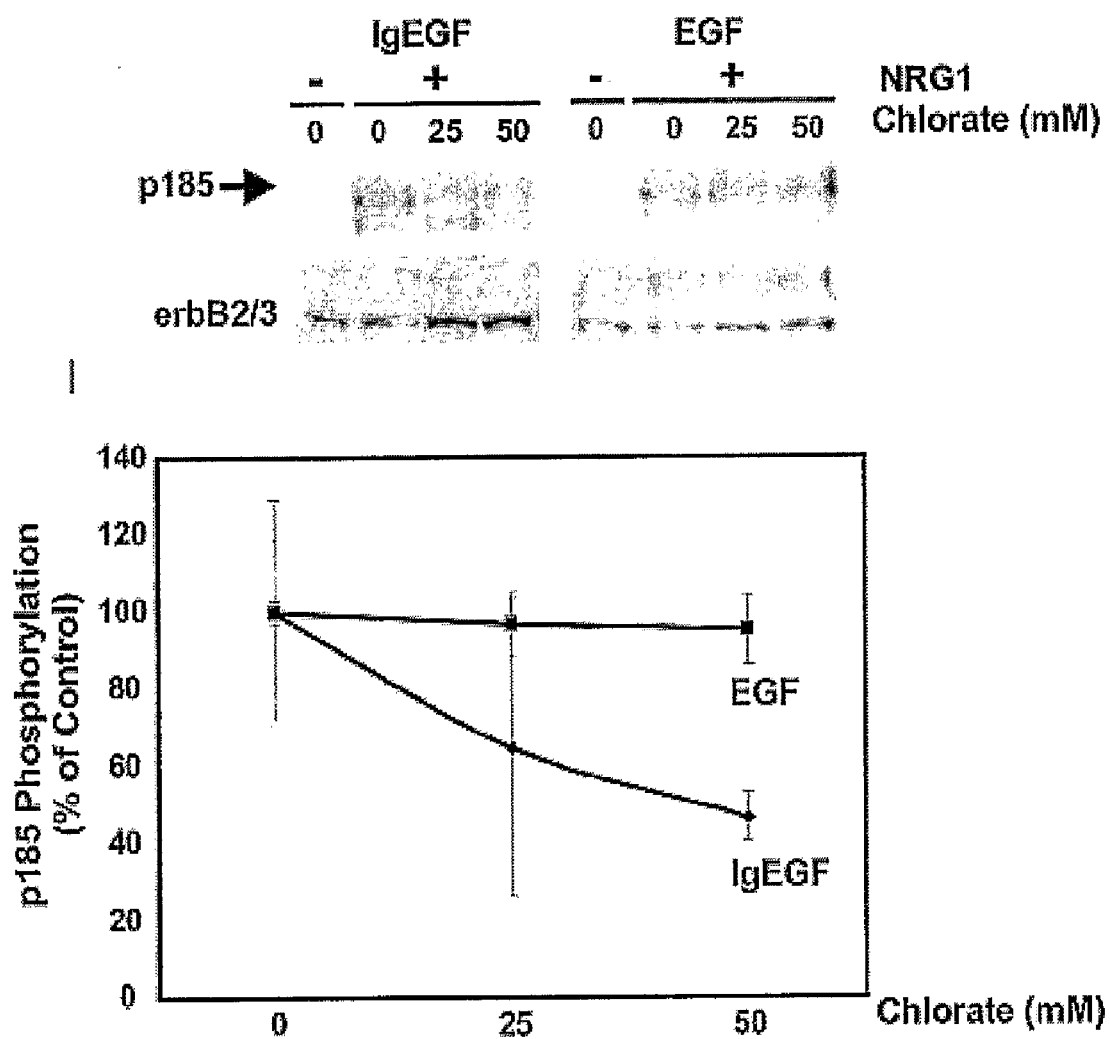
FIG. 18A-18B. Endogenous HSPG sulfation potentiates NRG1-induced erbB phosphorylation.
Figure 19A:
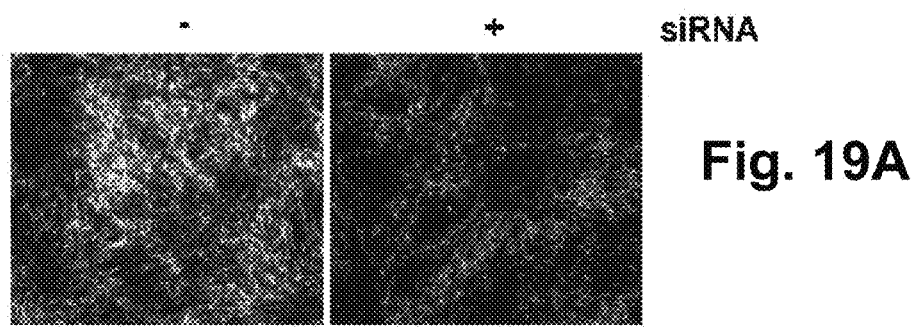
FIG. 19A-19C shows that endogenous HSPG N-sulfation potentiates NRG1-induced erbB phosphorylation. A reduction in N-sulfation was produced in L6 cells using an siRNA complementary to NDST-1 as shown by reduced staining in siRNA-treated cells (+) compared to control siRNA (−) (FIG. 19A). Quantitation of fluorescent intensities of 4 separate fields demonstrated an average of 47 (±11) % of control reduction in staining consistent with reductions in mRNA levels.
Figure 19B:
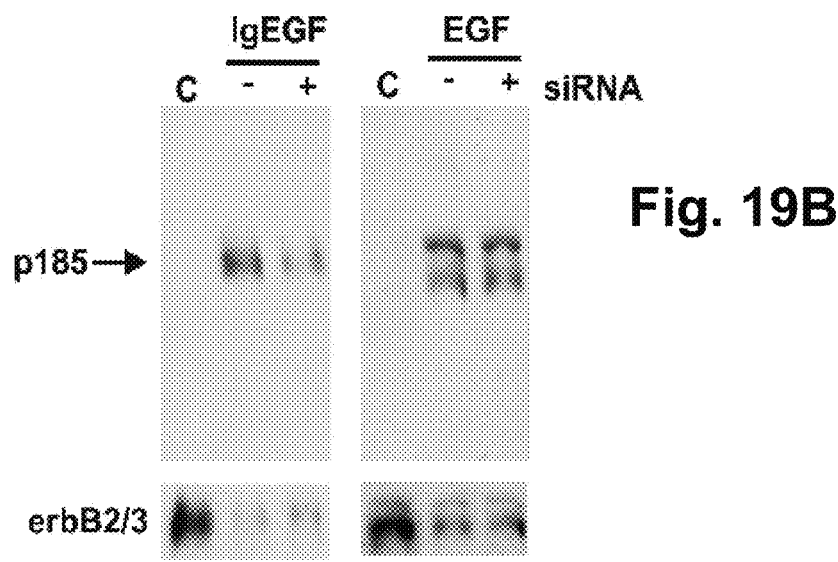
Figure 19C:
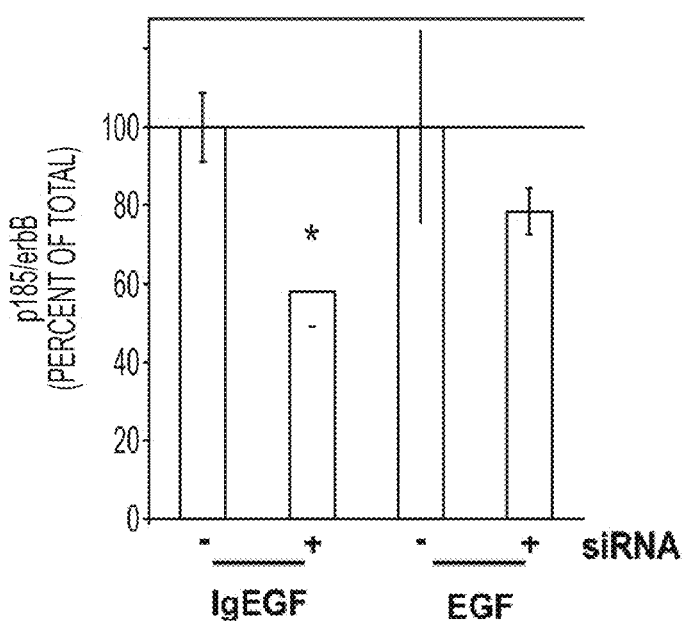

Using this gel mobility shift assay, fully sulfated heparin was compared to completely desulfated and de-N sulfated heparin. The completely desulfated heparin was unable to shift NRG1 mobility (FIG. 15A). This is not surprising, since the relatively neutrally charged desulfated heparin should have very low mobility even if complexed with NRG1. However, the De-N sulfated sugars, that should still migrate in the electric field, also did not shift NRG1, suggesting a critical importance of N-sulfation for NRG1 binding. The importance of 2O- and 6O-sulfation on NRG1 binding was examined using heparins lacking each of these groups. Both of these chemically modified heparins were equally effective in shifting NRG1, although not as effective as fully sulfated heparin, and more effective than the de-N sulfated heparin. This suggests an intermediate, but equal importance of these two sulfate groups for NRG1 binding (FIG. 15B).

The Same Rank-Order of Sulfate Groups on Heparin Block NRG1-Induced Receptor Phosphorylation in L6 Muscle Cells A limitation of the gel shift assays using western blots for NRG1 rather than radiolabeled oligosaccharides, as has been done for other heparin-binding proteins (Wu et al., 2002, 2003, supra), was that unbound NRG1 barely entered the gel, even at a higher pH. This produced variability in the intensity of the NRG1 band representing unbound NRG1 at the top of the gel. Because of this problem and as a second, independent means to confirm the relative importance of specific heparin sulfation patterns on heparin-NRG1 interactions, the ability of these same desulfated heparins to block erbB receptor phosphorylation in L6 muscle cells was tested. While the exact mechanism by which soluble heparins block erbB receptor activation is not known, it is a useful assay to compare the affinity of NRG1-heparin interactions in a biologically relevant system and has been used previously to define the relative affinities of different sulfated oligosaccharides (Loeb et al., 1995, supra). FIG. 16A shows that NRG1-induced erbB receptor phosphorylation is inhibited by fully-sulfated heparin in a dose-dependent manner. FIG. 16B shows a reduced efficacy for each of the modified heparins to block NRG1-induced erbB receptor phosphorylation. Similar to the gel mobility shift assay, completely desulfated and De-N sulfated heparins had little inhibition even at 100 μg/ml. Similarly, the 2O- and 6O-desulfated heparins again showed similar, intermediate effects compared to fully-sulfated heparin. The results were quantified in FIG. 16C and presented as a percentage of control. Curiously, low concentrations (1 μg/ml) of the De-N sulfated heparin had a modest stimulatory effect on receptor phosphorylation. This reproducible observation raises the possibility that low concentrations of a low-affinity heparin can potentiate erbB receptor activation by releasing NRG1 from endogenous HSPG binding sites on the cell surface.

Heparin Chain Length Effects on NRG1 Binding and erbB Receptor Blockade

The results thus far suggested an importance of the specific sulfation pattern to promote NRG1-heparin interactions, and demonstrated a hierarchy of importance for the sulfate groups. The importance of chain length on the NRG1-heparin interactions was investigated using a set of fully sulfated heparin fragments decreasing in size from 12 to 2 disaccharides on both GMSA (FIG. 17A) and receptor phosphorylation assays (FIG. 17B). As the heparin chain length was decreased, equal weight/volume concentrations of these oligosaccharides produced an upward shift in the predominant NRG1-heparin complex. The relative amount of NRG1 shifted also decreased with shorter heparin chain length, suggesting that longer heparins bind NRG1 more efficiently. With equimolar amounts of each oligosaccharide, an even greater difference between the larger and smaller oligosaccharides would have been expected. The appearance of multiple bands for a given oligosaccharide length raises the possibility either that multiple NRG1 monomers bind a single heparin chain or that multiple oligosaccharide monomers bind a single NRG1. Heparins as small as 2 disaccharides in length were able to shift small amounts of NRG1, seen on the right-hand side of the gel (and clearly seen on longer film exposures not shown here). The ability of various sized heparin fragments were compared for blocking of NRG1-induced receptor phosphorylation, parallel to the effects of NRG1 binding in FIG. 17A. As heparin chain length decreased, its ability to inhibit NRG1-induced erbB receptor phosphorylation was progressively impaired (FIG. 17B). Once the chain length was reduced to about 4 disaccharides or smaller there was no significant inhibition by heparin.

Endogenous Heparan Sulfate Groups Potentiate NRG1-Induced erbB Receptor Activation Endogenous HSPGs significantly enhance erbB receptor activation by heparin-binding forms of NRG1 (IgEGF), but not by forms of NRG1 that lack the heparin-binding Ig-like domain (EGF) (WO 03/012045; Li & Loeb, supra). The role of endogenous sulfation was examined by treating L6 muscle cells for 48 hours with chlorate, which competitively inhibits the formation of 3'-phosphoadenosine-5'-phosphosulfate (PAPS), the sulfate donor for sulfotransferase reactions (Safaiyan, F et al. (1999) *J Biol Chem* 274:36267-73; Gao, R et al. (2004) *J Biol Chem* 279:8848-55; Kaneider, N et al. (2004) *Biochemistry* 43:237-44). Using the full-length, heparin-binding form of NRG1 (IgEGF), chlorate treatment reduced receptor phosphorylation by 53%, whereas no reduction was seen with the EGF form that lacks the heparin-binding domain (FIG. 18A-18B). This documents the importance of endogenous HSPG sulfate groups to potentiate cellular interactions with NRG1.

Based on the specificity observed in the GMSA and erbB phosphorylation inhibition assays, the importance of the endogenous N-sulfate group for HSPG-NRG1 interactions in muscle cells was tested by reducing endogenous N-sulfation with an siRNA against GlcNAc N-deacetylase/N-sulfotransferase-1 (NDST-1), which is the most ubiquitously expressed of the four N-sulfotransferase isoforms, and shares a close homology with NDST-2 (Turnbull, J et al. (2003) *Biochem Soc Trans* 31:343-48; Grobe, K et al. (2002) *Biochim Biophys Acta* 1573:209-15). Treatment of L6 cells with this siRNA resulted in a 2-3-fold reduction in NDST-1 mRNA using 3 different primer pairs (primer set 1: −2.3-fold, primer set 2: −3.2-fold, primer set 3: −1.4-fold). The reduction in mRNA levels translated into a 47 (±11) % reduction in staining of N-sulfate groups using 10e4 antibodies that have been shown to require N-sulfate groups for their recognition (David, G et al. (1992) *J Cell Biol* 119:961-75) (FIG. 19A). Compared to the control siRNA, NDST-1 siRNA produced a 58% reduction in NRG1-induced (IgEGF) receptor phosphorylation ($p=0.004$). An insignificant 20% reduction in NRG1-induced erbB phosphorylation was observed with NDST-1 siRNA treatment using the isolated EGF domain of NRG1 (p=0.28) (FIG. 19B-19C). These results suggest an importance of endogenous N-sulfation on NRG1-HSPG interactions that parallels our results with the chemically-modified heparins.

Discussion of Example III

Given that virtually all cells express HSPGs and that the list of heparin-binding factors continues to grow, mechanisms are needed to discriminate which factors bind to and concentrate along a given cell surface in response to dynamic requirements during development and throughout life. Variations in the amount of HSPGs and their specific sulfation patterns are ways this could be accomplished. If a certain growth factor is needed, the cell could regulate the expression of enzymes that modify the GAG chains accordingly. In fact, regional specificity in HSPG structure has been observed with anti-heparan sulfate mAbs, each of which stains a unique region of skeletal muscle during development (Jenniskens, G J et al. (2000) *J Neurosci* 20:4099-4111). The localized expression of two different 6O-sulfotransferase enzymes in the anterior and posterior proximal chick limb bud, respectively, and a more uniform expression of 2O-sulfotransferase throughout the entire limb bud suggests that this diversity is not random, but highly coordinated during development through expression of synthetic enzymes (Nogami, K et al. (2004) *J Biol Chem* 279: 8219-29). Post-synthetic modifications of HS chains have also been described that may regulate the sulfation state of HSPGs through the activation of specific sulfatases. This includes the avian sulfatase Q-sulf1, which targets the S-domains of HS and promotes Wnt signaling (Dhoot, G K et al. (2001) *Science* 293:1663-66), and the mammalian homologue Hsulf-1 that is required to upregulate growth factor signaling in cancer (Lai, J et al. (2003) *J Biol Chem* 278: 23107-17).

In this Example, a set of chemically modified heparins were used to identify the specific sulfation requirements for optimal NRG1 binding. Using two, independent assays, GMSA and erbB receptor phosphorylation, a reproducible hierarchy of importance was discovered, with the N-sulfate groups most important for NRG1-heparin interactions followed by the 2O- and 6O-sulfate groups. The similar affinities seen with the De-2O and the De-6O sulfated heparins suggest that each contributes similarly to NRG1 binding. In addition to the sulfation state, the disaccharide chain length was important for optimal heparin-NRG1 interactions. While 8-12 disaccharides in length were necessary for maximal binding to NRG1, heparin fragments as small as 2 disaccharides could still bind, albeit to a limited extent. Since the erbB receptors exist as both homo- and heterodimers, binding multiple NRG1 polypeptides to a given oligosaccharide chain may potentiate erbB receptor signaling.

The specific sulfation requirements for NRG1-heparin interactions described here may also help explain the precise localization and potentiation of biological functions of NRG1 that associates with endogenous HSPGs at distinct tissue regions during development (Loeb, 2003, supra), and provides a basis for specific targeting of HBDs for particular sulfates. The blocking all endogenous HSPG sulfation with chlorate significantly reduced the ability of NRG1 to activate erbB receptors in L6 muscle cells. The effect of chlorate treatment on reducing NRG1 activity in muscle cells was not as pronounced as that seen previously after removing all HSPG GAGs with heparitinase (Li & Loeb, supra) or by β-D-xylose treatment that removes and releases GAGs into the culture media (Sudhalter, J et al. (1996) *Glia* 17:28-38). This is not unexpected since desulfation produced by chlorate is often incomplete and can be selective for specific sulfate groups (Safaiyan, F et al., supra).

The physiological importance of N-sulfation in mediating NRG1-heparin interactions was substantiated by reducing endogenous N-sulfation in muscle cells using an siRNA against NDST-1. Such treated cells showed a 2-fold reduction in NRG1-induced receptor phosphorylation, comparable to the effects seen with chlorate treatment, that was not seen with an isolated NRG1 EGF domain that lacked the HBD. The effectiveness of the siRNA treatment was documented by a 2-3-fold reduction in NDST-1 mRNA and a corresponding ~50% decrease in staining intensity with an antibody the binding of which requires an N-sulfated glucosamine residue (David et al., supra; Bai, X M et al. (1994) *J Histochem Cytochem* 42:1043-54). The ~2-fold effects seen here with the siRNA treatment may have resulted from residual NDST-1 activity or from compensation by other sulfotransferases (NDST-2-4) (Turnbull et al, supra). However, the siRNA sequence used against NDST-1 overlapped with NDST-2 for 19 out of 21 nucleotides and resulted in an approximately 2-fold reduction in NDST-2 mRNA as well.

N-sulfation of nascent GAGs of HSPGs is an early step in a sequential process (Turnbull et al, supra). Therefore, silencing of NDST-1 expression may have also reduced 2O- and 6O-sulfation. Taken together, while the chlorate result highlights the general importance of endogenous sulfation, the siRNA results suggest that specific HSPG sulfation patterns modulate NRG1-heparan sulfate interactions important for NRG1 localization and activation. Further analysis of mice with disruptions in genes that regulate heparan sulfation (Inatani, M et al. (2003)*Science* 302:1044-46; Ringvall, M et al. (2000) *J Biol Chem* 275:25926-30; Fan, G et al. (2000) *FEBS Lett* 467:7-11) will help in the understanding of these NRG1-HSPG interactions in vivo.

Example IV

Anti-Tumor Effects of HBD-S-B4 Fusion Polypeptide in Human Patients

All patients to be treated have histologically confirmed malignant masses confirmed by biopsy or cytology are entered. Malignant diseases including carcinomas, sarcomas, gliomas and medulloblastomas. Patients are those who have failed to respond to, or whose cancer is advancing despite, conventional therapy. Patients in all stages of malignant disease involving any organ system are included. Staging describes both tumor and host, including organ of origin of the tumor, histologic type, histologic grade, extent of tumor size, site of metastases and functional status of the patient. For a general classification includes the known ranges of Stage 1 (localized disease) to Stage 4 (widespread metastases), see Abraham J et al., *Bethesda Handbook of Clinical Oncology*, Lippincott, Williams & Wilkins, Philadelphia, Pa., 2001 (or a more recent edition). Patient history is obtained and physical examination performed along with conventional tests of cardiovascular and pulmonary function and appropriate radiologic procedures. The malignant masses are visible on x-ray or CT scan and/or are measurable with calipers. They have not been undergoing any other anticancer treatment for at least one month and have a clinical KPS of at least 50.

HBD-S-B4 is used as the prototypical fusion protein (but other homologues and functional derivatives described herein are used in other patients in comparable doses, and yield similar results). HBD-S-B4 is administered intravenously in doses of 0.01-100 µg/kg intratumorally once every 2-7 days. Patient Evaluation: Assessment of response of the tumor to the therapy is made once per week during therapy and 30 days thereafter using CT or x-ray visualization. Depending on the response to treatment, side effects, and the health status of the patient, treatment is terminated or prolonged from the standard protocol given above. Tumor response criteria are those established by the WHO and RECIST (Response Evaluation Criteria in Solid Tumors) summarized below (e.g., Abraham et al., supra)

| RESPONSE | DEFINITION |
|---|---|
| Complete remission (CR) | Disappearance of all evidence of disease |
| Partial remission (PR) | 50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≧25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term and short term changes in measurements are evaluated separately.

Results

A total of 400 patients are patients treated. The number of patients for each tumor type and the results of treatment are summarized in Table 1. Positive tumor responses are observed in as many high as 77-85% of the patients with breast, ovarian and gastrointestinal tumors (including gastric, esophageal, colon and rectal).

Three hundred and five patients with all tumors exhibit objective clinical responses for an overall response rate of about 76%. Tumors generally start to diminish and objective remissions are evident after four weeks of therapy. Responses endure for an average of 24 months.

Toxicity consists of mild short-lived fever, fatigue and anorexia not requiring treatment. The incidence of side effects (as % of total treatments) are as follows: chills—10; fever—10; pain—5; nausea—5; respiratory—3; headache—3; tachycardia—2; vomiting—2; hypertension—2; hypotension—2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. CBC, renal and liver functions tests do not change significantly after treatments.

TABLE 1

|  | No. | Response | % of Patients Responding |
|---|---|---|---|
| All Patients | 239 | CR | 59.7 |
|  | 45 | PR | 11.3 |
|  | 21 | <PR | 5.3 |
| By Tumor Type: |  |  |  |
| Breast adenocarcinoma | 100 | CR + PR + <PR | 85% |
| Ovarian carcinoma | 100 | CR + PR + <PR | 82% |
| Gastrointestinal carcinoma | 100 | CR + PR + <PR | 77% |
| Brain glioma/astrocytoma | 100 | CR + PR + <PR | 61% |

The references cited above are all incorporated by reference herein, whether specifically incorporated or not, including the present inventor's application PCT/US02/24053 (published as WO 03/012045).

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A fusion polypeptide comprising (a) a targeting polypeptide that comprises a human neuregulin heparin binding domain (N-HBD); and (b) fused directly C-terminally to the N-HBD, a peptide linker or spacer (S) that is the natural amino acid spacer of human neuregulin, the sequence of which is residues 131-195 of SEQ ID NO: 14, and (c) fused directly C-terminally to S, a targeted polypeptide that comprises human erbB4 receptor extracellular domain (B4-ECD) that is to be targeted and localized to the heparan sulfate-rich cell or tissue surface;

wherein (i) said fusion polypeptide binds heparan sulfate when said fusion polypeptide is permitted to contact cells or tissues, thereby localizing the B4-ECD of (c) to heparan sulfate-rich cell or tissue surface; and (ii) said fusion polypeptide has enhanced biological activity in blocking a target receptor compared to native human B4-ECD or human B4-ECD that is not fused to said S and said human N-HBD.

2. The fusion polypeptide of claim 1 further comprising a tag sequence.

3. The fusion polypeptide of claim 2 wherein the tag sequence is a C-terminal influenza hemagglutinin (HA) sequence.

4. The fusion polypeptide of claim 1 the sequence of which is SEQ ID NO: 14, in which the N-HBD is residues 31-130 and B4-ECD is residues 200-820.

5. A pharmaceutical composition useful for delivering a B4-ECD to a cell or tissue surface and enhancing the biological activity of the B4-ECD, comprising:

(a) the fusion polypeptide of claim 1; and (b) a pharmaceutically acceptable excipient or carrier.

6. A pharmaceutical composition useful for delivering a B4-ECD to a cell or tissue surface and enhancing the biological activity of the B4-ECD, comprising:

(a) the fusion polypeptide of claim 4; and (b) a pharmaceutically acceptable excipient or carrier.

7. A method of inhibiting the activation by neuregulin of an EGF-receptor and/or inhibiting the stimulation of the growth of cells bearing such receptor by neuregulin, comprising providing to said receptor or cells an effective amount of the fusion polypeptide of claim 1, that inhibits binding of neuregulin and activation of said receptor.

8. A method of inhibiting the activation by neuregulin of an EGF-receptor and/or inhibiting the stimulation of the growth of cells bearing such receptor by neuregulin, comprising providing to said receptor or cells an effective amount of the fusion polypeptide of claim 4, that inhibits binding of neuregulin and activation of said receptor.

9. A method for treating a tumor or cancer in a subject in which tumor growth and/or metastasis is dependent upon autocrine neuregulin signaling, comprising administering to said subject an effective amount of the pharmaceutical composition of claim 5, wherein the biological activity of the B4-ECD of the fusion polypeptide is increased compared to the activity of native B4 ECD or a B4 ECD not fused to said S and said human N-HBD, thereby treating said tumor or cancer.

10. The method of claim 9 wherein said tumor or cancer is a breast or ovarian tumor or cancer.

11. A method for treating a tumor or cancer in a subject in which tumor growth and/or metastasis is dependent upon autocrine neuregulin signaling, comprising administering to said subject an effective amount of the pharmaceutical composition of claim 6, wherein the biological activity of the B4-ECD of the fusion polypeptide is increased compared to the activity of native B4 ECD or a B4 ECD not fused to said S and said human N-HBD, thereby treating said tumor or cancer.

12. The method of claim 11, wherein said tumor or cancer is a breast or ovarian tumor or cancer.

* * * * *